United States Patent [19]
Fabijanski et al.

[11] Patent Number: 6,162,964
[45] Date of Patent: *Dec. 19, 2000

[54] MOLECULAR METHODS OF HYBRID SEED PRODUCTION

[75] Inventors: Steven F. Fabijanski, Gloucester; Paul G. Arnison, Cumberland, both of Canada; Diego Albani, Sassari, Italy; Laurian Sylvio Robert, Gatineau, Canada

[73] Assignee: Pioneer Hi-Bred International, Inc., Des Moines, Iowa

[*] Notice: This patent is subject to a terminal disclaimer.

[21] Appl. No.: 09/161,313

[22] Filed: Sep. 28, 1998

Related U.S. Application Data

[62] Division of application No. 08/897,325, Jul. 21, 1997, abandoned, which is a division of application No. 08/276,510, Jul. 14, 1994, which is a continuation of application No. 07/556,917, filed as application No. PCT/CA90/00037, Feb. 2, 1990, abandoned, which is a continuation-in-part of application No. 07/306,438, Feb. 3, 1989, abandoned, which is a continuation-in-part of application No. 07/151,906, Feb. 3, 1988, abandoned.

[51] Int. Cl.⁷ .............................. A01H 1/02; A01H 5/00; A01H 5/10; C12N 15/82; C12N 15/52
[52] U.S. Cl. ........................ 800/274; 800/278; 800/287; 800/303; 800/288; 536/23.2; 536/24.1; 536/23.7
[58] Field of Search ..................................... 800/274, 278, 800/287, 288, 303; 536/23.7, 23.2, 24.1

[56] References Cited

U.S. PATENT DOCUMENTS 5,107,065   4/1992   Shewmaker et al. .................... 800/205

FOREIGN PATENT DOCUMENTS

| | | |
|---|---|---|
| 2021643 | 8/1991 | Canada . |
| 0198288 | 10/1986 | European Pat. Off. . |
| 0223399 | 5/1987 | European Pat. Off. . |
| 0240208 | 7/1987 | European Pat. Off. . |
| 0332104 | 9/1989 | European Pat. Off. . |
| 0 589 841 | 3/1994 | European Pat. Off. . |
| WO 88/05077 | 7/1988 | WIPO . |
| WO 89/09260 | 5/1989 | WIPO . |
| WO 89/09262 | 5/1989 | WIPO . |
| WO 89/10396 | 11/1989 | WIPO . |
| WO 90/08828 | 8/1990 | WIPO . |
| WO 92/01799 | 2/1992 | WIPO . |
| WO 92/04454 | 3/1992 | WIPO . |

OTHER PUBLICATIONS

McCormick et al., Anther–Specific Genes: Molecular Characterization and Promoter Analysis in Transgenic Plants, 1989, Plant Reproduction: From Floral Induction to Pollination, Lord, E., Bernier, G., eds. ASPP Sympos., vol. 1, 128.

McCormick et al., Identification of Genes Specifically Expressed in Reproductive Organs of Tomato, 1987, *Tomato Biotechnology*, 255.

Hanson et al., Characterization of a Pollen–Specific cDNA Clone from *Zea mays* and Its Expression, 1989, *The Plant Cell*.

Stinson et al., Genes Expressed in the Male Gametophyte of Flowering Plants and Their Isolation, 1987, 83 *Plant Physiol.*, 442.

Twell et al., Isolation and Expression of an Anther–Specific Gene from Tomato, 1989, 217 *Mol. Gen. Genet.* 240.

Mascarenhas, Characterization of Genes that are Expressed in Pollen, 1989, The Molecular Basis of Plant Development, 99.

Gasser et al., Analysis of Floral Specific Genes, 1988, *Journal of Cellular Biochemistry* Supplement 12C, Abstract L021.

Gasser et al., Isolation of Tissue–Specific cDNAs from Tomato Pistils, 1989, *The Plant Cell*, vol. 1, 15.

Izant & Weintraub, Constitutive and Conditional Suppression of Exogenous and Endogenous Genes by Anti–Sense RNA, 1985, *Science* V.229, 345.

Weintraub et al., Anti–Sense RNA as a Molecular Tool for Genetic Analysis, 1986, *Trends in Genetics*, vol. 1, 1.

McGarry & Lindquist, Inhibition of Heat Shock Protein Synthesis by Heat–Inducible Antisense RNA, 1986, 83 *PNAS*, 399.

Rothstein et al., Stable and Heritable Inhibition of the Expression of Nopaline Synthase in Tobacco Expressing Antisense RNA, 1987, 84 *PNAS*, 8439.

Sandler et al., Inhibition of Gene Expression in Transformed Plants by Antisense RNA, 1988, *Plant Molecular Biology*, 11:301–310.

Delauney et al., A stable Bifunctional Antisense Transcript Inhibiting Gene Expression in Transgenic Plants, 1988, 85 *PNAS*, 4300.

Simpson et al., Light–Inducible and Tissue–Specific Expression of a Chimeric Gene Under Control of the 5'–Flanking Sequence of a Pea Chlorophyll a/b–binding Protein Gene, 1985, 4 *EMPO, Journal No. 11*, 2723.

Halling, et al., *Nucleic Acids Res.*, 13(22):8019–8033 (1985).

Sanders, et al., *Enzyme Microb. Technol.*, 9:250–251 (1987).

Smith, et al., *Nature*, 334:724–726 (1988).

(List continued on next page.)

Primary Examiner—David T. Fox
Attorney, Agent, or Firm—Foley & Lardner

[57] ABSTRACT

A process is described for producing fertile hybrid seed or hybrid seed comprising fertile and sterile seed using male-sterile plants created by employing molecular techniques to manipulate anti-sense gene and other genes that are capable of controlling the production of fertile pollen in plants. Said plants are functionally male-sterile plants with pollen from male-fertile plants. Hybrid seed production is simplified and improved by this invention and can be extended to plant crop species for which commercially acceptable hybrid seed production methods are not currently available.

5 Claims, 49 Drawing Sheets

OTHER PUBLICATIONS

Kamalay, et al., *Proc. Natl. Acad. Sci. USA*, 81:2801–2805 (1984).

Grill, L., *Plant Mol. Biol. Rep.* 1(1):17–20.

Nagy et al., Photoregulated Expression of Pea rbcS Gene in Leaves of Transgenic Plants, 1985, *4 EMBO, Journal No. 12*, 3063.

Medford & Klee, Manipulation of Auxin, Cytokinin and Gus Levels Using the Maize HSP70 Promoter, 1988, *J. of Cellular Biochem.* Supp. 12C, Ab L616.

Maxwell et al., Regulated Expression of a Diphtheria Toxin A–Chain Gene Transfected into Human Cells: Possible Strategy for Inducing Cancer Cell Suicide, Sep., 1986, *Cancer Research* 46:4660–4664.

Palmiter et al., Cell Lineage Ablation in Transgenic Mice by Cell–Specific Expression of a Toxin Gene, Jul. 31, 1987, *Cell*, 50:435–443.

Breitman et al., Genetic Ablation: Targeted Expression of a Toxin Gene Causes Microphthalmia in Transgenic Mice, Dec., 1987, Reports 1503, *Science* vol. 238.

Medford et al., Manipulation of Auxin, Cytokinin and Gus Levels Using the Maize HSP70 Promoter, 1988, Abstract 616 Keystone Symposium at Steamboat Springs, CO.

Sitbon et al., Free and Conjugated Indoleacetic Acid (IAA) Contents in Transgenic Tobacco Plants Expressing the iaaM and iaaH IAA Biosynthesis Genes from *Agrobacterium tumefaciens*, 1991, *Plant Physiol.* 95:480–485.

Evans, Glen A., Dissecting mouse development with toxigenics, 1989, *Genes & Development* 3:259–263.

Landel et al., Lens–specific expression of recombinant ricin induces developmental defects in the eyes of transgenic mice, 1988, *Genes & Development* 2:1168–1178.

Borrelli et al., Targeting of an inducible toxic phenotype in animal cells, Oct., 1988, *PNAS USA* 85:7572–7576, Cell Biology.

Hamilton et al., Characterization of a pollen–specific genomic clone from maize, 1989, *Sex Plant Reprod.*, 2:208–212.

Takatsuji et al., Characterization and Cloning of Flower–Specific and Developmental Stage–Specific DNA Binding Protein of the EPSPS Promoter from Petunia, A 639, The Genetic Dissection of Plant Cell Processes.

Thorsness et al., A Brassica S–Gene Promoter Targets Cell Specific Death in Transgenic Arabidopsis, A 640, The Genetic Dissection of Plant Cell Processes.

Ursin et al., Gametophytic and Sporophytic Expression of Anther–Specific Genes in Developing Tomato Anthers, Jul. 1989, *The Plant Cell*, 1:727–736.

Tunen et al., Regulation of chalcone flavanone isomerase (CHI) gene expression in *Petunia hybrida*: the use of alternative promoters in corolla, anthers and pollen, 1989, *Plant Molecular Biology* 12:539–551.

Tunen et al., Pollen– and Anther–Specific chi Promoters from Petunia: Tandem Promoter Regulation of the ChiA Gene, May 1990, *The Plant Cell* 2:393–401.

Goldberg, Robert B., Emerging Patterns of Plant Development, Unique Aspects of Plant Development, May 8, 1987, *Cell* 49:298–300.

Inze et al., Genetic analysis of the individual T–DNA genes of *Agrobacterium tumefaciens*: further evidence that two genes are involved in indole–3–acetic acid synthesis, 1984, *Mol Gen Genet* 194:265–274.

Furman et al., Inhibition by Acyclovir of Cell Growth and DNA Synthesis of Cells Biochemically Transformed with Herpesvirus Genetic Information, 1980, *Virology* 102:420–430.

Klee et al., The effects of overproduction of two *Agrobacterium tumefaciens* T–DNA auxin biosynthetic gene products in transgenic petunia plants, 1987, *Genes & Development* 1:86–96.

Depicker et al., A negative selection scheme for tobacco protoplast–derived cells expressing the T–DNA gene 2, 1988, *Plant Cell Reports* 7:63–66.

Paddon et al., Cloning, sequencing and transcription of an inactivated copy of *Bacillus amyloliquefaciens* extracellular ribonuclease (barnase), 1986, *Gene* 40:231–239.

Hartley, Robert W., Barnase and Barstar Expression of Its Cloned Inhibitor Permits Expression of a Cloned Ribonuclease, 1988, *J. Mol. Biol.* 202, 013 915.

Moffatt et al., "Positive Selection for Male–Sterile Mutants of Arabidopsis Lacking . . . ," *Plant Physiol.*, 86:1150–1154 (1988).

Stinson et al., "Gene Expression in the Male Gametophyte of Flowering . . . ," *Plant Physiol.*, 83:442–447 (1987).

McCormick et al., "Identification of Genes Specifically Expressed in Reproductive . . . ," *Tomato Biotech.*, 255–265 (1987).

Izhar et al., "Mechanism of Male Sterility in Petunia: The Relationship . . . ," *Theor. and Appl. Genetics*, 41:104–408 (1971).

Frankel et al., "Timing of Callase Activity and Cytoplasmic Male Sterility in Petunia," *Biochem. Genetics*, 3:451–455 (1969).

Mascarenhas, Joseph P., "The Biochemistry of Angiosperm Pollen Developmemt," *The Botanical Review*, 41(3):259–315 (1975).

Mascarenhas et al., "Genes and Their Expression In The Male Gametophyte . . . ," *Biol. and Ecology of Pollen*, 39–44 (1986).

Malik et al., "Male Sterility," *Recent Advances in Pollen Research*, 172–200 (?).

Heslop–Harrison, J., "Cell Walls, Cell Membranes and Protoplasmic Connections . . . ," *Biochem. of Pollen Wall Formation*, 39–47 (?).

Willing et al., "An Analysis of the Quantity and Diversity of Messenger RNAs . . . ," *Theor. Appl. Genetics*, 75:751–753 (1988).

Sawhney et al., "Microsporogenisis in the Normal and Male–Sterile Stamenless–2 Mutant . . . ," *Can. J. Bot.*, 66:2013–2021 (1986).

Jewell et al., "Light and Electron Microscope Studies On Pollen Development . . . ," *Plant, Cell and Environment*, 11:273–281 (1988).

Chapman, G.P., "The Tapetum," *International Review of Cytology*, 107:111–125 (1987).

Stinson et al., "Onset of Alcohol Dehydrogenase Synthesis during Microsporogenesis In Maize," *Plant Physiol.*, 77:222–224 (1985).

Vasil, Indra K., "The New Biology of Pollen," *Naturwissenschaften*, 60:247–253 (1973).

Grant et al., "A Comparative Light and Electron Microscopic Study of Microspore . . . ," *Can. J. Bot.*, 64:1055–1068 (1986).

Blackmore et al., "The Systematic Implications of Pollen . . . ," in *Ontogeny and Systematics*, Columbia Univ. Press, 83–115 (1988).

Lewin, R. *Science*, 237:1570 (1987).

Reeck, et al., *Cell*, 50:667 (1987).

FIG. 3A

```
  1  GAATTCTAAAAATAGCAATAACTTTTTGAGAACATCAGATTTAGTACACGCATAGGACA          60
 61  CATACCTTTTTATTTACTTAAAGGAAAATGAACGAGTCTAAATCTTCCACATGTTATATG        120
121  AGCAAAAACATGAATTTTCTAAATAGATTCGTTTAAATCAGAACATATTAATGTGAGTT         180
181  TCTTAAATTAGATTTTTAATATCTATATATACGTAAGAATACTTCTTATGTTTAAAATA        240
241  AAAAATAGAATACTTCATCTCTTCCTAAATTTTTAAGCCAATATCAATCATTCTATA          300
301  ATCTAAGATGAAGAAATCCCTTCAACTCTCTTTCGTTCTTAATTATCTCCATCATTCT         360
                M  K  K  S  L  Q  S  F  S  F  L  I  I  S  I  I  L
361  CTCACACATGGTTTGTATTTCACTCTTAATATATTGCATATAGTAATTCCATATAAATTGA      420
      S  H  G
421  TTATACTAAAAATTTGACTTTTAAAATATGTCAACCCCATATAATAAATTTATTTACT         480
481  ATATAAAACATAGCATTAAATTATCTCTTTGTAAATTCATACTTTGCAGAAGCTA            540
541  GAAAATATAGATAGTAGTAGTCAGAAATGTTCGTTAAAATGAAAGGATCACCATGGA          600
601  GTATTTAAATGTTTTTTATACTTTATGCCATTTATAATTTTTAATGTATGGGTTTATA         660
661  TATGATGAAGAACTATTAATGATAAAATAATTAAATATTCATTTTTATCATCTATTT          720
```

FIG. 3B

```
 721  ATGAACATTTGTCCTGCACATACAAATGATTAACCACATTTTAATAATATGGATGA                          780
 781  ACTATAGCTCTTAGTAAATTATTTGATATTTTAATTAAATTATATATTTTATAGG                           840
 841  TAATTGTTATGCTTTTCCAATACATACAGTAGTGTTATTAAATATCAAAATTTAATA                         900
 901  CGTAATGTTTATTAATATGCACACAATTCTTAAAACCATATTTTAAAAAATAATGTTG                        960
 961  ACCAAACGATATGCTCATTTTTTATTACTAGCAAAATATATTCTTTCTTACTTATA                         1020
1021  ACGTTTAAAAAGAAAATGTTATTAAACATTTTTGCTGATAAATAAATTTATATTCATA                       1080
1081  AAATCTAAATATATTTTTAACAATTAAAATTTGAAATTTTATATCTTACAGGAATGAT                       1140
                                                                M  M
1141  GGCAGATGCGGCAGAAAAAGAATTGTCCTCATAAATTCAATAAAAGAAGTTATTGTGC                       1200
       A  D  A  Q  K  K  N  C  P  H  K  I  P  I  K  G  S  Y  C  A
1201  TCCAACTATATGTTTGGATATGTGTAAGAAGCAACATGGAACTGTTGGTAGTTGTGCGGA                      1260
       P  T  I  C  L  D  M  C  K  K  Q  H  G  T  V  G  S  C  A  E
1261  ATAAAAATGATTTTGTAACTGCCTTGTAAGTAAGGTTCTCACTAAGTGTATGAATCT                        1320
      STOP
```

FIG. 3C

```
1321  AGTAATGTCCAACCAAAGTTTATATTATTCTTTTAACAATAAGTCTAAATGTTTGTCT    1380
1381  CAGATTTGTGGATCTATTTATAATAATAATATGAATGTTAAATAATACAAATGTG        1440
1441  TAAAACAAGAGTGACTATTAATAAAATATGATTACATTATTGTTAGAAGTAACCAAT      1500
1501  ATTAGTGTAAAATCAAAATCTTAAGACAAGTTAAAAAGATTGAGATGAAATCACAACCA    1560
1561  ATATTTAAATGTGAAAATCACATGTAATTTGTACACATGTAAAAAAAAAAA            1620
1621  AGCAAGAGTTCATTATCAAACAAGAAAGTTAGAAAAGAGCAACAGATTCATGCAAGG      1680
1681  CAGTCTAGGTTGAATTGGCTTGACATAGGGAAAATGAAAGCACTGTTTCTGAACATGAC    1740
1741  AACGCTTGGTCAGGAAGAACAATCTCACAACCAGAGTTTGGGTAGATTCTCCAATGTC    1800
1801  ATTATCAGGTACGAGTTATGAGACTTCATCCAGTCCCTTCTCAGGA                 1860
1861  AGTTTCCTTGAGGAAGGAGGTTATTACAGAAGCTAAGTTACATGAGCTGACATATCAT    1920
1921  GCAAGGGCAGTCCCAACAAGAAAATGTTAGAAGAGCAACATATCATGCAGGACAGTCC    1980
1981  AGGTTTGAATGGCTTGACAGATGGTTTGCAGACATGCCATCTGAAGTCCTACAAACTC    2040
2041  ATCAGTACAACGAAGAAATTGATAGCATTGTTTCTGAACATGACAAAACTCAGTCAGG    2100
```

FIG. 3D

2101 AAGAAGAATCTCACAACCAAAGTTTGGGTAGAGCTCCTCCAATGTCATCATCAGCTACG 2160
2161 AGTTCAAAGACTTCATCCACATCTTAGTCCCCATTCTCTCTCATGAAGTTCCTTTAG 2220
2221 AAAGAGGTTATTACAGAAAGCCAAGTTACATGAGCCTAACAATCATCAAAGCTAAGA 2280
2281 AGAGACGATTAACCATTATTCTTCATCTTTTGTCCCAAATCACTGTTTGAAAGAAAC 2340
2341 AGTCCATGTCTTACAACGAAGATGTGAATGTAAAGGTTGTGCATGTCCGATCCATCTT 2400
2401 GCAACCAGCAGAGTTATCTATATCCACACATGCTCAAGTAACAAGGAAAAATATGTGGGCAA 2460
2461 AGAAGGTAAAGTGAACATGTTTCATTAATTCATTAAAGCATTTCAACACCTTGATGTT 2520
2521 CTAAATACACACAAAAACACTGATTATAGATACATAAGCAACTTCTGTATGTTCTTT 2580
2581 ACATACAAGTTGGTATCAAGGCTGTTGCAATGTGTGTTTGACCACTTTTATTATTAA 2640
2641 TAGTTAACTTTTGATGCTTCTAAGATAATATGTTCCTCCTAACTCTGTCAACATGAAAG 2700
2701 ACCAATTAAAGGTTTTGATTAAATACATACTAATTTTTAATATAATCTATAAGTTATG 2760
2761 TTACGTGTGGGACATCCACCTAATAAACTATAAATTTAAATAATTAAGTTTGAAAGGAT 2820

FIG. 3E

```
2821  TTTATTGACATTCCTTAAATAAATCATAATTTAAAAAATAGGATAACTTTTTGAAAA        2880
2881  CATCAGAATTATGTACACGCAGAGAGACACATACCTTTTTATTACTTATAGGAAAATGAA    2940
2941  CGAGTCTAAAGCTTCCACACATGTTATATGAGCAAAACATGGATTTTTCTAAATTAGATTCG  3000
3001  TTTAAATCAGAACATATTAATGAAGTTTCTTAAATTAGATTTTAATATGTATATATAT      3060
3061  GTAAAAATACTTCTTTTTTTTTGTCATCAGCATTACAGATTCTAAATAAGTTAC          3120
3121  TTCTTATGTTTAACAATAGAATACTTCATCTCTTCCTAAATTTAAGTCAATATCAA        3180
3181  TCCATTTCTATAATCGAAGATGAAGAAATCCCTTCATCCTGAGAAATAGGTCAGAAA       3240
3241  GTTTTCGGTTAAAATGAAAGGATCATCCCTGAAGTATTATTTGTTTTTTATGCTTT        3300
3301  AGTCCATTAATATTTTTAAGTATGGGTTTATATATGATTAAGAACTTCCATGATAAA       3360
3361  ATAATATTAAATAGTTTATTCTTATCATCTATTTATGAACGTTTGTTCCTGCACACAC      3420
3421  AAATGATTAACCAACATTTTCATAATATGGATAAACTATAGTTCTTAGTAAATTTAT       3480
3481  GTGATATTTTAATTAGATTTATTATAGGTAATCTATTATGCTTTTCCAATACATA         3540
3541  CAGTAGTTGTCTTAAAACATCAAATTTTATATGTAATGTTTATTAATATGCACACAAT      3600
```

FIG. 3F

```
3601  TCTTAAAACAATATTTCACACAACATAAAAAAATAATGTTTGACCAACCATATGCTCATT  3660
3661  TTCTTTATTTACCGGCAAAAACCATTTCTCCATTTTTTACTTATAACGCTTAAGATAAAA  3720
3721  AAAATTATTAAACAGTTTTTGTTGATAAATAAGTTTATATATTTCAGAAAATGTATTATAT  3780
3781  TTTCAAACAATTAAAAATTGGGTTTTTTATATCTAACATAAATGATGGCAGAAGCACAGAA  3840
3841  AAATAATGTCTTCATAAATTCCAATAAAAGGAAGCTAGTGCATTCCAAATAAATGTTT  3900
3901  GGCTATGTGTAAGAGCAACATGGACTCTTGGTAGTGTCCGAAGTGTCCGAAAAGAAATTGTAG  3960
3961  TTGTGCCTTGTAAGTAAGGGTTCTCACTAAGTGTATGAATCTAATAATGTCCAACCAAAG  4020
4021  TTGTATATAATTTTTAACAATAAATGTCTAAATGTTTGTCTCAGATTGTGGATCTATT  4080
4081  TATAATAAATAATAATGAATGTTAAATAAATACAAATGTGTAAAAAAGATTGGACTA  4140
4141  TTAATAAATAAAATGATCCATTATTATTAGATGTAACCAATATGTATAAGATGTA  4200
4201  AAAGCTTAAGACGAGTTAAAAAGATAGAGATGAAATCACATCCAATATCTAAATGTGAGA  4260
4261  TAATCAACTAACATATAATTTGTATATTGTAAGATAAAATAAAAATAAAAATTAAAA  4320
```

FIG. 3G.

```
4321  AGCAAGAGTTGATTATCAAACAAGAAGAGTATTAGAAAGAGCAACAGATCATGCAAGAGA  4380
4381  GTCCATGTTTGAATTTTCTTGACAGATGGGTTGCAGACAAGTCATGGAAGGTCATACAA   4440
4441  ACTCATCAGACACCCAAAGAAAATTGATAGCACAGTTTCTGAACATGACAAAGCTCTG    4500
4501  TCATGAAGAACAATCTCACAAGCAGAGTTTTGGGTAGACCTCCTCCAATGTCATCATCAG  4560
4561  CTACGAGCTCTGAGACTTCATCCACATCTCAGTCCTCAGTTTCTTCCCAGGAAGTTTCCT  4620
4621  TGAGGAAGGAGGTTATTACAGAAATCCAAGTTACATGAGCCCTGGCAAAATCTATCAAAGC  4680
4681  TAAGCAGAGATGATCACGGTATTCTTCATCGTCTTCTCCAAAACCTGGTTGAGAAAAA    4740
4741  ACAATCCATGTCTTACACAGAGATGTAAAATGAAAGTGTGTTTGTTTGGATCAATC      4800
4801  TTGCAACCAGTGGAGTGATCTATATCGACCGGTTCAAGTAACAAGGAGAACTATGTGGA   4860
4861  AAGAGGCTAAATTAAATAACTTCGGATGCTTCATCAAAGATTGTTGCAATGTGTGTTTGGCCACT  4920
4921  TTGATTATTAATAATTAACTTCGGATGCTTCTGAGACAATCTGTCCTCCATTTTG       4980
4981  TCAATATGAAACGAAGACAATCTTCATCTTTAGACATGAAAAGCCATTAAATGACCA     5040
5041  AATAACATAGTTTATACCAAAGCTTCCTTATAAATTTTACCGTCTAAAAATTGCTCTT    5100
```

FIG. 3H

| | | |
|---|---|---|
| 5101 | ACTATCAAAATCTAAAAACTGAATTAAATTCAATTATCTTACTGTTACACAGTTTTCACTA | 5160 |
| 5161 | ATCACTATTTAATGTATAAACTATAAAATATAAATACTTACTAAATTTTTAGATT | 5220 |
| 5221 | TAATCCATAAATTATATTACAGTTCAGAGATTCATCCACATTCAGTCCCCAGTCCCTT | 5280 |
| 5281 | ACTCATAAATTTCTGAGGAAGGAGGTTATACAGAAAGTCAACTACATGAGCCTTAC | 5340 |
| 5341 | TCAATCTATCAAAGCTAAGAGAGATGTCAGTTCTCTTCATCTTTCTGTTCCACATCA | 5400 |
| 5401 | CCATTTAAGTAGAAAACAGTATAGTCTTACAACGTGATGTGAATGTAAGGGTTGTGCT | 5460 |
| 5461 | GGTTCGGAGTAGACTGATCTATATCCACCAGTGCAAGGAGACATGGAGGCATATGTGGGCT | 5520 |
| 5521 | AAAAAAAACATCATTAACTGAATCTTTAAAGCACTTCAACATCTGTGTTCATGAA | 5580 |
| 5581 | ATACATAAATGGATTATAGTTATTGAAGCCATTGTGTATATGTTCTTACTTATAAAT | 5640 |
| 5641 | TAGTTTGAAGACAGCAATGTGTTGCCACTTTGATTATTTAATAATTAACTTCTG | 5700 |
| 5701 | ATCTTTCTGAGACAATATGTTCCCTCTTATTCTGTCAATATGAAACCAAGAGCAAAGTT | 5760 |
| 5761 | TCATCCTTAGACATTGAAAGGCTTATTAAATGACCAAATAACATAGTTTAGAGCGAAAGCTT | 5820 |

FIG. 3I

| | | |
|---|---|---|
| 5821 | CCTAATAAATTTATTCTCACTATCTAAAACTAAAACTGAATTCATCTATCTGAT | 5880 |
| 5881 | TATTATATAGTTTCATTTTGTTATTTATTGAATGAGTAAAAATTAATTAAATAC | 5940 |
| 5941 | TTACTATTTTTTCATATAATCTATAAATTAGTACGTGTGGACATCCACTAATAA | 6000 |
| 6001 | CCTATTAATTAAATAGTAATATATTGAAAAATATTTATTGACATGTTTAAATAAAT | 6060 |
| 6061 | CATAATTCTAAAAATAGCAATAACTTTTGAAAACATCAGATTTATGTACGCATAGGA | 6120 |
| 6121 | CACATACCTTTTATTTACTTAAAGGAAAATGAACGAGTCTAAAGCTTCCACATGTTATC | 6180 |
| 6181 | TGAGCAAAACATGGATTTTCTAAATTAGATTCGTTTAAATCAGAACATATTAAGTGAG | 6240 |
| 6241 | TTTCTTAAATTAGATTTTTAATATGTATATACGTAAGAATACTTCTATGTTTAAAAA | 6300 |
| 6301 | AAAAAATAGAATACTTATCTTCCTAAATTTTAAGCCAATATCAATCATTCTAT | 6360 |
| 6361 | AATCCAAGATGAAGAAATCCCTTCAACTCTCGTTAGTTCTTAATTATTCCATCATTC | 6420 |
|      |         M  K  K  S  L  Q  L  S  F  T  F  L  I  I  S  I  I  L | |
| 6421 | TCTCACAAGGTTTGTATTTACATCTTAATATATTGCATATAGTAATTCCATAATAAATTG | 6480 |
|      | S  Q | |
| 6481 | ATTATACTAAAACTTTGACTTTTAAAAATATTGTAAACCCCCATATAATAAATTTATTA | 6540 |

FIG. 3J

| | | |
|---|---|---|
| 6541 | CTATATAAACATAGCATTAAATTATCTCTTTGTGTAAATTCATAACTTTGCAGAAGGG | 6600 |
| 6601 | AAGAAAATATAGAAGAAGTATGGTCAGAAAATGTTGCGTTAATATTGAAAGAATCAACCCTG | 6660 |
| 6661 | AAGTATTTAACTGTTTTTTATACTTTATGCCATTTATAATTTTTAAGTATGGGTTTA | 6720 |
| 6721 | TATATGATGAAGAGCTATTATGATAAATAATATTAAATAGTTTCATTTTATCATCTAT | 6780 |
| 6781 | TTACGAACATTTTGTCTCTGCACATACAAATGATTTAACCGACATTTTCATAATATGGAT | 6840 |
| 6841 | GAACTATAGTTCTTACGTAAATTTATTTGATATTTTAACTAATTTATATATTTTATG | 6900 |
| 6901 | CTTTTTCCAATACATACAGTAGTGTTCTTAAAATATCAAAATTTATCAAAATGTTTAT | 6960 |
| 6961 | TAATATGCACACAATTCTAAAACCATATTTTTCACAAATAAAATATATTCTTTTTTTTTACTA | 7020 |
| 7021 | AACGATATGCTCATTTTTTTTATATACTGGCAAAATATATTTTGCTGATAAATAAATTTCTATTTA | 7080 |
| 7081 | TAACGTTTAAAATGAAACATTTTTGCTGATAAATAAATTTCTATTTCA | 7140 |
| 7141 | TAAAATCTATATATATTTTCTAACAATTAAAAATTTGAAATTTAATATCTTACAGGAATG | 7200 |
| | M | |
| 7201 | ATGGCAGATGCGCAGAAAAAGAATTGTCCCTCGTAAAATTCCAATAAAAGGAAGCTATTGT | 7260 |

FIG. 3K

```
                M  A  D  A  Q  K  K  N  C  P  R  K  I  P  I  K  G  S  Y  C
7261  GCTCCAACTATATGTTTGGATAAGTGTAAGAAGCAACATGGAAGTGTTGGTAGTTGTGCG         7320
       A  P  T  I  C  L  D  K  C  K  K  Q  H  G  T  V  G  S  C  A
7321  GAAGAAAAAGGATTTTGTAACTGCGCCTTGTAAGTAAGAGTTCTCACTAAGTGTAATGAAT       7380
       E  E  K  G  F  C  N  C  A  C  K  STOP
7381  CTAGTAATGTCCAACCAAAGTTTATATTATTCTTTAACATAAGTCTAAATGTTTGT            7440
7441  CTCAGATTTGTGGATCTATTATATATAAATATTAATATGAAGTTAAATAATACAATTG          7500
7501  TATAAACAAGAGTGACTATTAATAAAATATGATCACAGTATTGTTAGAAGTAACCA            7560
7561  ATATTACGTGTAAATCAAAAGCTTAAGACTAGTTAAAAATATAGAGATGAAATCACAAC         7620
7621  CAATATTTAAATGTTATATAATCAACTAACACATGTAATTTTGTACACATGTAAAAAAAA        7680
7681  AAAAAAAAAAAAAGCAAGAGTTGATTAACAAGAGTTAGAAGAAGAGCAACAGA               7740
7741  TCATGCAAGAGCAGTCTAGGTTTGAATGGCTTGACAGATGTTCCAGACATGCCATGA           7800
7801  GGAAGCTTACAAACTCATCAGACACCACAGAAAATTGATAGCATTGTTTCTGAACAT           7860
7861  GACAAAGCTCTCGGTCATGAAGAAGAAATTTCACAGCCAAAGTTTTTGGTAGACCTTCTCTCCA    7920
```

FIG. 3L

```
7921  GCTAGAGAGTTTTGAGACTTCATCCACATTCTCAGTCTCCATTCCATTCTCATGAAGTTTT  7980
7981  CTTTAGGGAAGAGTTATTACAGAAAGCCAAGTTACATGAACCTAACACAATCTATCAAA   8040
8041  GGTAAGAAGAGACGATCAACCAGTATCTTCATCTTCTGTTCCGAAATCACTGTTTGAA    8100
8101  AAGAAACAGTCAATGTCTTACACGAAGATGTGAATGTAAAGTGTGTGCATGTTCGGAT    8160
8161  CCATCTCTGCACCCAGTGAATGATCTATATCTACATGCTCAAGTAACAGGAGAAATATG   8220
8221  TGGGCAAAGAAGTAAAGCTAAAGTAACATGTTTCATTAAATCTTAAAGCATTCAACACCTT 8280
8281  GAGAGTTCTAAAAACACACAAAATACCGATTTATAGATATATAAGCAACTTCTATGTAT   8340
8341  GTTCTTTTACATACGAGTTAGTATGAAGACTCGTCGAATGTGTTGTTGACCATTTTA    8400
8401  TTATTTAATAGTTAACTTCGATGCTTCTAAAATAATATGTTCTTCCAACTCTGTCAA    8460
8461  TATGAAACCAAGAGCAAAGTTTAATTTAGACATGAAACGCCTATTAAATGACCAAATA   8520
8521  ACATAGTTAGACGAAAACTTCCTAATAAAATTTATTCTCACTATCTAAATCTAAAACTG  8580

8581  AATTC  8585
```

FIG. 3M

```
-789  TTTTTTCAAAACGAAACACATATGGAGCCAGNNCTATCACCTCCGCCAGTGCACAAGGATCAACTCCTTAAGCTC
-709  CTTATCTACGACTCATCCTTAGTTATCTATCCTTAACCAAAATATTATTATAAAATTCATAATCATGGTTTAGCTGCTAAG
-629  GACTCCAAGTGCCTCCGTTGCATATGCTCTTATAAACTTAACTTAAGTGCCGCCTAAACGGTGTGTATACCATTTT
-549  CTTTGGAGTTAAGTCACTATCTTCTTCATTTCTTCATCTAGTGTTTCTTTGTGCCGGATACAATGATGTGCCGG
-469  ACTCCCTTGCGAAGTCTGCTCTCCAGAACTAGTAATATAATAATAATAATATTCTTTAGATTTATTATTCAGTTGACAAAA
-389  AAAAGAGTGTTAACCAAAAACTATAATAATAATAATAATATAATAGTCTGTAAATTATCAGTTTGCATG
-309  TGAACTTCTTGAAATACATTCAAGTTTATGTCTATAACTTATTCAGTGACTATAGATTTTCTCTCAGAGTATCT
-229  TTTAAAATCAAAATAGCCAAATTCTCAAAGACATGGAAACCAAACGTAAAATTAGAAAGGAGAAAAATGTTAAGAG
-149  AAACTAAAAACACTTATAATAGGCAGAGGTAAACTCAATGTCCAAATATGGAATGAATAGCCAATGAGAGGAGA
-69   TGCCAAAGAAATCAGAAAAGCAGTCTAAAAATAAAAATAAACCTATAAAAGTCTCAAGCATTTCACACTGAAATCAAA
12    CCCGAAACATAACCAAATAAACATTAATACCCCACAAAAACATGGAGGGTTAACTCACTATTGCCCCG
                                                        M  R  G  V  K  L  L  A  A
92    TGCCTCTACCTGCCGCAGCCGCAACCGTGGTGGTCCATGCCGAAGACCCTTACTTCCACCAGTATGGAAGTGACCTA
       C  L  Y  L  A  A  A  A  T  V  V  V  H  A  E  D  P  Y  F  H  H  V  N  V  T  Y
172   TGGAACCGCTTCCTCTCCTAGGGTTCCACAACAAGTCATTCTAACGCCAATCCTGTCCTACATCAACTCAA
       G  T  A  S  P  L  G  V  P  Q  Q  V  I  L  I  N  G  Q  F  P  G  P  N  I  N  S  T
252   CCTCCAACAACAATGTCATCATCAAGTCTTCAACAACCTGATGAACCCTTCCTCCTCACTGGTAATTATAATACCA
       S  N  N  N  V  I  I  N  V  F  N  N  L  D  E  P  F  L  L  T  W
332   TTCATTCATCTACAAACATACTTTTCTCTAGAAAAAAAAAGAACTCTTTAGCCATGGTCGAATCTAAAATTTAGAAAA
412   CATAAACATAAGGAGTCTGATCATTTACATTATTAATGAATGCATTTTAGAATGAATCCAGCAC
       N  G  I  Q  H
```

FIG. 3N

```
492   AGGAAGAACTGTTGGCAAGATGAACTGCGGGACTATGTGTCGATCATGCCGGCACCAACTACACTTACCATTTCA
      R  K  N  C  W  Q  D  G  T  P  G  T  M  C  P  I  M  P  G  T  N  Y  T  Y  H  F  Q

572   GCCTAAAGATCAGATAGGAAGCTACTTCTACTATCCACCACAGGATCCACCGTCCGCTGTGTGGATATGGTGACTCC
      P  K  D  Q  I  G  S  Y  F  Y  Y  P  T  T  G  M  H  R  A  A  G  G  Y  G  G  L  R

652   GAGTGAACAGCCGTCTCCTCATCCGTCCCTACCGTGTCCGAAGATGACTACTGTCCTCATCGGTGACTGTAC
      V  N  S  R  L  L  I  P  V  P  Y  A  D  P  E  D  D  Y  T  V  L  I  G  D  W  Y

732   ACTAAGAGCCACACCCAGTTGAAGAAGTTCCTGGACGGTGTACTATTGTCGTCAGACGGTATTGTCATCAACGG
      T  K  S  H  T  Q  L  K  K  F  L  D  G  G  R  T  I  G  R  P  D  G  I  V  I  N  G

812   AAAGTCCGAAAAGGTGATGATGACCACCTCTCACCTTGAAGCCTGAAGACTTACAGGGTTAGGATCTGTA
      K  S  G  K  G  D  G  S  D  A  P  L  F  E  T  L  K  P  G  K  T  Y  R  V  R  I  C  N

892   ACGTGGGTGTCAAGACATCTATCAACTTATAGATTCAGAATCACAAGAGATGAGCGTTGAAATGGAAGATCCAGTT
      V  G  V  K  T  S  I  N  F  R  I  Q  N  H  K  M  K  L  V  E  M  E  G  S  H  V

972   CTTCAAAACGATTAGACACTCTTTGAGTTCAGTGGCCAGTGCTTTGCCACCATGTTACCGAATCAGACCTAA
      L  Q  N  D  Y  D  S  L  D  V  E  V  G  Q  C  F  G  T  I  V  T  A  N  Q  E  P  K

1052  AGATTACTACATGGTTGCATCGTCTCGAATTCTGAAGACGGTTATCACAACGGACTTCTCCGCTACGAGGAGCA
      D  Y  Y  M  V  A  S  S  R  E  L  K  T  V  I  T  T  G  L  L  R  Y  E  G  G  K

1132  AAGGACCCGCCTCTTCACAGTTCCGGTCGGATGCCTGGAGTCGGAATGGCCTGGGCTGTGAACAGTTCCGATCCTTCAGTGG
      G  P  A  S  S  Q  L  P  A  G  P  V  G  W  A  W  S  L  N  Q  F  R  S  F  R  W
```

FIG. 30

```
1212  AACTTGACGGCTAGTGCAGCTAGGCCTAACCCTCAGGATCTTACCATTATGAAAGATCAACATCACGGCACAATCAA
      N  L  T  A  S  A  A  R  P  N  P  Q  G  S  Y  H  Y  G  K  I  N  I  T  R  T  I  K

1292  GCTCGTGAACACTCAAGGCAAGGTGCATGGTAACTTAGGTTTGCATTGAACGGAGTCTCCACACAGAACCTGAGACCC
      L  V  N  T  Q  G  K  V  H  G  K  L  R  F  A  L  N  G  V  S  H  T  E  P  E  T  P

1372  CTCTGAAGCTGGCCGAATACTTTGGTATTCCGACAAGGTGTTAAGTATGATACCATCACGATGACCTACCCGGAA
      L  K  L  A  E  Y  F  G  I  S  D  K  V  F  K  Y  D  T  I  T  D  D  P  T  P  E

1452  CAGATCAAAAAACATCAAGTTCGAGCCTAACGTTCTTAACATCACACGTACTTCGTCAGGTGGTGTTTGAGAACCA
      Q  I  K  N  I  K  I  E  P  N  V  L  N  I  T  H  R  T  F  E  V  V  F  E  N  H

1532  CCGAGAAGAGTTCAGTTCAGCAAGTAACTCTTCAINGTACCTAAGTTGACTTTTGACTTTTACTANCTTTTAAAGTTGAGCCAGGACTTG
      E  K  S  V  Q  S  W  H  L  D  G  Y  S  F  F  S  V  A

1612  TTCTTGCATGCAAGTAACTCTTCAINGTACCTAAGTTGACTTTTACTANCTTTTAAAGTTGAGCCAGGACTTG
                                                           V  E  P  G  T  W

1692  ACCCCAGAAGAGGAAGAACTACACCTCTTGATGCAGTGAGACCAGACACAGTTCAGTCTACCAAGTCTGGC
      T  P  E  K  R  K  N  Y  N  L  L  D  A  V  S  R  H  T  V  Q  V  Y  P  K  C  W  A

1772  AGCAATTCTCCACATTGATAACTGTGAATGGAACGTTCGTTCGAGAACAGAGAGAAGGTTACTTAGGACAGC
      A  I  L  L  T  F  D  N  C  G  M  W  N  V  R  S  E  N  T  E  R  R  Y  L  G  Q  Q

1852  AGTTTACGCCAGTCTTGTCTCGAGAAATCACTTAGAGATGAATACAACATGCCTGACACAAGCCTCCAATGTGGTC
      F  T  P  V  S  C  L  Q  R  N  H  L  E  M  N  T  T  C  L  R  Q  A  S  N  V  V
```

FIG. 3P

```
1932  TCGTCAAAACACACCTAACCGTTAACCCTGTTAGCGTCGTGCCTAAGTTAACTTTTAATACAACTAAAGAGTNTGA
         S  S  K  T  H  L  N  L  L  T  L  T  L  V  P  K  F  N  F  *
2012  NTCTTCTGTTGATNTGAAATTAATTNCTAAATTATATGGTTACTCGTATATCATGAANTGAAATGTATGTATGT
2092  GTCTATACCTTTTAAGTAATTTTTCTTTCTTCAAGAAGCATTAGTCTTCTCTTGTTTTTGTCTTCACTTTTTGTA
2172  ACAATTATGTAATGTATTATCCGATAATCTTCGATGAATAAGCAAGATCTTATTCTCCAAAAAAAAACT
2252  TTACAATAAAGTATTTCTATAGCCTAGAACCATGTATGATATAAACAAACCTCTCTTCTAGTCTGAGCCTTTTTC
2332  TAAGGCTCTTTATCCTGGTCTTCCACCAACGNTTCCTTGAGAGAAGTCATCGAGCTATCATCATTCTCTGT
2412  ATCGACCTGAACAACTCTTGAACATCCCATTACTTGAATCATAGTGTTGGTCTTTTGAAGGTCGATGGTCCAGACACT
2492  GAGACCGCAATCTTCAAGTAATGAAAACAGCTCAAGTGCCAGATTTCTCAGTTATCAGTCCGAATCAAGAATCTCAGCT
2572  CCCTCTACTCTCCTATAAAGCTGTTTAGCCACCGAGATTGTTGTCCTCACCTTCTGATCGATCGGTTT
2652  CTTCCCCACACAACCTCCACAACTATAACCCCTAGCTATACACACCTTCTTGGTCCTCCACCTGAAACTCTGTAAT
2732  ACTCTGGCGAAGTCCGAGACCGTACCGGAGTTCCCGGAGGGTGTCACGCTCAAATGGGTGTCCAGAGCGTCACCAGCCTTGCCA
2812  TACCGAAGTCCGAGACCGGTGCTGTGAAGTCTTGGTCTAGA  2852
```

FIG. 3Q

```
  1  GAATCCTCAACANNIGATTCTCATCAACGACAGTTCCCTGTCCTAACCTAAACTCCACATCCACAACAATGTGTC
        I P Q X X I L I N G Q F P G P N L N S T S N N N V V

81  ATCAATGTTTCAACAACCTTGACGAGCCTTCCCTCTGACCTGTTAGTCACCATTCCTCTCATTTTATAGGCATCT
        I N V F N N L D E P F L L T W

161  GTTCTAAAATTTAAAGTAAATGATATTTAAAGCTACACAATTTTTTTCATTTTAATATAACTGTCTTTACAAGGCCAAA
241  CGAGAAATGCAAATGGAAAGTCTCATTGTTGATATTTACAGTTGACATATGATTTGATTTTTTCAGATCTT
321  TGTAGGTTTGTTGAAAAAAGTTTGGTATAGTTATGTAGTCTTAGGTTGAATAATTCATAACCA
401  AATTGAAAACAAAACTTTGATCGTTAATCAAATCTCTCTATTTTTAAAGTTATATTCACATAATTAC
481  ATCTATATATAATATATATAATATAAAATGATAATTCAGTTATCTAATATATAAATCAGACTAAATATAAAAC
561  AAAAAGAAATTTAAACACATTTGACTCAGTTTAGATTAAGATTGTTATATTACCAAGTAATTATGCTAGTCTTCA
641  TTGCAAATTTAAACACATTTAACTATGTCGGTTCGGTCAGCAGGAGTGTCCAGCAGGAGAACTCATGGC
                                        S G L Q H R K N S W Q

721  AAGATGGTGACCCGAACCTCATGCCCAATCCAGCAGGCACCAACTACACTTACCATTTCCAGCCTAAGGACCAGATC
        D G V T G T S C P I P A G T N Y T Y H F Q P K D Q I

801  GGTAGCTACTTCTACTACCATCAACCCTCGACCGTTCTCCGGGTTCGGAGGCCTCGGTCAACAGCGCGTCT
        G S Y F Y Y P S T A L H R F S G G F G G G L R V N S R L

881  CCTCATCCCNTCCCTTACGCTGACCCGAAGATGACCACCATCCATCAAGACGTACACCAAGAGCCACCG
        L I P X P Y A D P E D D H T I L I N D W Y T K S H T A

961  CTCTCAAGACCTTCCTTGACAGCGGCCACTCTTGGTCCCTGACGGTCCTCATCAACGAAAGTCCGTAAAGTC
        L K T F L D S G R T L G S P D G V L I N G K S G K V
```

FIG. 3R

```
1041  GGAGGACAAAACAAGCCTCTCTTCACCATGAAGCCAGAAAGACTTACAGTACAGAATCTGTAACGTTGGTTCAAATC
       G  G  Q  N  K  P  L  F  T  M  K  P  G  K  T  Y  K  Y  R  I  C  N  V  G  F  K  S

1121  CACTCTTAACTTCAGGATCCAAGGACACAAGATGAAGCTTGTTGAGATGGAAGGATCTCAGTTCCAGAAGACTACG
       T  L  N  F  R  I  Q  G  H  K  M  K  L  V  E  M  E  G  S  H  V  L  Q  N  D  Y  D

1201  ACTCGCTGACGTCGACAGTCGGACAGTCGCGTTCGTGACGCTGACCAAGAGCCAAGAGCTACTACATGTT
       S  L  D  V  H  V  G  Q  S  F  A  V  L  V  T  A  D  Q  E  A  K  S  Y  Y  M  V

1281  GCATCCACTAGTTCCTCAAGAAGGAAGTGAGCACTGTTGGGTGATGAGCTACGAAGGAAGCAATGTTCAGCCTCAAA
       A  S  T  R  F  L  K  K  E  V  S  T  V  G  V  M  S  Y  E  G  S  N  V  Q  P  S  N

1361  TGTGCTTCCCAAGGCTTGGATGGCTTGGAGTTCAGTTGGTCTCTTAACCAGTTCAGATCATTCGAGATGGAACTTAACCGCCAGG
       V  L  P  K  A  P  V  G  W  A  W  S  L  N  Q  F  R  S  F  R  W  N  L  T  A  S  A

1441  CGGCTAGCCCTAACCCGCAAGGATCTTACCATTACGGAAAGATCAACATCACAGTACCATCAAGCTGCCAACACCAAG
       A  R  P  N  P  Q  G  S  Y  H  Y  G  K  I  N  I  T  R  T  I  K  L  A  N  T  K

1521  AACTTGGTGGACGGTAAGGTCAGTTTGGCCTTAACGGTGATCAGGTTGACACCGTTGATCACTCCTTGAAGCTTGCTGA
       N  L  V  D  G  K  V  R  F  G  L  N  G  V  S  H  V  D  T  X  T  P  L  K  L  A  E

1601  GTACTTCNAGATGTCCGAGAAGGTCTTCAAATACAATGTCATCAAGGACGAACCAGCAGCCAAGATCACTACTAACCG
       Y  F  X  M  S  E  K  V  F  K  Y  N  V  I  K  D  E  P  A  A  K  I  T  T  L  T  V
```

FIG. 3S

```
1681  TTGAGCCTAATGTCCTAACATCACTTCCGTACTTGTTGAAATGTCTTCGAGAACCAGAGAGACATGCAATCA
       E  P  N  V  L  N  I  T  F  R  T  F  V  E  I  V  F  E  E  N  H  E  K  S  M  Q  S

1761  TTCCATTTGGATGGTTACTCCTTCTTCTCAGTCGGTAAGCTTCATTAATAACTCTATAGGCCAATGTTCACTTANTAN
       F  H  L  D  G  Y  S  F  F  S  V  A

1841  GCGCAGAACCGGGGTGATCTTTTACTTCAGATATAAGATTCCTAACACAATTTTTTAATATTTTTCACAGTTCTGACC
                                                                                S  E  P

1921  AGGAACATGGACACCAGAGAAGAGAACACTACAACTGCTCGATGCGGTCAGCAGACACACCGTCAAGTNTCCCCA
       G  T  W  T  P  E  K  R  N  N  Y  N  L  L  D  A  V  S  R  H  T  V  Q  V  F  P  K

2001  AGTCGTGGTCCGCCATCCTCTGACATTGACAACGCCGTATGTGGAACATCAGATCAGAGAACTGGAGAGAAGATAC
       S  W  S  A  I  L  L  T  F  D  N  A  G  M  W  N  I  R  S  E  N  W  E  R  R  Y

2081  TTGGGACAGCAAATGTACGTCAGTTGTCTTCCCTGAGAAATCACTAAGACGAATACAACATCCACTCAACACCAA
       L  G  Q  Q  M  Y  V  S  V  L  S  P  E  K  S  L  R  D  E  Y  N  I  P  L  N  T  N

2161  CCTTTGTGGTATGTTAAGGCTTGCCATTACCTACACCTACACTATTTAATTAACTCACTTCACAAAGTTTATT
       L  C  G  I  V  K  G  L  P  L  P  T  P  Y  T  I  *

2241  TATTTATTTGATATATGTAAAATTCACTTTTTACAAGTGAGTGTATTACGTTGACTAATTAACCCTTTCCTAATTCATT
```

FIG. 3T

```
2321  TAACATACTACTACTATAATTACAGATCCAGTTGTTGTTTCACTAATAGTAATATACACATTAGCTTACTTAATAT
2401  AATCCTGATTCTAACACAAAGACTGTTATTCATTTCATAATGACAAAACTGTTCACCCTATGTGAACCCTCTAA
2481  TTCACCTCTATTCTTAACACCAAATCACAAGTAAGATTAATAAAAAAGAATAAATTAAAGAATAAAAAATAG
2561  GTTTCCTAAAAAGGGTTTATTTGTCAATAACCAAAAAAAATGAAAATTANATTTTGGAGAGAGTAGAGAGAT
2641  AGGAANAAAGTAGGAGAGAGAATTTAGTTAGTTAGTGTATTTAAGTTTTTTCATGTATATAGGGTGCAATT
2721  TCCAAAAAAAAGTCGGTTAACAGAGAAATAACGTGGTTTGTACCCGTCCATCGAGTCTCTTCTTTTATA
2801  GCCCAGAGAAGATAGAAGCTCAGTTCCTCCAGTTCGTCTCCAAATCAAATTCGATTTCATCTTCCAAATCAAATC
2881  AAGCCATGTGCCTTATGAGTAGAAAGAGCCTGAGAAGATGAAGAGATGATGGATTCAAACTTGCAGGCCC
2961  CAGGGAGGAGAGAGATGACTTTACTGTGAACCAGNCTGTGCCTAAAATTCAACAAAAGAAACGATGCAATTGGAAAT
3041  CAGACACTACAACTTGNTTAAAATAAAAACGCTANTTGTAAATATGACTTCAAGTTGATGAGAACTC
3121  ACTGATGCAAGTCGTGATCTTTGATGTAAGGTCACACAGACTTTTAATGTATTCTTAAATATAGATTTGC
3201  AAGTTCTTTGTTGTATTCTTCTTCTTCGTGGGACATCTGACCTGTAAATCAGAGATATAATCCACCAAACCCAAGGTT
3281  TCCTGGTTTAATT   3293
```

FIG. 3U

```
-2022  GGATCCGTTCCTTCCGGTCATTTCTCTCCGTCATAGGAGAACATCGATCATGATCACTCGATCAAACTAGCCT
-1942  TTCTCTTATTATTCATCACCACACAGACCAACCCTGCCCCAAGCCAGCAAGCGACTACCTTTCACGCGCATCA
-1862  AAGCAGTCGCGAATATGCACTGTTGTCCTAACAACACAAGTCCATGCTGTAAACCCTTAAACACGTTCCTACGAT
-1782  GACCCTATCGATTGATCGAGCGGTTAGCGGCTGGACTGAATCTCTGTGAAAGAGTGTGTTTCCTCTCCGAGAT
-1702  CAAACCAAAACACAAATCAAAGCAACCGCAGCTCGAGTGGTCAACAGCTGCGAAAAAACTGAGTACGATTAGAAG
-1622  ATTTCACTGATTTTGAACGTATGCGGAAGAGTAAAGAGTGCCTCATAACTATTCAGTGTAAGAAGAAGTTA
-1542  ATGTCGATCATGGGTACCATTGTTTGGATGATATTGATGATATTAGAGAATCTGTTGAAGGAANTGGAGACTGGAT
-1462  TAGTGTTGGAAGAATCTAAGCAGTAATACGACACTTCGCCCCAACCACCATTGTTAATGTTTGAAACTATTTTAAGACGTTGTATCA
-1382  AGGTGAAACTTAAGGAAGACACTCGTATAGTCCTAAAGCCTATATGTGACCATATAGGATGTAGTGTCTAGGTTTATACATGT
-1302  GTAATAAATAATCACTGAGATGATGATGGAAAGGATATTAATGTGATTACNATAATTATTTGATAACTGACAAATATCNICCAATCAA
-1222  ACGGATGGATTCGAGAGTATATAGTGATTACNATAATTATTTGATAACTGACAAATATCNICCAATCAA
-1142  ATGAAGCTGAAAGTATATAGTGATTACNATAATTATTTGATAACTGACAAATATCNICCAATCAA
-1062  TTATTGTTAAATGTTTTCGGATACATGTCCAGTCACAAATAATGTGCATTTTCATATATTGATGCATGAA
-982   GTTTCATATATTGATGAGATGAAACATACATTGTTCCTGTGTCAACATTCACGCCGATGTTCTTTAT
-902   AATCAACTACATACTGATCTAGATGATGATGAGTACCATGCATGAATACGAGTGAATAACATTCCTATGTATAGT
-822   CAAGGCGATGTTAAAATGTACCCCGCTTTCTCGTGTAGTAATATATAGGACATAATTATATTTCTCAAATGAATTTGAGTTTTGAGTG
-742   ATAGTAGTTCATTTGTTGACCAAAATTAAATATACAACATGCTCGGGTCAACCCCCCAGTATTATCGTTATAAAAATAC
-662   CCTCCTGAAAAGATGATTCCAGCTTTCAATTTTACAATGCGCATGAAGCTAAAACTGGTAATAGTCTAAAGAGTCATGAATGAATAATAC
-582   TCAGAATAATCCACACCTAAAACTGCCATGAACAACCATAGATGACACTATTATACACTTATTAGAGAACTCGATGAACTGAACTGAATGATAATAC
-502   CATTCATGTTGAGTAACACCATGAGATGATGACACAATTCTTACTACCAGAAACTCGATGAGAACTTAGAGACACAATTGTCTTGTTACATG
-422   TTGTAGTCCGATTAATTGGGTTTGAAGGAAGAATTTAGAAGATGAGACTTTAGAAACATTTAGAACATGCATTACTTCGTT
-342   ACTTTCGAAATTCGATGTAAAACTAGTACTAAACTTTCCATCCTAAGTTACTTCTTATTTTAGTAATGAGCTACACCTCTGATCA
-262   TAATAAATTATAATAGACTAACTTTCCATCCTAAGTTACTTCTTATTTTAGTAATGAGCTACACCTCTGATCA
-182   GGACAAAGACATAATCATCTCTGTGGGTGAATAATTTTAATCTCAAATCCAATATTTGATTAGAGAAGTTCAGCC
```

FIG. 3V

```
-102  ATTCAACTACTACCTAAAAATGTCTCCCTCCATCCAAAGCTCATTGGAACCTAATTTTAGAAACTACAACTTCTATAAGAATCT
 -22  CCCATAATGCACCATAATCTCCACCAGCCCCCATTAAATATCCACCGGTCTGAATAATAAAAATAAGTCCCTCCCT
  59  CTCCTATTTACCTCTAAATAAACCTGAGGGAGAAAAACAAAAACAAAAATAGATTAAAATAAATAATG
                                                                        M
 139  GCGGTCGGGAAAATTGTGATATCAGTGGCATCCATGCTCTAGTGGTCGGTGTTGCCATAGGAGTGTCACCTTTGTTAA
      A  V  G  K  I  V  I  S  V  A  S  M  L  L  V  V  G  V  A  I  G  V  V  T  F  V  N
 219  TAAGGTGGGTCGCAGTGGCCACAAGACTCGAACTCGATCAGAAAGCGGTTGAGTCACTTGTGGTCAGCCACAG
      K  G  G  G  A  G  G  G  D  K  T  L  N  S  H  Q  K  A  V  E  S  L  C  A  S  A  T  D
 299  ACAAAGGTTCATGCCAAAAAACACTTGACCCAGTCAAAAGGCGACATCCAGTAAACTTATCCAAGCCTTCAAGTTTAGCT
      K  G  S  C  A  K  T  L  D  P  V  K  S  D  D  P  S  K  L  I  K  A  F  M  L  A
 379  ACAAAGATGCTGTCACAAATCACACAACTTCACGCTTCAACGAAGAAGTATGGGAAAAACATTAACGGACGAG
      T  K  D  A  V  T  K  S  T  N  E  F  T  A  S  T  E  E  G  M  G  K  N  I  N  A  T  S
 459  CAAAGCCGTTCTGATTACTCGAAGAGAGTCCTGATGTACTGCTCGAGAATCTTGAGGACCATTGTGAAGAATGGGTG
      K  A  V  L  D  Y  C  K  R  V  L  M  Y  A  L  E  D  L  E  T  I  V  E  E  M  G  E
 539  AAGATCTTCAGCAGAGTTGGAGTTAGAATGGACCAGCTTAACAATGTTAACCGAGTTTTAATTACCAAACCGATTGT
      D  L  Q  Q  S  G  S  K  M  D  Q  L  K  Q  W  L  T  G  V  F  N  Y  Q  T  D  C
 619  ATTGATCGATATTGAGAATGGAACTAAGAAAGTCATGGGCGAAGGAATCGCTCACTCCAAGATTTGTCCAGTAACGC
      I  D  D  I  E  E  S  E  L  R  K  V  M  G  E  G  I  A  H  S  K  I  L  S  S  N  A
```

FIG. 3W

```
699   TATGGATATCTTCCATGCTCTAACCACCGCAAGTCCAAATGAAGTTAAGTCGATGACATGAAGAAAGGAACCTCG
       I  D  I  F  H  A  L  T  T  A  M  S  Q  M  N  V  K  V  D  D  M  K  K  G  N  L  G

779   GAGAAACTCCAGCTCCTGATCGTGATCTTCTGAAGACTTGGACCAAAAAGGATTACCTAAATGGCATTCTGACAAGAC
       E  T  P  A  P  D  R  D  L  L  E  D  L  D  Q  K  G  L  P  K  W  H  S  D  K  D

859   AGGAAGCTTATGCTCAGGCCCGACCCCTGGTCACTCTGATGAAGTATCGGTGAAGCCCGGTGTGGCCGTAA
       R  K  L  M  A  Q  A  G  R  P  G  A  P  A  D  E  G  I  G  E  G  G  G  G  K

939   GATCAAGCCGACTCATGTGGCTAAGGACGGAAGTGACAGTTAAGACGATTCTGAGGCGGTTAAAGCTTGTCCG
       I  K  P  T  H  V  V  A  K  D  G  S  G  Q  F  K  T  I  S  E  A  V  K  A  C  P  E

1019  AGAAAAATCCTGAGCGTTGCATTATCTATATTAAGGCTGGCGTGTCTACAAGGACAGTCACTATCCTAAGAAGTAAAC
       K  N  P  G  R  C  I  I  Y  I  K  A  G  V  Y  K  E  Q  V  T  I  P  K  K  V  N

1099  AAGTTTCATGTTGGTGATGGTGCAACACAGACAATCATTACTTTTGACAGAAGTGTGCTTAGCCCTGGAACCAC
       N  V  F  M  F  G  D  G  A  T  Q  T  I  I  T  F  D  R  S  V  G  L  S  P  G  T  T

1179  TACTTCACTCAGTGGCACCGTTCGTAAGTCATTCATTAATTAATCTGTCTTTAATTTTCCTATCTAAACTAAATTGCAC
       T  S  L  S  G  T  V  Q

1259  CGTCCAATATCTAAATAATACGTTGGTATCTAAATATACAGCGTTGATATCTAATCATATACATGCATGCATGCAG

1339  AGTTGAATCTGAGGATTCATGGCGAAATGGATTCAGAACACTGCTGTCCATTAGGACACCAAGCTGTCCG
       V  E  S  E  G  F  M  A  K  W  I  G  F  Q  N  T  A  G  P  L  G  H  Q  A  V  A
```

FIG. 3X

```
1419  TTCCGTGTGAACGGAGACCGTCGGGTCATATTCAACTGCAGATTGACGGTTACCAAGACACGTCTAGTGTCGACAACGG
      F  R  V  N  G  D  R  A  V  I  F  N  C  R  F  D  G  Y  Q  D  T  L  Y  V  N  N  G

1499  ACGTCAGTTCTACAGGAACATTGTGTATCCGGTACAGTGTGGATTCATCTTCGAAAATCGGACCGTGATTCAAAACT
      R  Q  F  Y  R  N  I  V  V  S  G  T  V  D  F  I  F  G  K  S  A  T  V  I  Q  N  S

1579  CTCTAATCCTCTGCGAAAGGGAAGCCCCGACAAACCAACCAGTCACAGCCGACGGTAACGAGAAGGTAAAGCGGTG
      L  I  L  C  R  K  G  S  P  G  Q  T  N  H  V  T  A  D  G  N  E  K  G  K  A  V

1659  AAGATTGGTATCGTTCTCCATAACTGCCGTATCATGGCGGACAAAGAGCTGGAAGCTGACAGGCTAACGTCAAATCATA
      K  I  G  I  V  L  H  N  C  R  I  M  A  D  K  E  L  E  A  D  R  L  T  V  K  S  Y

1739  CCTTGGACGGGCCGTTGGAAACCATTTGCCACCACCGCAGTTATCGGAACTGAGATTGGCGATTGATTCAACGACGAGGAT
      L  G  R  P  W  K  P  F  A  T  T  A  V  I  G  T  E  I  G  D  L  I  Q  P  T  G  W

1819  GGAACGAATGCCAAGGAGAATAACCGTTCTTGGATTATAAGAAACTAACAAATATAACGAATA
      N  E  W  Q  G  E  K  F  H  L  T  A  T  Y  V  E  E  F  N  N  R  G  P  G  A  N  T

1899  GCTGGCAGGGTTCCTTGGCTAAGATGGCTAAGTCTGCTGCTGAAGTTGAACGTTCACCGTCGCTAACTGGTTGACTCC
      A  A  R  V  P  W  A  K  M  A  K  S  A  A  E  V  E  R  E  F  T  V  A  N  W  L  T  P

1979  TGCTAACTGGATTCAAGAAGCCAACGTTCCGTCCAGCTTGGATTATAAGAAACTAACAAATATAACGAATA
      A  N  W  I  Q  E  A  N  V  P  V  Q  L  G  L  *

2059  ATATATAGTTAATGTGATTCATGTAAAAAAGGTAACGATACGACCTTCGTCTCTCGGATCAGGCCTCTTTTTGGTTATTATTAG
```

FIG. 3Y

```
2139  GGTTCTAGGGGTTTGGGATGATGTTGTATAAGATTGCTTTGTTGTTTCACATGCAAAACATATATACAAAATATCTTATT
2219  TCTTCTTTACTTCTTTTATCAAATAATGAGTTTTTATAACCATGTTGATCTCTATATTAGACATCCTATCCCTA
2299  AACATGATAAATAACTTCAAACTAATACCTAGTAAAATAATATAAACAAAAAATACTTAGTAAGATTAGTGCAA
2379  GCATGGCTCAACAAATATACTTTATAAAAGTTGCATTATTGCTATGTTTATATAGATTGCTATATGTAAGTATGTT
2459  GATAGAAGTTTATGAGGACAGAGATGACTATTGCAAATATTAAGAGAAGTGATATGTTATCATTTATCAAACAAA
2539  GCAAGCCCTATATTACCAAATCAATCAAATCACTCAAAGCGAAGCTGCCCATGATGATCTTCACCAATATTCACACATTA
2619  CAAACGTGACATTACTTCTCTCTTCTATGGCGTGTTCCTTAACCAAAGTAAACAGAGTCCAAATCCAACTTCCAAACCAA
2699  CCCCATTCATCTTATTGGATCGTCCTTGATCGATAACATTCCGTTTAAGATGTTCCAAGGACAATACATCTCTT
2779  TACCCATGGACCTGATCGTCTAGTAGAGTCATAAAGATCCATCGGCTAAAGCATGTCCTTACTATCAATGTTAA
2859  AGATCCTAAGGTGCTCCTATTGATGAGCAACAAGTTCCCTAGACGCCCTAATCGGACTATGTGTCAAGATTCACTGG
2939  ACCGGGTTAGGTTGAC  2955
```

FIG. 4

```
Bp4C  AAAAAAAAATAGAATACTTTATCTCTTCCTAAATTTTTAAGCCAATATCAATCCATTTCTATAATCCAAGATGAAGAAATCCCTTCAACTCTCGTTTA  100
Bp4A    T                                                             T                              T
cBp401            C                                        *                      T   A
cBp405                                                                     T   A            A

Bp4C  CGTTCTTAATTATCCTCCAATCATTCTCACAAGGAATGATTCTCACAAGGAATGCGCAGAAAAAGAATTGTCCTAAAATTCAATAAAAGGAACTATTGTCC  200
Bp4A                                                         A
cBp401                       T                               A                T
cBp405                                *                                          C                   AT
cBp408

Bp4C  TCCAACTATATGTTTGGATAAGTGTAAGAAGCAACATGGAACTGTTGGTAGTTGTGCGGAAGAAAAAGGATTTGTAACTGCGCTTGTAAGTAAGAGTTC  300
Bp4A                T                                          TAA  TGA                              G
cBp401                                                                                               A
cBp405           A                          C        T                                               A
cBp408

Bp4C  TCACTAAGTGTAATGAATCTAGTAATGTCCAACCAAAGTTTTATATTATTCTTTTAACAATAAGTCTAAATGTTTGTCTCAGATTTGTGGATCTATTTA  400
Bp4A                T
cBp401                                                                                  T TT
cBp405                                                                                  T TT
cBp408                                                                                    T

Bp4C  TAATAAATAATAATATGAATGTTAAAT  427
Bp4A      T
cBp401                              polyA
cBp405             T           C    polyA
cBp408                              polyA
```

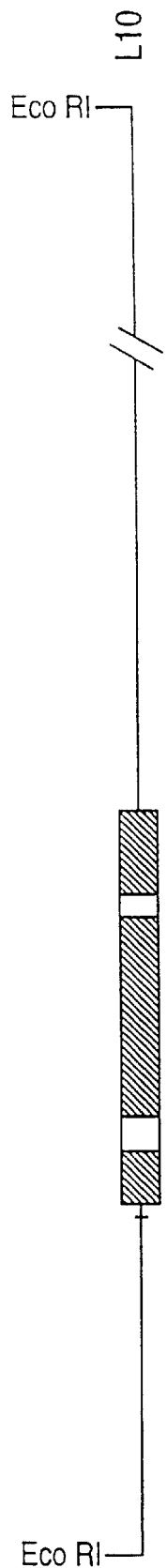
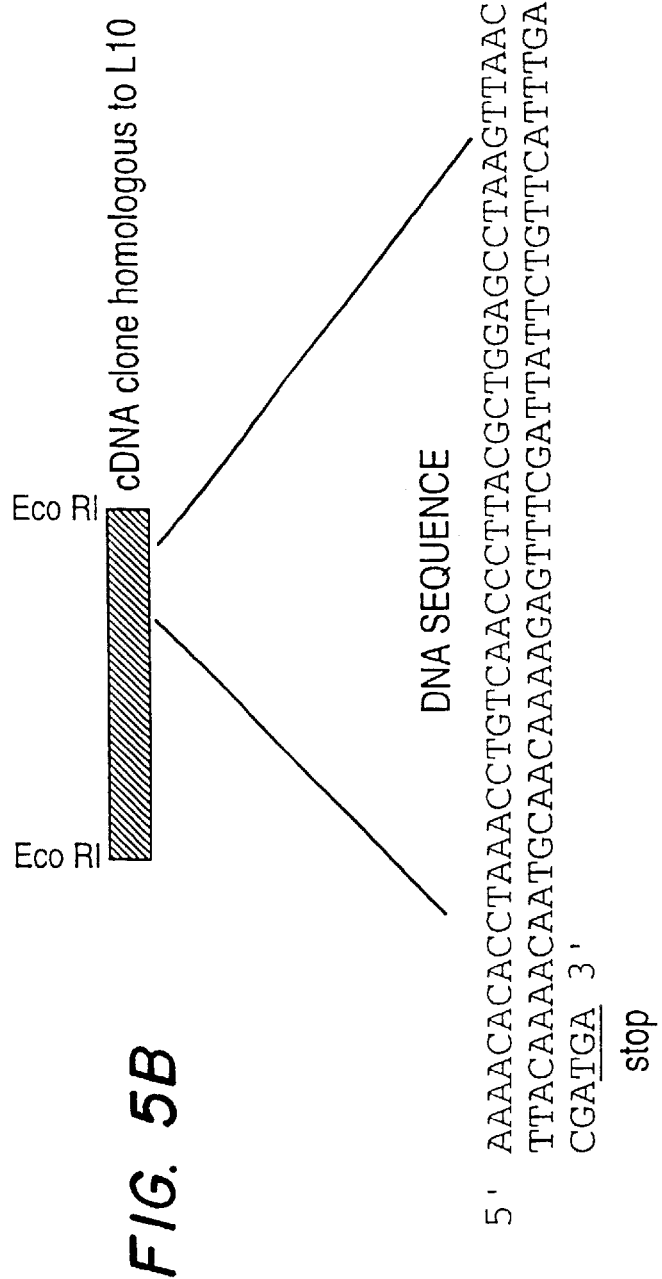
FIG. 5A
FIG. 5B
DNA SEQUENCE
5' AAAACACACCTAAACCTGTCAACCCTTACGCTGGAGCCTAAGTTAACT
TTACAAAACAATGCAACACAAAAGAGTTTCGATTATTCTGTTCATTTGAT
CGATGA 3'
      stop

FIG. 6

Eco RV

GGAAAATGTGATATCAGTGGCATCCATGCTTCTAGTGGTGGGTGTTCCATAGAGTTGTCACTTTGTTAATAAGG
TGGTGGTGCAGTGGCGGAGACTCTGAACTCGCATGAGAAAGCGGTTGAGTCACTTTGTGGTCAGCAGACAAAGT
TCATGCGCAAAAACACTTGACCCAGTCAAAGGATCCAAGTAAACTTATCAAAGCCTTCATGTTAGTACAAAGATG
CTGTCACAAAATCACAAACTTCACGGCTTCACGGAGAAGGTATGGGAAAATTAAGGAGAGAAGCAAGCCGTTCT
TGATTACTGCAAGAGAGTCTGAATGTACGGCTTCGAGGATCTTGAGAGACCATTGTTGAAGAAATGGGTGAAGATCTTCAG
CAGAGTGGAGTAAGATGGACCAGCTTAAACAATGTTAACCGGAGTTTTAATTACCAAACCGATTGATTGATGATA
TTGAAGAATCGAACTAAGAAAAGTCATGGCGAAGGAATCGCTCACCCAGATTTGTCCAGTAACCTATCGATAT
CTTCCATGCTCTAACCACCGCCAATGTCCAAATGAATGTTAAGGTCGATGACATGAAGAAGGAACTCGAGAAACT
CCAGTCCTCGATGTGATTCTTGAAGACTTGGACCAAAAAGAATTACCTAAATGGCATTCTGACAAGCAGGAAGC
TTATGGCTCAGCCGACGCCCTGTGATGAAGCCTGATGAAGGGATATCGGTGAAGGCCGCGGTGTGCCGTAAGATCAA
GCCGACTCATGGTGGCCTAAGGACGGAAGTTAAGACGACAGTTAAGACGATTCTGAGGCGGGTTAAGCTTGTCCGAGAAA
AATCCTGGACGTTCATTATCTATTATTNAGGCTGGTGTCTACAAGAGACAATACTATACTTTGACGAAGTGTGGTCTTAGCCCTGAAACCACTAC
TTTTCATGTTTGGTGATGGTCAACACAGACATATACTTTGACAGAGAAGTGTCGCTTAGCCCTGAACCACTAC
TTCACTCAGTGCGAGGTTCGTAAGCTCATTTATTAATTAATTCTGTCTTTAATTTTCCTATCTAACTAAATTGCACG
TGCAATATCTAAATATACGTTGGTATCTAAATAACAGTGCACGTTGATATCTAAATATATACATGGATGCAGA
GGTTGAATCTAGCCGATTCATGGCCGAAATGGATCGGGTTCGAACACTGCTGTCCATTGAGACACGCCTAGGTGAACAACG
TTCCGTGTGTAACGGAGACGGTGCGGTCATAATTGTACGGAGATTTGACGGGTTACCAGACACGCCTCTAGTGACAACG
GAGTCCAGTTCTACGAGGAACATTGTGTATCCGGTACAGTTCGATTCTATCTCCAGATCTGGACCGTGATTCAAA
CTCTCTAATCCTGCCGAAGGGAAGCCCCGACAAACCAGTCACAGCCGACGGTAACGCAGGTAACGAGAAGGTAAGCG
GTGAAGATTCGTAGCGATGCGTCTCCCATAACTGCCGTATCATGCCGGACAAAGAGCTCGAAGCTCGAAGCGTACCGTCAAT
CATTACCTTGACGGCCGTGGAAACCATTTGCCACCGCCAGTTATCGGAACTGAGATTGGCGATTGATTCAACCGAC
AGGATGGAACGAATGCAAGGAGGAGAAAAATTCCATTTGACAGCTACAGTGTAGTTCAATAACGTGACCAGGAGCT
AACACTCTGCAGGGTTCCTTGGCTAAGATGCTAAGTCTGCTGAGGTTGAACGTTTCACCGTGCCGTAACTTGT
TGACTCCGCTACTGGATTGAAGAGCCAAGTTCCTGTCCAGCTTGATTATAAGAAAACTAACTAACTAAAATATAT
AACGAATAATAATATAGTATGTGAAAAAAAAAAAAAA

FIG. 17

HYBRID SEED PRODUCTION USING BINARY CRYPTOCYTOTOXICITY

| LINE A PLANT | LINE A PLANT |
|---|---|
| INTEGRATE GENE 1 | INTEGRATE GENE 2 |

 GENE 1      GENE 2

RECOVER TRANSFORMANT WITH GENE 1 ON CHROMOSOME Z     RECOVER TRANSFORMANT WITH GENE 2 ON CHROMOSOME Z

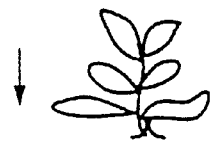     

CONVERSION TO HOMOZYGOUS LINES BY SELFING AND SELECTION FOR THE INSERTED GENES BY CHEMICAL RESISTANCE PHENOTYPE OR GENOTYPE

MAINTAIN BY SELFING IN ISOLATION     MAINTAIN BY SELFING IN ISOLATION

     

MALE FERTILE ISOGENIC LINE A1     MALE FERTILE ISOGENIC LINE A2

FIG. 18

SEGREGATION OF BINARY CRYPTOCYTOTOXICITY GENES IF BOTH GENES ARE LOCATED ON THE SAME CHROMOSOME OF A CHROMOSOME PAIR IN THE ISOGENIC MALE STERILE LINE

PREPRODUCTION OF MALE STERILE LINE     IAMS | IAMS   X   IAMH | IAMH

HYBRID SEED PRODUCTION     IAMS | IAMH   X   ||

F1 SELFING, CROSS-POLLINATION BETWEEN PLANTS     IAMS |   X   | IAMH

F2 POTENTIAL GENOTYPES
SELF     IAMS ||   IAMS | IAMS (2)   IAMS ||

16 POTENTIAL GENOTYPES, 2 OF THOSE (12.5%) ARE MALE STERILE

SELF     IAMH | IAMH     ||     | IAMH (2)

CROSS     IAMS | IAMH     ||     | IAMH (2)
            MS

CROSS     IAMS | IAMS (2)     | IAMH     ||
                              MS

FIG. 19
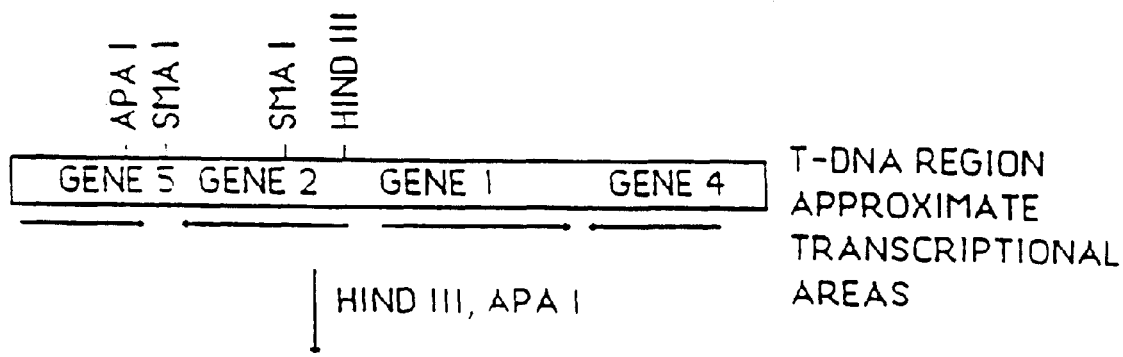
T-DNA REGION
APPROXIMATE TRANSCRIPTIONAL AREAS
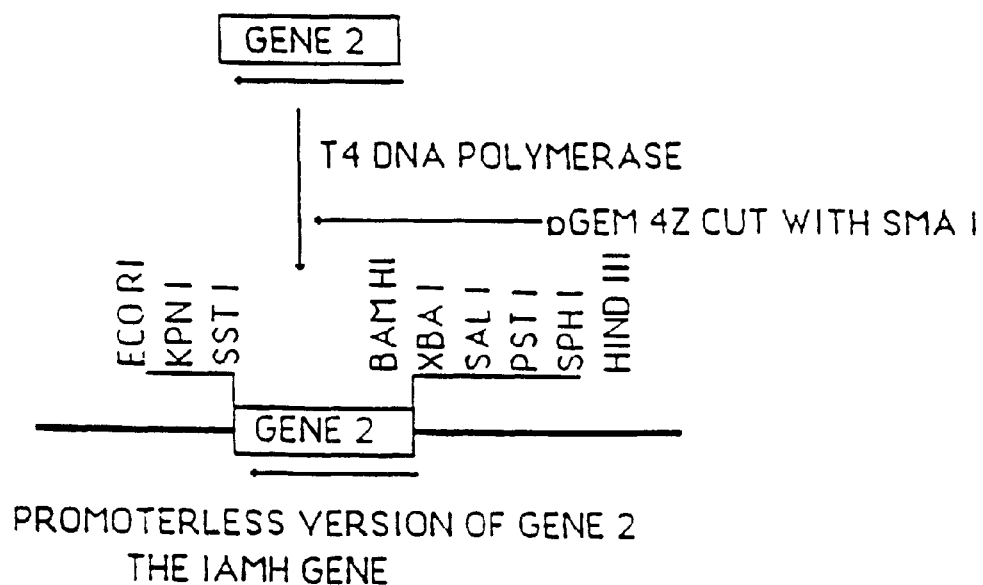
PROMOTERLESS VERSION OF GENE 2
THE IAMH GENE

MOLECULAR METHODS OF HYBRID SEED PRODUCTION

This application is a divisional of application Ser. No. 08/897,325 filed Jul. 21, 1997, now Abandoned, which is a divisional of application Ser. No. 08/276,510 filed Jul. 14, 1994, which is a continuation of application Ser. No. 07/556,917 filed Jul. 20, 1990, now Abandoned, which is a 371 of PCT/CA90/00037 filed Feb. 2, 1990, which is a continuation-in-part of application Ser. No. 07/306,438 filed Feb. 3, 1989, now Abandoned, which is a continuation-in-part of application Ser. No. 07/151,906 filed Feb. 3, 1988, now Abandoned.

TECHNICAL FIELD

The present invention relates to a method for producing male sterile plants and hybrid seed, to genetic material used to impart the male sterility trait and to new products produced by said method, namely, genetically transformed plants carrying the male sterile trait, male sterile plants and hybrid seed produced by pollinating said plants with pollen from male fertile plants.

BACKGROUND ART

Production of hybrid seed for commercial sale is a large industry. Hybrid plants grown from hybrid seed benefit from the heterotic effects of crossing two genetically distinct breeding lines. The agronomic performance of this offspring is superior to both parents, typically in vigour, yield, and uniformity. The better performance of hybrid seed varieties compared to open-pollinated varieties makes the hybrid seed more attractive for farmers to plant and thereby commands a premium price in the market place.

In order to produce hybrid seed uncontaminated with selfed seed pollination control methods must be implemented to ensure cross-pollination and not self-pollination. Pollination control mechanisms can be mechanical, chemical, or genetic.

A simple mechanical method for hybrid seed production can be used if the plant species in question has spat-ally separate male and female flowers or separate male and female plants. The corn plant, for example, has pollen producing male flowers in an inflorescence at the apex of the plant and female flowers in the axils of leaves along the stem. Outcrossing is assured by mechanically de-tasselling female plants to prevent selfing.

Most major crop plants of interest, however, have both functional male and female organs within the same flower so emasculation is not a simple procedure. It is possible to remove by hand the pollen forming organs before pollen shed, however this form of hybrid seed production is extremely labour intensive and hence expensive. Seed is produced in this manner if the value and amount of seed recovered warrants the effort.

A second general method of producing hybrid seed is to use chemicals that kill or block viable pollen formation. These chemicals, termed gametocides, are used to impart a transitory male-sterility. Commercial production of hybrid seed by use of gametocides is limited by the expense and availability of the chemicals and the reliability and length of action of the applications. These chemicals are not effective For crops with an extended flowering period because new flowers will be produced that will not be affected. Repeated application of chemicals is impractical because of costs.

Many current commercial hybrid seed production systems for field crops rely on a genetic method of pollination control. Plants that are used as females either fail to make pollen, fail to shed pollen or produce pollen that is biochemically unable to effect self-fertilization. Plants that are unable (by several different means) to self pollinate biochemically are termed self-incompatible. Difficulties associated with the use of self-incompatibilities are: availability and propagation of the self-incompatible female line and stability of the self-incompatibility. In some instances self-incompatibility can be overcome chemically or immature buds can be pollinated by hand before the biochemical mechanism that blocks pollen is activated. Self-incompatible systems that can be deactivated are often very vulnerable to stressful climatic conditions that break or reduce the effectiveness of the biochemical block to self-pollination.

Of more widespread interest for commercial seed production are systems of pollen control based on genetic mechanisms causing male sterility. These systems are of two general types: (a) genic male sterility, which is the failure of pollen formation because of one or more nuclear genes or (b) cytoplasmic-genetic male sterility (commonly called cytoplasmic male sterility or CMS) in which pollen formation is blocked or aborted because of a defect in a cytoplasmic organelle (mitochondrion) (for general discussions on genic sterility, CMS and hybrid formation in plants see Frankel, R., et al., *Pollination Mechanisms, Reproduction and Plant Breeding*; Springer V., et al., *Monographs on Theoretical and Applied Genetics*, N.Y, 1977; Edwardson, J. P., *Bot. Rev.* 36:341–420, 1970).

Nuclear (genic) sterility can be either dominant or recessive. A dominant sterility can only be used for hybrid seed production if fertility of the hybrid plants is not critical and if propagation of the female line is feasible (eg. by clonal propagation or by the use of a selectable marker closely linked to the sterility gene).

Many successful hybridization schemes involve the use of CMS. In these systems, a specific mutation in the cytoplasmically located mitochondrion can, when in the proper nuclear background, lead to the failure of mature pollen formation. In some other instances, the nuclear background can compensate for the cytoplasmic mutation and normal pollen formation occurs. The nuclear trait that allows pollen formation in plants with CMS mitochondria is called restoration and is the property of specific "restorer genes". Generally the use of CMS for commercial seed production involves the use of three breeding lines, the male-sterile line (female parent), a maintainer line which is isogenic to the male-sterile line but contains fully functional mitochondria and the male parent line.

The male parent line may carry the specific restorer genes (usually designated a restorer line) which then imparts fertility to the hybrid seed. For crops (eg. vegetables) for which seed recovery from the hybrid is unimportant, a CMS system could be used without restoration. For crops for which the fruit or seed of the hybrid is the commercial product then the fertility of the hybrid seed must be restored by specific restorer genes in the male parent or the male-sterile hybrid must be pollinated. Pollination of non-restored hybrids can be achieved by including with hybrids a small percentage of male fertile plants to effect pollination. In most species, the CMS trait is inherited maternally (because all cytoplasmic organelles are inherited from the egg cell only), which can restrict the use of the system.

In a crop of particular interest herein, the oilseed crop of the species *Brassica napus* or *Brassica campestris*, commonly referred to as Canola, no commercial hybrid system has been perfected to date. Mechanical emasculation of flowers is not practical for hybrid seed production on any scale. The use of currently available gametocides is impractical because of the indeterminate nature of flower production. Repeated application of chemicals is expensive and the method is prone to contamination with selfed seed.

Genes that result in self-incompatibility are quite widespread in Brassica species and self-incompatible hybrid systems have been used for hybrid seed production in vegetables. Major difficulties are associated with the propagation of the female lines and the breakdown of self-incompatibilities under stressful conditions. Adaptation of these systems to Brassica oilseeds is restricted by the expense of increasing the female lines and the availability of appropriate self-incompatible genes in the dominant Canola species, *Brassica napus*.

A variety of sources of male sterility are available in Brassica species. Both recessive and dominant genic systems have been reported, however their use is restricted because large scale in vitro propagation or roguing of female lines is in most cases impractical for large scale seed production.

Additionally, a number of CMS systems have been reported in Brassica species. Four of these systems have been explored as possible vehicles for hybrid seed production: pol, nap, anand and ogu. The Polima system (pol) has been widely studied and is probably the closest to commercial use. Good restoration and maintenance of pol CMS has been achieved, however the system suffers from potential instability of the CMS with high temperature, a reduction in the heterotic effect of crossing different lines (because of the defective mitochondria) and a reduction in hybrid seed oil content. The use of other CMS systems is also restricted by heat sensitivity (nap), difficulty in restoration of fertility (ogu, anand), difficulty in the maintenance of the sterility (nap) and low temperature chlorosis associated with the sterile cytoplasm (ogu). Improvement of these systems is the object of considerable research, however all of the systems have some inherent weaknesses that limit their utility.

For a general discussion of male sterility in Brassica see Shiga, T., *Male Sterility and Cytoplasmic Differentiation. In Brassica Crops and Wild Alles, Biology and Breeding*, Japan Scientific Societies Press, Tokyo pp. 205–221; Thompson, K. F., *Heredity 29:253–257*).

It is recognized that a desirable system for hybrid seed production in any crop would be a form of genic male sterility that could be regulated or overcome to allow male fertility for the propagation or increase of the female lines or to allow fertility in hybrids. This recognition has stimulated research on the use of molecular systems to effect genic male sterility that could be used for hybrid seed formation. In addition, the advent and widespread application of recombinant DNA techniques may provide a mechanism of introduction of novel DNA sequences into a wide variety of different crop species that is not possible by the limited sexual methods of genetic exchange between different species. A molecular approach has the advantage that the hybridization system can be imposed on all breeding lines or cultivars of any given crop without the need for extensive backcrossing and disruption of established inbred lines leading to the rapid production of male sterile lines with well characterized and superior agronomic performance.

SUMMARY OF THE INVENTION

The present invention relates to a recombinant DNA molecule for use in the preparation of a male-sterile plant or a plant carrying a male-sterile trait and reproductive material of said plants, comprising (a) one or more DNA sequences which may be the same or different, which encode a gene product which when produced in a cell of a plant which is essential to pollen formation and/or function is directly or indirectly capable of substantially interfering with the function and/or development of said cell; and (b) one or more promoters which may be the same or different, said promoters being capable of regulating the expression of said DNA sequences; and wherein the DNA sequences and promoters are selected such that the gene product selectively interferes with the function and/or development of a cell of a plant that is essential to pollen formation and/or function and whereby a plant regenerated from a cell of a plant having said recombinant DNA molecule integrated into its genome is substantially male-sterile or carries the male sterile trait.

A gene product which is directly capable of interfering with the function and/or development of a cell of a plant which is essential to pollen formation and/or function includes a protein or polypeptide which is substantially cytotoxic to the cell, or a nucleotide sequence which interferes with the expression of a gene which is essential to pollen formation and/or function or a gene which is essential to the continued development and/or function of all metabolically competent cells of a plant. A gene product which is indirectly capable of interfering with the function and/or development of a cell of a plant which is essential to pollen formation and/or function includes a protein or polypeptide which renders the cell susceptible to a chemical agent or physiological stress or a protein or polypeptide which render a non-toxic substance substantially cytotoxic to the cell.

In one embodiment of the invention a recombinant DNA molecule is provided which comprises at least one DNA sequence which encodes a gene product which when produced in a cell of a plant which is essential to pollen formation and/or function is substantially cytotoxic to said cell.

In a preferred embodiment of the invention a recombinant DNA molecule is provided which comprises at least one DNA sequence which is an anti-sense gene which encodes an RNA which substantially interferes with the expression of a sense gene which is essential to pollen formation and/or function of a plant.

In another preferred embodiment of the invention a recombinant DNA molecule is provided which comprises at least one DNA sequence which is an anti-sense gene which encodes an RNA which substantially interferes with the expression of a sense gene which is essential to the continued development and/or function of all metabolically competent cells of a plant.

In a further preferred embodiment of the invention a recombinant DNA molecule is provided comprising at least one DNA sequence which encodes a protein or polypeptide which when produced in a cell of a plant which is essential to pollen formation and/or function is substantially cytotoxic to said cell.

In another embodiment of the invention a recombinant DNA molecule is provided comprising at least one DNA sequence which encodes a gene product which when produced in a cell of a plant which is essential to pollen formation and/or function renders a non-toxic substance cytotoxic to said cell. The recombinant DNA molecule may additionally comprise a second DNA sequence which encodes a second gene product which converts a substance which is endogenous to a plant cell to the non-toxic substance.

In still another embodiment of the invention a recombinant DNA molecule is provided comprising at least one DNA sequence which is an anti-sense gene which encodes an RNA which substantially interferes with the expression of a sense gene which confers on cells of a plant resistance to a chemical agent or physiological stress.

The recombinant DNA molecules of the invention comprise a promoter(s) which promoter(s) may be selected from the group of promoters consisting of a constitutive promoter, an inducible promoter which is active throughout pollen formation or during Transcription of one or more of the DNA sequences; and, a pollen specific promoter which, regulates the expression of one or more of the DNA sequences selectively in cells of a plant which are essential to pollen formation and/or function.

The invention also relates to a pollen specific promoter which regulates the expression of a DNA sequence selectively in cells of a plant which are essential to pollen formation and/or function.

The present invention additionally relates to a plasmid vector containing one or more recombinant DNA molecules of the invention which vector is adapted to transform plant cells, a plant cell containing a recombinant DNA molecule of the invention, a plant cell culture containing the plant cell, a plant containing the plant cell and a seed of such a plant, a process for producing a male-sterile plant, a process of producing a hybrid seed and hybrid seed so produced, and a hybrid plant obtained by growing the hybrid seed and a hybrid seed produced from the hybrid plant.

The following advantages over other hybridization systems may be obtained using the methods according to the present invention:

(a) Hybrid seed production is not labour intensive and can be achieved on a large scale with commercially acceptable costs;

(b) Male sterility is simply inherited and stable in response to environmental stresses that limit the effectiveness of self-incompatibility and CMS based schemes;

(c) Seed that is produced will be relatively uncontaminated by selfed seed;

(d) The system avoids the use of defective cytoplasmic organelles that may detract from the performance of hybrid seed;

(e) The system will greatly speed the development and increase the number of lines that can be tested as parents in a hybrid cross because it can be imposed on any plant or. inbred line capable of being transformed and regenerated into plants without the inclusion of additional genomic DNA. Additionally plant lines can be tested for combining ability before inclusion of the hybridizing system which can modify breeding strategy.

BRIEF DESCRIPTION OF THE DRAWINGS

FIG. 3a is the complete nucleotide sequence of the clone L 4 represented in FIG. 2a. Only the coding strand is shown for clarity.

FIG. 3b is the nucleotide sequence of the portion of the clone L 10 shown in Figure as being underlined in FIG. 2b. Only the coding strand is shown for clarity.

FIG. 3c is the nucleotide sequence of the portion of the clone L 16 shown in Figure as being underlined in FIG. 2c. Only the coding strand is shown for clarity.

FIGS. 3d-3y is the nucleotide sequence of the portion of the clone L 19 shown in Figure as being underlined in FIG. 2d. Only the coding strand is shown for clarity.

FIG. 4 is the nucleotide sequence of 3 cDNA clones isolated from a microspore derived cDNA library of *Brassica napus*. These clones are named cBp401, cBp405, and cBp408. These three cDNA clones are extremely homologous to members of the L4 *Brassica napus* microspore specific gene family (Bp4A, Bp4B, Bp4C). The nucleotide sequence of two of these 3 members of the L4 *Brassica napus* microspore specific gene family are shown in this Figure (Bp4A, Bp4C). The gene Bp4C was chosen as a master sequence for comparison. The deduced nucleotide coding sequence for the genes Bp4A and Bp4C is shown as a sequence from which the two exons of the genes have been spliced together at the positions normally spliced in vivo. This gives rise to the coding sequence in the mature mRNA. The cDNA clones are aligned with the sequence of Bp4C such that only nucleotide changes are shown. The sequences are therefore represented as variants of a single master sequence of gene Bp4C which is shown on line 1. The ATG start codon as well as the TGA or TAA stop codons are underlined. These three cDNA clones correspond to related members of the *Brassica napus* microspore specific gene family a portion of which is contained in the clone L4.

FIG. 5 shows a partial nucleotide sequence of a cDNA clone that is closely homologous to the gene contained in the clone L10, the restriction map of which is shown in FIG. 2b.

FIG. 6 is the nucleotide sequence of the cDNA clone that is the gene product of clone L19, the restriction map of which is shown in FIG. 2d.

FIGS. 7A, 7B, 7C, 7D are schematic representations describing the production of vectors containing the promoter and promoter regions from clone L4. The specific examples are discussed in greater detail below. FIG. 7E shows a schematic representation of the promoter constructs produced as shown, schematically in FIGS. 7A to 7E.

FIG. 17 illustrates hybrid seed production using the binary cryptocytotoxicity method based on the use of the IamH and IamS genes described in FIGS. 15 and 16.

FIG. 18 illustrates the segregation patterns of the IamH and IamS genes in the F1 and F2 populations when the genes are on the same segregation unit.

FIG. 19 is an alternate representation of the procedure used to isolate the T-DNA gene 2 (the IamH gene) of *Agrobacterium tumefaciens* and the production of a promoterless version of this gene.

DETAILED DESCRIPTION OF THE INVENTION

Figure 1:
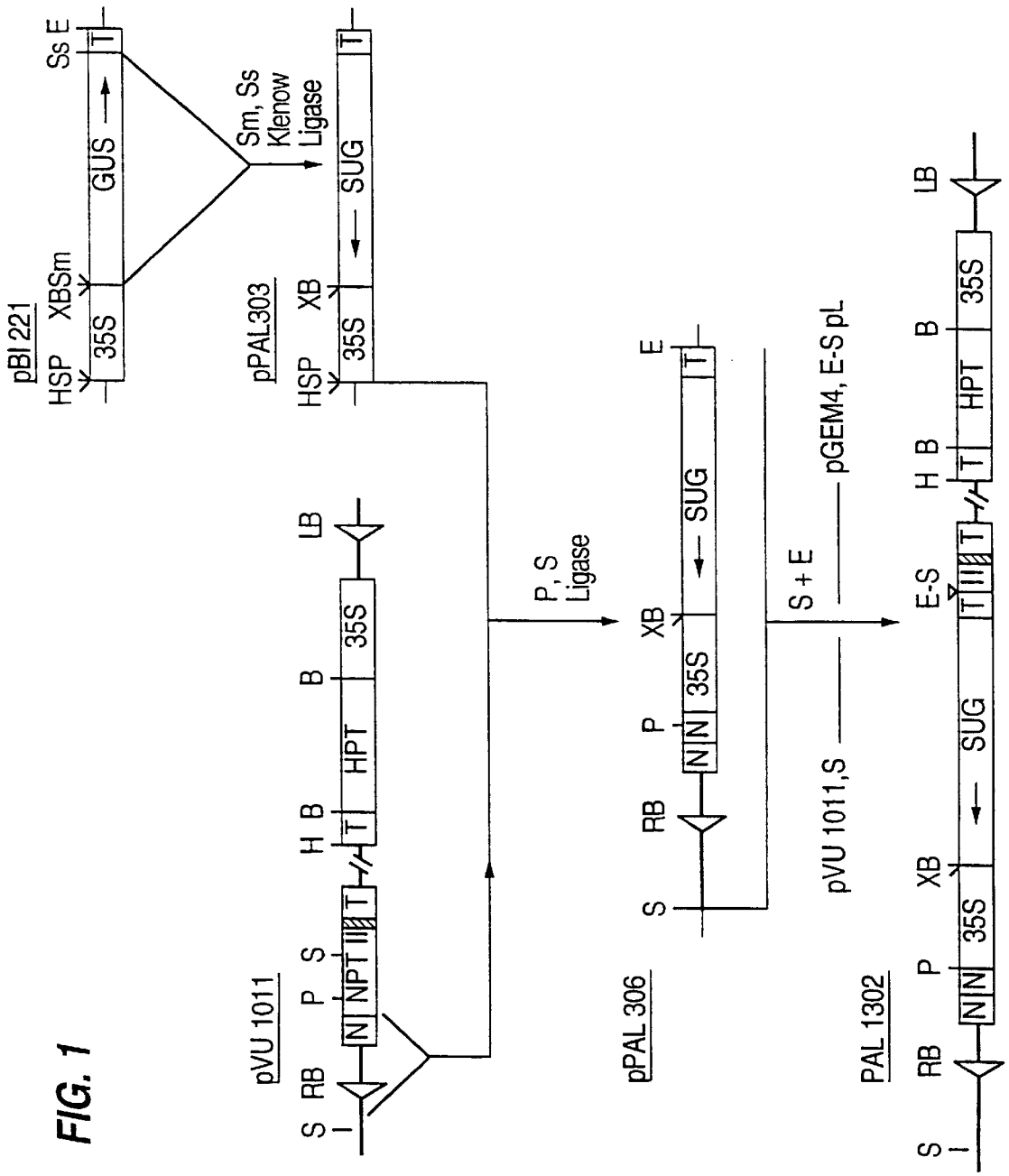
FIG. 1 is a representation of the construct-on of an anti-sense gene vector that was used for anti-sense RNA inhibition of Beta-glucuronidase gene activity in transgenic plants.

As hereinbefore mentioned the invention relates to a recombinant DNA molecule for use in the preparation of a male sterile plant or a plant carrying a male sterile trait and/or reproductive material of the plants. The recombinant DNA molecule contains one or more DNA sequences which may be the same or different, which encode a gene product. The gene product includes a nucleotide sequence, in particular an RNA sequence, a protein or a polypeptide. When produced in a cell and/or tissue of a plant which is essential to pollen formation and/or function the gene product is directly or indirectly capable of interfering with the function and/or development of the cell. A cell and/or tissue of a plant which is essential to pollen formation and/or function includes cells and/or tissues ok that are instrumental in the development or function of pollen, including cells and/or tissues from which pollen develops (e.g. premeiotic and uninucleate microspore cells), cells and/or tissues which form part of the male structure in which pollen develops (e.g. anther, tapetum or filament) and pollen itself. The recombinant DNA molecule may also contain one or more promoters, which may be the same or different, which are capable of regulating the expression of the DNA sequences in the recombinant DNA molecule. The DNA sequences and promoters in the recombinant DNA molecule are selected such that the gene product selectively Interferes with the function and/or development of a cell of a plant what is essential to pollen formation and/or function.

The recombinant DNA molecule of the invention may contain one or more DNA sequences which may be the same or different. The DNA sequences may be selected from the following DNA sequences:

(a) a DNA sequence which encodes an RNA which when produced in a cell of a plant which is essential to pollen formation and/or function substantially interferes with the expression of;
  (i) a gene which is essential to pollen formation and/or function;
  (ii) a gene which is essential to the continued development and/or function of all metabolically competent cells of a plant; or
  (iii) a gene which confers on a cells of a plant resistance to a chemical agent or physiological stress;

(b) a DNA sequence which encodes a protein or polypeptide which when produced in a cell of a plant which is essential to pollen formation and/or function is substantially cytotoxic to said cell; and (c) a DNA sequence which encodes a protein or polypeptide which when produced in a cell of a plant which is essential to pollen formation or function renders a non-toxic substance substantially cytotoxic to said cell; and (d) a DNA sequence which encodes a gene product which when produced in a cell of a plant which is essential to pollen formation and/or function renders said cell susceptible to a chemical agent or physiological stress.

(e) a DNA sequence which encodes a gene product which may be converted into a substance which is cytotoxic to cells/tissues essential for pollen formation and/or function.

The above DNA sequences (a) to (e) are further described below in relation to the various embodiments of the invention.

According to a first embodiment of the present invention genic male sterility may be produced by Transforming plant cells that are capable of regeneration into a differentiated whole plant, with a recombinant DNA molecule containing an anti-sense gene which encodes a gene product, in particular RNA which is capable of interfering with the expression of a sense gene. Preferably, the recombinant DNA molecule encodes RNA which is complementary to and capable of hybridizing with the RNA encoded by a sense gene.

An anti-sense gene is a DNA sequence produced when a sense gene is inverted relative to its normal presentation for transcription. An anti-sense gene may be constructed in a number of different ways, provided that it is capable of interfering with the expression of a sense gene. Preferably, the anti-sense gene is constructed by inverting the coding region of a sense gene relative to its normal presentation for transcription to allow for transcription of its complement; hence the RNA's encoded by the anti-sense and sense gene are complementary. It is understood that a portion of an anti-sense gene incorporated in the recombinant DNA molecule of the invention may be sufficient to selectively interfere with the expression of a sense gene and thus the term "anti-sense gene" used herein encompasses a functional portion of an anti-sense gene.

A sense gene is a gene which may only be expressed in cells and/or tissues of a plant that are essential to pollen formation and/or function. Preferably, the sense gene is a gene only expressed at specific stages during pollen development whose regulation is tightly controlled. The sense gene may also be a gene that is essential for the continued development or function of all metabolically competent cells/tissues such as but not limited to genes involved in essential cellular structures, and essential metabolism including essential biosynthesis. The sense gene further may be a gene which confers on cells/tissues of a plant resistance to a chemical agent or physiological stress.

It is understood herein that it is not essential to identify and isolate the sense gene de novo. Rather, the sense gene may have been described in the literature or obtained commercially.

The isolation of sense genes that are essential to pollen formation and/or function may be accomplished by a variety of procedures. A detailed description of a procedure for isolating such sense genes is set out below.

Since the sense gene in question may initially be isolated in its native form, is to be understood that the term "sense gene" as used herein may refer to one or more parts of the gene including 5' untranslated leader sequences, coding sequences, promoter sequences, intron sequences, and untranscribed 3' sequences, or any substantial fragments of these sequences.

The present inventors have isolated DNA sequences from a plant of the species *Brassica napus ssp oleifera* w Westar which are expressed only in microspores and whose expression is essential to microspore function and/or development and hence a preferred embodiment of the present invention provides a recombinant DNA molecule containing, one or more anti-sense genes to these isolated DNA sequences. A schematic representation of the restriction maps and coding regions of the microspore specific genes identified as L4, L10, L16 and L19 are shown in FIGS. 2a, 2b, 2c, and 2d, respectively. The complete nucleotide sequence of clones L4, and relevant sequences of L10, L16 and L19 are shown in FIGS. 3a, 3b, 3c, and 3d respectively. The nucleotide sequences of isolated cDNA clones that correspond to the genes or related gene family members within clones L4, L10 and L19 are shown in FIGS. 4, 5, and 6, respectively. In a preferred embodiment of the invention the recombinant DNA molecule contains one or more of an anti-sense gene to the microspore specific genes identified as L10 and L19.

It is believed that identical or homologous microspore specific DNA sequences to those isolated from *Brassica napus* described herein will be found and expressed exclusively in pollen of other species of pollen-bearing plants, particularly species of plants within the genus Brassica and the family Cruciferae (also known as Brassicaceae), and more particularly other cultivars of *Brassica napus*.

The occurrence of the microspore specific sequences isolated from *Brassica napus* in other species of pollen-bearing plants may be routinely ascertained by known hybridization techniques. It is believed that the similarity of plant genes from species to species will allow for the embodiments of the present invention to be carried out using the DNA sequence in any number of pollen bearing plant species that are capable of being genetically transformed. The universality of plant genes has been widely documented in the literature and homologous plant genes have been described for plant actins (Shah, D. M., et al, J. Mol. Appl. Genet. 2:111–126, 1983), phytochrome (Hershey, H. P., et al., Proc. Natl. Acad. Sci. USA 81:2332–2337, 1984) storage proteins (Singh, N. K., et al., Plant Mol. Biol. 11:633–639, 1988) enzymes such as glutamine, synthase (Lightfoot, D. A., et al, Plant Mol. Biol. 11:191–202, 1988, and references within) and nitrate reductase (Cheng, C., et al, EMBO Jour. 7:3309–3314). These and other examples in the literature clearly demonstrate that many plant genes are highly conserved. It is also clear that this conservation applies not only to structural proteins but to enzymatic proteins important to cellular physiology. Therefore, it is believed that the DNA sequences, when found in another plant species, will be essential to microspore development and will be useful in carrying out the present invention in such species.

It has also been demonstrated that anti-sense RNA sequences derived from one plant species can effectively inhibit the expression of homologous DNA sequences in a different species (Van der Krol, et al, 1988, Nature 333:866–869). Therefore, it is expected that anti-sense RNA derived all or in part from Brassica microspore specific DNA sequences will be functional in other plants.

As hereinbefore mentioned the sense gene may also be a sense gene that is essential for the development and/or function of all metabolically competent cells/tissues such as but not limited to genes involved in essential cellular structures, essential biosynthesis and essential metabolism. Examples of such sense genes may be found in the literature and include the genes which encode actin, tubulin or ubiquitin; three proteins which are essential to cellular growth and development.

Sequences for ac-in genes isolated from plants have been published (for example; Baird W. V., and Meagher, R. B., EMBO J. 6:3223–3231, 1987, or Shah, D. M., Hightower, R. C. and Meagher, R. B., Proc Natl Acad Sci USA 79:1022–1026, 1982) and actin is known to play a critical role in normal cellular function especially during mitosis and meiosis where actin forms part of the cellular apparatus for cellular division.

The sequence for plant tubulin as also been described (Raha, D., Sen, K. and Biswas, B. B. Plant Mol Biol 9:565–571, 1987). Tubulin, like actin, is known to be important in the cellular life cycle particularly in regards to cell shape, transport and spindle formation during mitosis and meiosis.

The DNA sequence for plant ubiquitin has also been published (Gausing, K. and Barkardottir, R. Eur J. Biochem 158:57–62, 1986). Ubiquitin is a protein involved in the turnover of cellular proteins and as such has a critical role in the regulation of specific cellular protein levels. In addition, ubiquitin is one of the most highly conserved proteins in eukaryotic cells. Interference with ubiquitin expression can cause abnormalities in the turnover of cellular proteins.

If any of the aforementioned proteins are not present in the cell, proper cellular function is interfered with and the cell fails to develop properly.

It is believed that a gene that is found to be essential for the continued development or function of all metabolically competent cells in one plant species will have a similar counterpart in other plant species, since it is generally understood that within the plant kingdom there are genes that are nearly identical or very homologous involved in the basic processes that control or are a result of cellular development. It is further believed that a gene which encodes a gene product which interferes with the expression of said gene (ie. an anti-sense gene) in one plant species will have the ability to do so in other plant species.

The tissue-specific and developmentally regulated expression of a wheat endosperm protein synthesized in tobacco plants genetically transformed with this wheat gene has been reported (Flavell, R. B., et al, Second International Congress for Plant Molecular Biology, Abstract #97). In that example, the wheat gene functioned in the tobacco plant in an identical fashion to the way in which it functions in a wheat plant. Other literature clearly shows that the regulation of a specific gene, which can be in many cases complex, is maintained in transgenic plants. One example of this s the phytochrome mediated regulation of a wheat Chlorophyll a/b-binding protein in transgenic tobacco (Nagy, F. et al, EMBO Jour. 5:1119–1124, 1986). In this example the light responsive specific regulation of the wheat gene was maintained in the foreign genetic environment. Not only do cereal genes function in a conserved manner, but genes from other plant species that are more closely related maintain functionality in heterologous genetic systems. Pea seed proteins are expressed properly in tobacco plants (Higgins, T. J. V., et al Plant Mol. Biol. 11:683–696, 1988), as are soybean seed proteins, (Barker, S. J., et al, Proc. Natl. Acad. Sci.USA 85:458–462, 1988) and pea rbcS genes (Nagy, F. et al., EMBO Jour. 4:3063–3068, 1985). The scientific literature has numerous other examples of genes that have been used to genetically transform plants and those genes maintain their ability to function properly in this new genetic environment. Therefore the conserved nature of these genes, not only in the DNA sequences which control the expression of these genes, but the actual protein structure coded for by these genes, is similar among the plant species.

As hereinbefore mentioned, the sense gene may be a gene which confers on cells of a plant resistance to a chemical agent or a naturally occurring or artificially incurred physiological stress. Such a sense gene may be native to a plant cell or say be a foreign sense gene for example, a gene from another plant species. If the gene is a foreign gene it may be introduced into the genome of a plant cell prior to, after, or concurrently with the anti-sense gene as will be described below. Examples of such sense genes may be identified in the literature and include genes which confer resistance to a herbicide such as acetolactate synthase which confers resistance to chlorosulfuron; genes which confer resistance to a physiological stress such as the gene encoding superoxide dismutase which actively reduces oxygen radicals; genes which confer resistance to uv light and wounding (phenyl and alanine ammonia lyase or chalcone synthase) genes which confer resistance to disease or pests (e.g. $\beta$1,3 glucanases, chitinase or proteinase) genes which confer resistance to antibiotics and certain toxic drugs such as the gene encoding neomycin phosphotransferase II conferring resistance to kanamycin.

The recombinant DNA molecule containing an anti-sense gene of the present invention additionally contains a promoter which regulates the expression of the anti-sense gene. If more than one DNA sequence containing an anti-sense gene (or one or more of a gene encoding a cytotoxic substance or a gene which confers susceptibility to a chemical agent or physiological stress) is present in the recombinant DNA molecule of the invention, the DNA sequences may be regulated by an identical promoter or each may be regulated by a different promoter.

If the sense gene is a gene which is only expressed in cells/tissues of a plant that are essential to pollen formation and/or function, then a promoter that functions in all, many, or a variety of cell types including cells/tissues essential to pollen formation and/or function may be used in the construction of an anti-sense gene. An example of such a constitutive promoter is CaMV 35S or preferably HP 101 which has been isolated from *Brassica napus* as described below. Thus, the promoter that is used may be constitutively active in all or many cell types but the anti-sense gene whose expression is regulated by such a promoter will only interfere with the expression of the sense gene in those cells/tissues producing the sense gene in question i.e. cells/tissues essential to pollen formation and/or function.

It is also possible to use an inducible promoter to regulate the expression of the anti-sense gene. An inducible promoter is a promoter that is capable of directly or indirectly activating transcription of one or more DNA sequences or genes in response to an inducer. In the absence of an inducer the DNA sequences or genes will not be transcribed. Typically the protein factor that binds specifically to an inducible promoter to activate transcription is present in an inactive form which is then directly or indirectly converted to the active form by the inducer. The inducer may be a chemical agent such as a protein, metabolite (sugar, alcohol etc.),a growth regulator, herbicide, or a phenolic compound or a physiological stress imposed directly by heat, salt, toxic elements etc. or indirectly through the action of a pathogen or disease agent such as a virus. A plant cell containing an inducible promoter may be exposed to an inducer by externally applying the inducer to the cell such as by spraying, watering, heating,or similar methods. Examples of inducible promoters include the inducible 70 KD heat shock promoter of *D.melanogaster* (Freeling, M., Bennet, D. C., Maize ADN 1, Ann. Rev. of Genetics 19:297–323) and the alcohol dehydrogenase promoter which is induced by ethanol (Nagao, R. T., et al., Miflin, B. J., Ed. Oxford Surveys of Plant Molecular and Cell Biology, Vol. 3., p. 384–438, Oxford University Press, Oxford 1986). The inducible promoter may be in an induced state throughout pollen formation or at least for a period which corresponds to the transcription of the sense gene. A promoter that is inducible by a simple chemical is particularly useful since the male sterile plant can easily be maintained by self-pollination when grown in the absence of such a chemical.

Alternatively, if the sense gene is a gene essential for the development and/or function of all metabolically competent cells/tissues or a gene which confers on cells of a plant resistance to a chemical agent or physiological stress, a promoter that is active only in cells/tissues essential to pollen formation and/or function (for example, a pollen specific promoter is preferably used to regulate the expression of the anti-sense gene.

The invention also relates to a pollen specific promoter or functional portions thereof and chimeric promoters constructed using the pollen specific promoter and/or portions thereof.

A pollen specific promoter is a DNA sequence which regulates the expression of a DNA sequence selectively in the cells/tissues of a plant essential to pollen format-on and/or function and/or limits the expression of such a DNA sequence to the period of pollen formation in the plant.

Preferably, the pollen specific promoter is a DNA sequence corresponding to the promoter sequence in the microspore specific genes identified as L4, L10, L16 and L19 herein or a functional fragment thereof; or a chimeric promoter sequence containing one or more of a promoter sequence from the microspore specific genes identified as L4, L10, L16 and L19 or portions of such promoter sequences. The preferred pollen specific promoters may be used in conjunction with naturally occurring flanking coding or transcribed sequences described herein or with any other coding or transcribed sequence that is essential to pollen formation and/or function.

The pollen specific promoters referred to above were isolated from a plant of the species Brassica napus. It is believed that the it is possible to use these promoters to limit the expression of a given DNA sequence to pollen formation and/or function and to a specific period during pollen formation and/or development from a plant of a different species. The published scientific literature has clearly shown that plant genes are universal and the plant tissue-specific promoter fragments retain their function in other species. For example, wheat endosperm promoter fragments function to give appropriate seed specific expression in tobacco (Simpson, J. et al, EMBO Jour. 4:2723–2729, 1985) and the alcohol dehydrogenase promoter (Adh-1) from corn (Zea mays) can be used in conjunction with other promoter fragments to give appropriate expression in tobacco Ellis, J. G., et al., 1987, EMBO J. 6:11–16). Additionally the maize transposable element Ac is active in tobacco and other plant species (Taylor, et al., 1989, Plant Mol. Biol. 13:109–118) providing further evidence of the universality of plant gene structure and function. These examples demonstrate the equivalent tissue specific function of the same promoters in very widely divergent species (monocots to dicots). Research studies have shown equivalent promoter function in more closely related species within the same family or between families such as the Solanaceae and Brassicaceae.

It is appreciated, however, that refinements in promoter function may be required for individual plants or species to maximize or modulate the appropriate timing or level of expression to carry out aspects of the invention. Accordingly methods or the modification of promoters to modify or improve function in various plants of different origin are provided herein.

The pollen specific promoters obtained from Brassica napus described herein may also be used to as probes to isolate pollen specific promoters in other plant species.

It is noted that there is not a high degree of DNA sequence homology between the native pollen specific promoters from the L4, L10, L16 and L19 clones. Test data reveal that the timing and level of expression of these genes is not identical in pollen, but that all overlap in activity at some time. This illustrates that there are divergent gene sequences in Brassica napus that still function as pollen specific promoters.

It is expected that one may use any number of different pollen specific promoters to regulate the expression of a DNA sequence in a recombinant DNA molecule of the invention. In order to determine what pollen specific promoter may be used to regulate the expression of an anti-sense gene (or other sequences which will be discussed below in regard to other embodiments of the invention) consideration is to be given to a number of factors.

The pollen specific promoter used should be a promoter, or a modified form of the promoter, that is active at the appropriate time to produce sufficient levels of transcribed RNA to carry out the invention. The pollen specific promoters derived from pollen specific clones disclosed herein (namely those derived from the microspore genes identified as L4, L10, L16 and L19) that are active early in the development of microspores such that gene expression takes place both during and after the meiotic and mitotic division of pollen mother cells. Thus, the activity of these promoters is not limited by segregation.

When using a pollen specific promoter to inactivate a sense gene that is essential to pollen formation and/or function, as hereinbefore discussed, it may be difficult to predict, a priori, which pollen specific promoter or modified promoter construct will effectively block the Function of such a gene. It is preferable to use a pollen specific promoter that displays a similar developmental pattern to the gene. A convenient method to determine when the sense gene targeted for interference is expressed is to isolate RNA from developing microspores at different stages and to analyze this RNA for the expression of the sense gene by the so-called Northern blot analysis. This procedure will allow for the determination of the developmental period in which the sense gene is expressed. In order to determine the developmental period in which a pollen specific promoter gene is expressed, a similar series of analyses can be carried out using as a probe a reporter gene such as beta-glucuronidase joined to the pollen specific promoter, or a native sense gene from the same plant species from which a pollen specific promoter is isolated and whose expression is regulated by the pollen specific promoter. When the pollen specific promoter is isolated from one plant and used in a different plant species the preferred method is the use of a reporter gene joined to the promoter to determine the exact developmental timing that the promoter has in that particular plant species.

It is understood that the activity of a pollen specific promoter, whether intended for the same or different species may be modified in structure to change or alter activity in a plant. Changes that are contemplated include but are not necessarily limited to: addition or deletion of sequences, orientation of upstream or downstream sequences, and the inclusion of introns or parts of the coding sequence of the pollen specific gene. The above modification may serve to increase expression or improve regulation of expression to targeted stages of development.

It should be noted that the identification of a promoter region (including constitutive, inducible and pollen specific promoters) is usually defined by function rather than a set DNA sequence. Two hundred (200) nucleotide bases or less of a promoter sequence may be sufficient to maintain promoter function. It should also be recognized that some upstream DNA sequences can be arranged in opposite orientations and still retain or demonstrate enhanced promoter function. In addition, "enhancer-like" DNA sequences, which are usually small conserved DNA sequences ranging in size from less than 10 nucleotides to considerably larger numbers of nucleotides may also be Inserted into promoter regions to enhance expression.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant essential for pollen formation and/or function.

Additionally regions of one promoter may be joined to regions from a different promoter in order to obtain the desired promoter activity. Specific examples of chimeric promoter constructs are the chimeric promoters contained in the vectors PAL 1107 and PAL 1106.

It is desirable that the pollen specific promoter (or constitutive or inducible promoter whichever is selected to construct a recombinant DNA molecule of the invention) function so that sufficient levels of anti-sense RNA are provided to substantially interfere with the expression of the sense gene. Investigations of the mechanism of anti-sense RNA inhibition of gene expression in model systems have suggested that equal or greater than equal levels of anti-sense RNA may be required in order to observe a significant reduction of sense gene activity. However, in some cases it is noted that low levels of anti-sense RNA can have a specific reduction in sense gene activity. Therefore, in some instances if the sense gene that is targeted for inactivation by anti-sense RNA is a gene that is found to be essential for the continued develooment or function of all metabolically competent cells, or a gene that is expressed in all cell types at a low level, an excess of anti-sense RNA may not be required for inhibition. Additionally less than total reduction of the gene activity may be more than sufficient to disrupt pollen development which is known to be very sensitive to many stressful conditions. Therefore, it is suggested that the pollen specific promoter that is used to carry out certain aspects of this invention be chosen based on the observation that the pollen specific promoter functions to cause the expression of any sequences adjacent to it to be transcribed at a time that parallels or overlaps the period of time that the sense gene sought to be inactivated is expressed and that the levels of anti-sense RNA expressed from the anti-sense gene be of levels sufficient to inhibit the sense gene expression, usually to mean greater than or equal to the levels of sense RNA.

By using a pollen specific promoter to regulate the expression of an anti-sense gene, it is possible to interfere with for example, normal microspore development in any given plant, without having first to isolate from the genomic DNA of the plant a sense gene which is essential to microspore development. Thus, a male sterile plant may be produced where the sense gene targeted for interference is a gene that is essential for the development and/or function of all metabolically competent cells/tissues. To produce a male sterile plant, such a gene is specifically interfered with by using a recombinant DNA molecule containing a pollen specific promoter to regulate the transcription of the anti-sense gene.

Furthermore, a male sterile plant may be produced by growing a plant which has a recombinant DNA molecule comprising an anti-sense gene to a gene which confers on cells of a plant resistance to a chemical agent or a naturally occurring or artificially induced physiological stress and a pollen specific promoter. The transcription product of the anti-sense gene will interfere with the expression of the sense gene in cells/tissues essential to pollen formation and/or function. The sense gene confers on the remainder of the plant resistance to the stress.

In order to interfere with the expression of a sense gene, it is preferred that :he anti-sense gene and sense gene be expressed at about the same time. The co-incident expression of sense and anti-sense genes may be achieved in a variety of ways using combinations of constitutive, inducible and organ specific promoters (for example, a pollen specific promoter as hereinbefore described). However, co-incident expression may be readily achieved by regulating the expression of the anti-sense gene with the same promoter that controls the sense gene, thereby causing both to be transcribed in the same time frame. The concept of regulating gene expression using anti-sense genes is described in Weintraub, H. et al., *Antisense RNA as a molecular tool for genetic analysis*, Reviews—Trends in Genetics, Vol. 1(1) 1986.

It is preferable that the recombinant DNA molecule-containing an anti-sense gene of the invention further contain one or more selection marker genes which encode a selection gene product which confers on cells/tissues of a plant resistance to a chemical agent or physiological stress, such that plant cells transformed with the recombinant DNA molecule or plants containing such transformed plant cells may be easily selected using a selective agent. Any effective selective agent for which a resistance gene has been identified may be used to select transformed plant cells. The selective agent used to select plant cells transformed with the recombinant DNA of the invention could be said to fall within two broad non-mutually exclusive categories, a chemical agent and a physiological stress. Examples of selective agents which may be used to select plant cells are herbicides, antibiotics, toxic substances and plant diseases, in particular glyphosate, chlorsulfuron, kanamycin, hygromycin, methotrexate, and bleomycin, and phosphinotricin. Preferred selection marker genes which may be used in the present invention to facilitate selection of transformed cells include the gene encoding the enzyme hygromycin phosphotransferase conferring resistance to hygromycin and the enzyme neomycin phosphotransferase (NPT II) which confers resistance to kanamycin.

Examples of selective agents which may be used to select male sterile plants produced using a recombinant DNA molecule of the invention include a chemical agent, such as a herbicide, which could be used on a commercial scale. Examples of herbicides for which a resistance gene has been identified which may be useful as selective agents for plants are glyphosate (described in Comai, L., Facciotti, D., Hiatt, W. R., Thompson, G., Rose, R. E., Stalker, D. M., 1985, Nature, Vol. 317, Pages 741–744), chlorsulfuron (described in Haughn, G. W., and Somerville, C. R., 1986, Mol. Gen. Genet., Vol. 210, Pages 430–434) and phosphinotricin (Murakami T, et al, Mol. Gen. Genet. 205:42–50, 1986).

Genes encoding proteins or polypeptides that can provide a distinctive phenotypic characteristic to plant cells such as a gene that encodes a protein providing a distinguishable color or morphology to plant cells and genes which encode proteins which confer stress tolerance such as the metallothiones gene may also be used as selection marker genes to facilitate the selection of transformed plants.

For a general reference on selective agents see Weising, K., Schell, J., and Kahl, G. Ann. Rev. of Genetics, 22:421–477 (1988).

The selection marker gene may be expressed in particular cells or constitutively in the entire plant depending on the nature of the selection gene product. The expression of the selection marker gene(s) is regulated by one or more selection marker Promoters. The selection gene marker promoters may be isolated using techniques known in the art and include constitutive promoters such as CaMV 35S.

To facilitate selection of plant cells transformed with a recombinant DNA molecule or male sterile plants containing a recombinant DNA molecule it is preferred that a selection marker gene be contained in the recombinant DNA molecule, most preferably linked to the DNA sequence contained in the recombinant DNA molecule. Where the recombinant DNA molecule contains more than one DNA sequence it is preferred that each DNA sequence be linked to a different selection marker gene. It is contemplated in some embodiments of the invention that at least two recombinant DNA molecules be used to produce a male sterile plant and in such embodiments it is preferable that each recombinant DNA molecule contain a selection marker gene preferably linked to the DNA sequence.

In a hybrid seed production scheme where there are alternating rows of male sterile plants and male fertile plants, it may be advantageous to carry out the final selection of male steriles in the field alongside the male fertile donors. Therefore it is desirable if the suitable male fertile donors are previously transformed to resistance to the selective agent to avoid having to selectively apply the selective agent to the rows of male sterile plants.

It is to be understood that a plant sought to be rendered male sterile need not be transformed with a selection marker gene that confers resistance to a chemical agent or a naturally occurring or artificially induced physiological or chemical stress if this gene is native to the plant.

The recombinant DNA molecule containing an anti-sense gene of -he present invention preferably also contains a termination sequence and/or other transcription regulation signals. Examples of termination sequences which may be used in the recombinant DNA molecules of the invention are the nos terminator found in pRAJ-221 (Clonetech Laboratories, Palo, Alto, Calif.).

A detailed description of the isolation and identification of sense genes which are only expressed in cells/tissues of a plant that are essential are essential to pollen formation and/or function and pollen specific promoters is set out below:

To isolate sense genes which are only expressed in cells/tissues of a plant that are essential to pollen formation and/or function and pollen specific promoters, a genomic library of plant DNA may be constructed from DNA isolated from fresh young leaves according to standard methodology (*Molecular Cloning, a Laboratory Manual* Maniatis, T., Fritsch, E. F., and Sambrooks, J., Cold Spring Harbour Laboratory, Cold Spring Harbour, New York, 1982) and screened with probes derived from several tissues, one of which is made from RNA specific to cells/tissues of a plant that are essential to pollen formation and/or function (hereinafter referred to as, pollen specific RNA). The other probes should be made from RNA from different tissues so as to represent genes expressed in tissues of the plant that would not be expected to include genes that are expressed in cells/tissues of a plant that are essential to pollen formation and/or function. Examples include but are not limited to such tissues as leaf, roots, seeds, stigma, stem and other organs. Some genes are expressed in all tissues and some only in a restricted number of tissues, by comparison of many plant tissues it is possible to isolate genes expressed exclusively in cells/tissues of a plant that are essential to pollen formation and/or function.

Pollen specific RNA may be isolated from cells/tissues of a plant that are essential to pollen formation and/or function that are at the early to late uninucleate stage. Although it is possible to isolate pollen specific RNA at other stages, isolation of the pollen specific RNA may be technically difficult at earlier developmental stages; older cells may have limited nuclear gene activity; and, promoters may not be suitable for use as described in the present invention. For a detailed description of the isolation of pollen specific RNA see Example 1A herein.

Pollen specific RNA may be labelled for the purpose of detection. It is convenient to make radioactive cDNA by using the pollen specific RNA and AMV reverse transcriptase in the presence of random hexanucleotide primers and alpha-[$^{32}$P] -dCTP. Probes are used for hybridization to nitrocellulose plaque lifts of plates containing the clones of the genomic library. Clones that can be identified as strongly hybridizing only to pollen specific cDNA and not cDNA from any other tissue examined are chosen. These clones are plaque purified and grown for DNA isolation. Alternative techniques for manipulation of DNA and RNA as well as recombinant DNA, growing and isolating clones can be found in standard laboratory manuals, such as *Molecular Cloning, A Laboratory Manual* (Maniatis, T., Fritsch, E. F., and Sambrook, J., Cold Spring Harbour Laboratory, New York, 1982).

For applications where the genomic DNA sequence of L4, L10, L16 or L19 from *Brassica napus* are used to carry out certain aspects of this invention, the preferred method to obtain a sense gene that is essential to pollen formation and/or function is to synthetically produce a homologous DNA sequence according to standard methodology (see Gait, M. J., Ed., {1984} Oligonucleotide synthesis, a practical approach, pp 1–22, IRL Press, Oxford, U.K.), label the sequence for the purpose of detection and use the labelled sequence to screen a *Brassica napus* genomic library produced according to the methods described.

The identity of the promoter and coding region of a given genomic clone is determined by restriction mapping and hybridization analysis. This may be accomplished by hybridization of cDNA probes made from pollen specific RNA with restriction fragments of the DNA clones immobilized on nitrocellulose. Restriction endonuclease fragments which contain both the coding region and regions of DNA on either side of the coding region are isolated by sub-cloning in appropriate vectors. Once isolated, it is convenient to use techniques such as S1 mapping and DNA sequencing to obtain exact coding regions and restriction sites within the sub-cloned DNA. This analysis is easily accomplished once the polarity with respect to gene transcription is known.

In order to determine the polarity of transcription of a sense gene individual restriction fragments may be sub-cloned in commercially available vectors such as pGEM3, pGEM4,or pGEM3Z, pGEM4Z (available from Promega Biotech, Madison, Wis., USA). By using these vectors one is able to generate single stranded RNA probes which are complementary to one or the other strands of the DNA duplex in a given sub-clone. These strand specific probes are hybridized to mRNA, in order to establish the polarity of transcription. Among these probes, one can isolate those. probes which hybridize with and hence are complementary to the mRNA. Using this information it is possible to clearly determine from what DNA strand of the double-stranded genomic DNA molecule the sense mRNA has been transcribed.

In order to delineate and isolate the promoter DNA sequences of a given genomic clone the pGEM series of vectors can be used for the uni-directional deletion of sequences from the individual sub-clones in hybridization-protection experiments. Detailed descriptions of these experimental procedures can be found in a number of laboratory handbooks and in the manufacturers technical notes supplied with the pGEM series of vectors. These experiments will clearly establish the promoter and coding regions of the pollen specific genomic clones.

The sequence of individual deletions in the pGEM vectors can be determined by dideoxy sequencing of plasmid minipreps as described in the manufacturer's technical notes. Deletion sub-clones that are deleted to very near the start of transcription or specific restriction fragments that encompass the promoter region or the promoter region and the start of transcription are chosen for the construction of genes that are expressed only in developing microspores of pollen bearing plants. Usually the promoter fragment is inserted upstream of a terminator such as the nos terminator found in pRAJ-221 (available from Clonetech Laboratories, Palo Alto, Calif.) and specific restriction fragments which are to be transcribed into anti-sense RNA are inserted between the promoter and terminator sequences. The entire construct is verified by combination of sequencing and restriction digests. The anti-sense gene thus constructed and verified may be inserted in T-DNA based vectors for plant cell transformation. T-DNA vectors that contain a selectable marker are preferred. It is to be understood that the anti-sense gene can be constructed in a variety of ways depending on the choice of vectors, restriction enzymes and individual genes used. For example, it may be convenient to insert restriction fragments intended to be transcribed into anti-sense RNA into a T-DNA based vector to which a promoter and terminator structure have been previously added. Alternatively, it is possible to insert a promoter fragment upstream of a coding region and terminator that has been previously added to a T-DNA based vector. In addition, it may be desirable in some crops not to insert the anti-sense gene into a T-DNA based vector but rather into a vector suitable for direct DNA uptake. Promoters other than pollen specific promoters can be used and joined with specific restriction fragments of genes and terminators provided that these promoters function in cells and/or tissues essential to pollen formation and/or function.

In accordance with a second embodiment of the invention, a method is provided for the production of a male sterile plant by transforming a plant with a recombinant DNA molecule comprising a pollen specific promoter as hereinbefore described, and a DNA sequence which encodes a gene product which renders a cell/tissue essential to pollen formation and/or function susceptible to a chemical agent or physiological stress. Such a recombinant DNA molecule can be introduced into a plant wherein all the cells of the plant in which the recombinant DNA molecule is not expressed are resistant to the chemical agent and/or physiological stress.

In accordance with a third embodiment of the invention a method is provided for the production of a male sterile plant by transforming a plant with a recombinant DNA molecule comprising a pollen specific promoter as hereinbefore described and a DNA sequence which encodes a protein or polypeptide which is cytotoxic to a cell which is essential to pollen formation and/or function. By substance which is cytotoxic to a cell is meant a substance that when active disturbs the normal function of a plant cell/tissue preferably leading to cell death. Any, cytotoxic substance which is known to be encoded by one or more identifiable DNA sequences may be employed within the scope of this embodiment of the invention, including but not limited to ricin, abrin and diphtheria toxin. Thus, the DNA sequence may encode any substance which is cytotoxic to a cell that is essential to pollen formation and/or function including the genes encoding ricin, abrin and diphtheria toxin.

In addition to DNA sequences encoding cellular toxins such as ricin, abrin and diptheria toxin, the recombinant DNA molecule of the present invention may encode other cytotoxic substances including degrading or destructive enzymes such as ribonuclease, DNAse, ribozymes, lipase, or protease, substances that disrupt or de-stabilize cytoplasmic integrity such as polylysine or poly-proline, substances that disrupt or de-stabilize proteins or polypeptides which are essential to certain biosynthetic pathways in plant cells or interfere with the expression of such proteins or polypeptides.

In accordance with a fourth embodiment of the invention, the recombinant DNA molecule may comprise one or more DNA sequences which encode a gene product which renders a non-toxic substance cytotoxic to a cell/tissue which is essential to pollen formation and/or function. In particular, any identifiable DNA sequences encoding gene products which can convert a non-toxic to a cytotoxic substance can be employed within the scope of the invention. Examples of such DNA sequences include the following:

a) DNA sequences which encode indole acetamide hydrolase (IamH) which converts naphthalene acetamide to the plant growth regulator alpha naphthalene acetic acid (NAA) which is toxic to developing pollen grains, or converts indole acetamide to indole acetic acid (IAA) which is a plant growth regulator. One source of the enzyme IaMH is the bacterium *Agrobacterium tumefaciens* (Inze, D., et al, 1984, Mol. Gen. Genet. 194:265–74).

b) DNA sequences which encode the enzyme methoxinine dehydrogenase (MDH) which converts non-toxic 2-amino-4-methoxy-butanoic acid (methoxinine) to toxic methoxyvinyl glycine. One source of MDH is the bacterium *Pseudomonas aeruginosa* (Margraff, R., et al., 1980, Experimentia 36:486).

c) DNA sequences which encode the enzyme rhizobitoxine synthase which converts 2-amino-4-methoxy-butanoic acid to rhizobitoxine (2-amino-4-[2-amino-3-hydroxypropyl]-trans-3-butanoic acid) One source of the enzyme is the bacterium *Rhizobium japonicum* (Owens, L. D., et al., 1973, Weed Science 21:63–66).

d) DNA sequences which encode the tissue specific beta-glucuronidase enzyme which for example converts a non-toxic analog of glucuronic acid conjugated to a toxic substance such as chloramphenicol (Gluc-Camp) or glyphosate (N-[phosphomethyl]glycine) to cytotoxic substances such as chloramphenicol and glyphosate, respectively. Other toxic substances may be conjugated to glucuronic acid to provide a non-toxic analog of glucuronic acid.

Where the non-toxic substance does not occur naturally in the plant cell into which the recombinant DNA molecule of the fourth embodiment of the invention is to be introduced, the non-toxic substance may be introduced into the plant cell by spraying, watering or other similar means. The non-toxic substance may be produced in the cell by providing in the recombinant DNA molecule having a DNA sequence which encodes a gene product which renders the non-toxic substance cytotoxic to the cell, or in a second recombinant DNA molecule, a second DNA sequence which encodes the non-toxic substance. The non-toxic substance may also be introduced into the cell by providing in the recombinant DNA molecule having a DNA sequence which encodes a gene product which renders the non-toxic substance cytotoxic to the cell, or in a second recombinant DNA molecule, a second DNA sequence which encodes a gene product which converts a substance which is endogenous to the cell to the non-toxic substance. For example, a cell may contain a recombinant DNA molecule having a DNA sequence which encodes IamH (which converts indole acetamide to cytotoxic levels of indole acetic acid), and a second recombinant DNA molecule having a DNA sequence which encodes IamS. IamS converts tryptophan which is generally endogenous to plant cells, to indole acetamide which in turn is converted by IamH to cytotoxic levels of indole acetic acid.

The recombinant DNA molecule comprising one or more DNA sequences which encode a gene product which renders a non-toxic substance cytotoxic to a cell/tissue which is essential to pollen formation and/or function additionally contains one or more promoters to regulate the expression of the DNA sequences. If there is more than one DNA sequence in the recombinant DNA molecule the expression of the DNA sequences may be regulated by an identical promoter or the expression of each DNA sequence may be regulated by a different promoter. Preferably the expression of the DNA sequences is regulated by a pollen specific promoter as hereinbefore described so that the gene product which renders a non-toxic substance cytotoxic selectively interferes with the function and/or development of cells essential to pollen formation and/or function. Where the non-toxic substance is introduced into the plant cell by providing a second recombinant DNA molecule having a second DNA sequence encoding a second gene product which converts a substance which is endogenous to the cell to a non-toxic substance, the expression of the DNA sequence and the second DNA sequence may be regulated by either a pollen specific promoter, an inducible promoter or a constitutive promoter so long as there is selective interference with the function and/or development of cells essential to pollen formation and/or function. Preferably the expression of the DNA sequence encoding a gene product which renders a non-toxic substance cytotoxic is regulated by a pollen specific promoter and the expression of the second DNA sequence encoding a gene product which converts a substance which is endogenous to the cell to a non-toxic substance is regulated by a constitutive promoter, an inducible promoter or a pollen specific promoter, most preferably a pollen specific promoter. For a more detailed discussion of the above-mentioned promoters reference may be made to the discussion of promoters in reference to the recombinant DNA molecules containing anti-sense genes.

In accordance with a fifth embodiment of the invention, the recombinant DNA molecule comprises one or more DNA sequences which encode a gene product which may be converted into a substance which is cytotoxic to cells/tissues essential for pollen formation and/or function.

The recombinant DNA molecule of the second, third, fourth and fifth embodiments of the invention also preferably further contain one or more selection marker genes as hereinbefore described and termination sequences and other transcription regulation signals as hereinbefore described.

The following description sets forth, in general terms, the steps that can be employed to produce plants which are male sterile or carry the male sterile trait, using the recombinant DNA molecules of the invention. It is to be understood that these various steps may be accomplished by a variety of different procedures. In the following description of procedures, alternative ways to accomplish these steps are disclosed. Preferred procedures may be detailed below and in the examples. However, it is contemplated that other variations will be apparent to those skilled in the art.

The recombinant DNA molecules of the invention may be used to produce a plant which is male sterile or carries a male sterile trait, according to the following preferred steps:

(1) Introducing one or more of the recombinant DNA molecules, as contemplated herein for carrying out the invention, into the genome of one or more plant cells, of a plant selected from those species of pollen producing plants which are capable of being genetically transformed, preferably cells from which differentiated whole plants may be conveniently recovered;

(2) Selecting a plant cell into which the recombinant DNA molecule(s) is stably incorporated; and (3) Regenerating from the selected plant cell a plant which is male sterile or carries the male sterile trait.

A male sterile plant may be preferably produced by the above-mentioned steps by using the following recombinant DNA molecules of the invention in step (1):

a) A recombinant DNA molecule comprising a DNA sequence which encodes an RNA which when produced in a cell of a plant which is essential to pollen formation and/or function interferes with a gene which is essential to pollen formation and/or function and a pollen specific promoter or a constitutive promoter;

b) A recombinant DNA molecule comprising a DNA sequence which encodes an RNA which when produced in a cell of a plant which is essential to pollen formation and/or function interferes with a gene which is essential to the continued development and/or function of all metabolically competent cells of a plant and a pollen- specific promoter; and c) A recombinant DNA molecule comprising a DNA sequence which encodes a protein or polypeptide which when produced in a cell of a plant which is essential to pollen formation and/or function is substantially cytotoxic to the cell or renders a non-toxic substance cytotoxic to the cells, where the non-toxic substance is introduced into the cell by converting a substance endogenous to the cell to the non-toxic substance, and a pollen specific promoter.

A plant carrying a male sterile trait may be preferably produced by the above mentioned steps by using the following recombinant DNA molecules of the invention in step (1):

(a) A recombinant DNA molecule comprising a DNA sequence which encodes an RNA which when produced in a cell of a plant which is essential to pollen formation and/or function interferes with a gene which is essential to pollen formation and/or function and an inducible promoter;

(b) A recombinant DNA molecule comprising a DNA sequence which encodes a protein or polypeptide which confers on a cell of a plant resistance to a chemical agent or physiological stress and a pollen specific promoter; and (c) A recombinant DNA molecule comprising a DNA sequence which encodes a protein or polypeptide which when produced in a cell of a plant which is essential to pollen formation and/or function renders a non-toxic substance substantially cytotoxic to the cell, where the nontoxic substance is externally applied to the cell, or where the non-toxic substance is introduced into the cell by converting a substance endogenous to the cell of the non-toxic substance and an inducible promoter controls the expression of the protein or polypeptide which converts the endogenous substance to the non-toxic substance.

A plant carrying a male sterile trait may be rendered male sterile by exposing the plant to a sterility actuating agent which for example is an inducer in the case of (a) above, a chemical agent or physiological stress in the case of (b) above, or a non-toxic substance which is capable of being rendered cytotoxic (i.e. a cryptocytotoxic substance) to a cell which is essential to pollen formation. and/or function in the case of (c) above.

A recombinant DNA molecule may be introduced into a plant cell by any one of a variety of known methods preferably by first inserting the recombinant DNA molecule into a suitable vector and then using the vector to introduce the recombinant DNA molecule into a plant cell. As hereinbefore described a recombinant DNA molecule may additionally contain a selection marker gene which encodes a selection gene product which confers on a plant cell resistance to a chemical agent or physiological stress, or confers a distinguishable phenotypic characteristic to the cells such that plant cells transformed with the recombinant DNA molecule may be easily selected using a selective agent. Transformed plant cells thus selected can be induced to differentiate into plant structures which will eventually yield whole plants.

The use of Cauliflower Mosaic Virus (CaMV) (Howell, S. H., et al, 1980, Science 208:1265) and gemini viruses (Goodman, R. M., 1981, J. Gen. Virol. 54:9) as vectors has been suggested but by far the greatest reported successes have been with Agrobacteria sp. Horsch, R. B., et al, 1985, Science 227:1229–1231). Methods for the use of Agrobacterium based transformation systems have now been described for many different species. Generally strains of bacteria are used that harbour modified versions of the naturally occurring Ti plasmid such that DNA is transferred to the host plant without the subsequent formation of tumours. These methods involve the insertion within the borders of the Ti plasmid the DNA to be inserted into the plant genome linked to a selection marker gene to facilitate selection of transformed cells. Bacteria and plant tissues are cultured together to allow transfer of foreign DNA into plant cells then transformed plants are regenerated on selection media. Any number of different organs and tissues can serve as targets for Agrobacterium mediated transformation as described specifically for members of the Brassicaceae. These include thin cell layers (Charest, P. J., et al, 1988, Theor. Appl. Genet. 75:438–444), hypocotyls (DeBlock, M., et al, 1989, Plant Physiol. 91:694–701), leaf discs (Feldman, K. A., and Marks, M. D., 1986, Plant Sci. 47:63–69), stems (Fry J., et al, 1987, Plant Cell Repts. 6:321–325), cotyledons (Moloney M. M., et al, 1989, Plant Cell Repts 8:238–242) and embryoids (Neuhaus, G., et al, 1987, Thoer. Appl. Genet. 75:30–36). It is understood, however, that it may be desirable in some crops to choose a different tissue or method of transformation.

It is also understood that the successful transformation and recovery of a plant that contains these recombinant sequences may not always result in appropriate pollen specific expression. The transformation procedure results in the random insertion of foreign DNA such that "position effects" may override and suppress the activity of any introduced DNA. It is thus advisable to generate a number of individual transformed plants with any recombinant construct in order to recover individuals free from any limiting position effects. It may also be preferable to select plants that contain more than one copy of the introduced recombinant DNA molecule such that high levels of expression of the recombinant molecule are obtained.

It is known that the number of species of plants that have been successfully genetically transformed still represents a modest percentage of the total number of plant species that are of potential commercial interest. It is true, however that the number of species that have been transformed has increased steadily and there is every reason to expect that transformation systems can be developed for any crop of interest in due course. Routine transformation was initially achieved with species from two plant families: Solanaceae and Brassicaceae. Examples of species of commercial interest from within these families that have been transformed include: tobacco, *Nicotiana tabacum* L. tomato, *Lycopersicon esculentum* Mill, potato, *Solanum tuberosum* L., and petunia, *Petunia hybrida* (Solanaceae); Canola/Rapeseed, *Brassica napus* L., cabbage, broccoli, kale etc., *Brassica oleracea* L., mustards, *Brassica juncea* L., *Brassica nigra* L., and *Sinapis alba* L. (Brassicaceae).

Recently transformation has been reported of commercially important species from other families such as sugar beet, *Beta vulgaris*, (Chenopodiaceae), cucumber, Curcurbita sp. (Curcurbitaceae), cotton, Gossypium sp., (Malvaceae), sunflower, *Helianthus annuus* and lettuce *Lactuca sativa*, (Asteraceae=Compositae), and pea, *Pisum sativum*, soybean, *Glycine max* and alfalfa, Medicago sp (Fabaceae=Leguminoseae). Transformation has also been achieved with tree species such as poplar, Populus sp. (Salicaceae) and walnut, *Juglans nigra*, (Juglandaceae).

Transformation success with monocotyledonous species has not progressed as rapidly, since these species are generally not very susceptible to Agrobacterium mediated transformation. However, progress which has been noteworthy includes asparagus, *Asparagus officinalis*; gladiolus, Gladiolus sp., ( Lilaceae); corn, *Zea mays* and rice, *Oryza sativa* (Poaceae). The recent discovery that transformation with Agrobacterium can be accomplished by infecting germinating seeds without the requirement of regeneration from cell culture (Chee, P. P., et al., 1989, Plant Physiol. 91:1212–1218) opens new horizons for species that may be difficult to regenerate. Additionally, widespread studies on the use of particle guns to transfer microprojectiles coated in DNA into plant cells of species that are not readily susceptible to other methods holds great promise. It is expected that the present invention may be carried out with any one of the above species and with any other species that is capable of being genetically transformed.

The most widely used and generally successful methods of introducing foreign DNA into plants are dependent upon the use of an infectious agent, such as the *Agrobacterium tumefaciens* Ti plasmid, as a vector for delivery of the foreign DNA as hereinbefore described. However, it may be possible to use other methods, as well. Other methods that have been employed involve mechanical means such as direct DNA uptake, liposomes, electroporation (Guerche, P. et al, 1987, Plant Science 52:111–116) and micro-injection (Neuhaus, G., et al, 1987, Theor. Appl. Genet. 75:30–36). Recently the possibility of using microprojectiles and a gun or other devise to force small metal particles coated with DNA into cells has received considerable attention (Klein, T. M. et al., 1987, Nature 327:70–73). To date success with this and other mechanical methods has not been widely reported.

The method of choice will be dependant on the particular plant species and will be apparent to those skilled in the art. In those plant species where a successful transformation has not yet been demonstrated, it is anticipated that any new method of transformation developed may be used to insert the recombinant DNA molecules of the invention and the actual method of insertion of the genes will have little or no effect on the functioning of the crop production systems described herein.

It may also be possible to produce plants which are male sterile or carry the male sterile trait by fusing cells of a plant cell line containing cells having one or more recombinant DNA molecules of the invention with cells of plant species that cannot be transformed by standard methods. A fusion plan: cell line is obtained that carries a genetic component from both plant cells. Fused cells that carry the recombinant DNA molecule can be selected and in many cases regenerated into plants that are male sterile or carry the male sterile trait.

It is contemplated that some embodiments of the present invention may require that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequence or recombinant DNA molecules preferably the DNA sequences or the recombinant molecules are linked or located on the same chromosome, and then select from the progeny of the cross, plants containing both DNA sequences or recombinant DNA molecules.

Where at least two recombinant DNA molecules are necessary to interfere with the function and/or development of a cell of a plant that is essential to pollen formation and/or function (e.g. a first recombinant DNA molecule contains a first DNA sequence encoding a first gene product which converts a non-toxic substance to a cytotoxic substance and the non-toxic substance is introduced into the cell by means of a second recombinant DNA molecule which contains a second DNA sequence which encodes a second gene product which converts a substance endogenous to a plant cell to the non-toxic substance), the recombinant DNA molecules may be linked to prevent segregation of DNA sequences required to produce the desired effect. However it is preferred that a male sterile plant line be produced by crossing two plant lines each containing one of the recombinant DNA molecules which are not linked, which plant lines are otherwise isogenic. Each plant line is preferably made homozygous, for the respective recombinant DNA molecules to ensure that all the progeny receive a copy of each of the recombinant DNA molecules. Further, in some hybridization schemes discussed below, it may be preferable, to have the respective recombinant DNA molecules located in the same chromosome pair in each line. The choice of a chromosome pair containing a first recombinant DNA molecule in one plant line may be predetermined, randomly, and the other plant line may be adjusted so that a second recombinant DNA molecule is located on the same chromosome pair. For example, to produce a plant line which is homozygous for a first recombinant DNA molecule, a chromosome pair, in which a second recombinant DNA molecule is located is identified in a plant line, a transformed cell in which the first recombinant DNA molecule is incorporated on the identified chromosome pair is then selected, a plant is regenerated from the transformed cell, the plant is selfed, and a plant is selected which is homozygous for the trait encoded by the first recombinant DNA molecule, and the number of homozygous plants are increased, by selfing in isolation.

Methods of identifying the chromosome pair in which a recombinant DNA molecule is located and methods for producing homozygotes are discussed in detail below.

As indicated above, it may be desirable to produce plant lines which are homozygous for a particular gene. In some species this is accomplished rather easily by the use of anther culture or isolated microspore culture. This is especially true for the oil seed crop *Brassica napus* (Keller and Armstrong, Z. Pflanzenzucht 80:100–108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

Two techniques may be used to produce plant lines which carry genes that segregate in a similar fashion or are on the same chromosome or a set of chromosome pairs. One may be a simple crossing strategy in which two transformants that are homozygous for a single inserted gene are crossed to produce F1 seed. The progeny plants from the F1 seed (F1 plant generation) may be crossed with a recipient plant and the segregation of the two inserted genes is determined (F2 plant generation). For example, where the IamH and IamS genes are the inserted genes, the F1 plants grown from the F1 seed will be male sterile. If the original transformants are homozygous for a single inserted gene, when crossed with a non-transformed plant to produce F2 seed, the F2 plants will be 100% male fertile if the two transformants originally used for the production of the F1 seed carried the IamH and the IamS genes on the same chromosome or in the same linkage group. If the genes are in separate linkage groups or on different chromosomes, a variable degree of male sterility will be seen, in theory 25% of the plants will be male sterile if the genes segregate completely independently of each other. This approach allows for the selection of breeding lines from the homozygous transformed plant lines that contain the IamS and IamH genes which will segregate substantially 100% in the hybrid seed sold for commercial use.

An alternative strategy may make use of extensive genetic maps available for many commercially grown crops and the many easily scoreable markers that are known for most linkage groups or chromosomes. In some cases, linkage groups and chromosomes may be equivalent, whereas in others, there may be more than one linkage group assigned to each chromosome. When there is a marker for each chromosome, identification of the chromosome into which the recombinant gene has been inserted is relatively simple. A cross is made between each individual transformant and a recipient plant that allows for visualization of the marker(s).

If there are scoreable markers that have been localized to each of the chromosomes in the plant, and the markers are scoreable in the generation produced by this cross, one can localize the segregation of the inserted gene with the marker, thereby establishing the chromosomal location of that gene. This therefore allows for the chromosomal or more importantly the linkage group with which the inserted gene segregates. Many crops such as corn, tomato and many cereal crops have extensive genetic maps that allow for the identification of the chromosome containing the inserted gene. It is contemplated that as more detailed chromosome maps are made, especially with the use of RFLP (restriction fragment length polymorphism) maps, the assignment of inserted genes to particular chromosomes will easily be done for most commercial crop species.

As a means of confirmation, or in plant species where chromosomal markers are not known, it is possible to use a technique called pulse-field electrophoresis (originally, described by Schwartz and Cantor, Cell, 37:p67; 1984) to determine if different transformed plants contain inserted genes on the same chromosome. Pulse-field electrophoresis is a technique that can separate large DNA pieces, even chromosomal size, into a reproducible pattern on a gel. When this is done, it is possible to process this gel such that the chromosome spots can be analyzed by southern blotting techniques, localizing the inserted gene to a chromosome spot. When the entire population of primary transformants are analyzed in this fashion, it is a simple task to choose the two transformants that carry the inserted genes on the same chromosome spot.

As hereinbefore mentioned, after the recombinant DNA molecule(s) is introduced into the genome of a plant cell, a plant cell having a recombinant DNA molecule stably integrated in its genome is selected. This selection step may be facilitated by incorporating a selection marker gene in the recombinant DNA molecule such that plant cells transformed with the recombinant DNA molecule may be easily selected using a selective agent as hereinbefore described. A preferred selection marker gene is neomycin phosphotransferase (NPT II) which confers resistance to kanamycin and the antibiotic G-418. Cells transformed with this selection marker gene may be selected for by testing in vitro phosphorylation of kanamycin using techniques described in the literature or by testing for the presence of the mRNA coding for the NPT II gene by Northern blot analysis in RNA from the tissue of the transformed plant.

Expression of the recombinant DNA molecules of the invention in transformed plant cells may be monitored using Northern blot techniques. Single stranded RNA probes which are homologous to transcripts of the coding sequences of a recombinant DNA molecule(s) may be used to detect for the presence of the recombinant DNA molecule in a plant cell or tissue so that the expression of the coding sequence can be ascertained. It is preferable to use agarose gel electrophoresis to separate transcripts according to size under denaturing conditions. In the case where pollen specific gene expression of the coding sequence is sought to be accomplished it is advisable to test for the expression of the coding sequence in the cell type whose function and/or development is to be interfered with and in other tissues, such as leaves, roots, etc., so that tissue specific gene expression of the recombinant DNA molecule in such cell types can be verified.

The presence of a stably integrated recombinant DNA molecule in the genome of the plant cell may also be ascertained by using Southern blot techniques. In this procedure, total cellular or nuclear DNA is isolated from the transformed plant or plant cell and preferably digested with a restriction enzyme, thereby giving rise to discrete fragments. These discrete fragments may be detected in the nuclear or total DNA of the transformed plant or plant cells by employing standard gel electrophoresis or hybridization techniques.

The formation of microspores in plants which contain the recombinant DNA molecule(s) of the invention and which are male sterile, is first monitored by visual microscopic examination of the anther structure. As maturation of the flower occurs, anther formation is expected to be delayed or completely inhibited such that no mature pollen grains are formed or released.

It will be appreciated that plants produced using the method for producing male sterile Slants of the present invention may display varying degrees of male sterility. This may be a result of the nature of the plant cell transformed or of the chance positioning of the recombinant DNA molecule in the genome of the plant cell.

The following description of the invention sets forth, in general terms, the steps that can be employed to increase the number of male sterile plants and plants carrying the male sterile trait and to produce restorer plants, hybrid seed, hybrid seed with restored fertility and hybrid seed yielding a mixture of male fertile and male sterile plants. It is to be understood that these various steps may be accomplished by a variety of different procedures. In the following description of procedures, alternative ways to accomplish these steps are disclosed. Preferred procedures may be detailed below and in the examples. However, it is contemplated that other variations will be apparent to those skilled in the art.

As hereinbefore mentioned, the invention relates to hybrid seed having a genome comprising one or more of the recombinant DNA molecule(s) of the invention for producing plants which are male sterile or carry the male sterile trait and to seed of plants grown from the hybrid seed. The invention is also directed to a mixture of fertile and sterile hybrid seed and to seed of plants grown from said hybrid seed. The invention is also directed to hybrid seed having a genome comprising one or more of the recombinant DNA molecules of the invention for producing a male sterile plant and a corresponding restorer gene product for restoring fertility in the seed and Us seed of plants grown from the hybrid seed.

To produce hybrid seed on a commercial scale from a plant which is male sterile or carries the male sterile trait, the number of such plants must be increased or maintained and crossed with a suitable male fertile parent line.

A plant which carries the male sterile trait may be more readily maintained because such plant will not self-pollinate unless it is treated with a sterility actuating agent which renders the plant substantially sterile. For example, in a plant containing a recombinant DNA molecule having a DNA sequence which encodes a gene product that renders a cell susceptible to a chemical agent or physiological stress and having a pollen specific promoter, the plant will be rendered substantially male sterile by treating the plant with an actuating agent, namely the chemical agent or physiological stress. Accordingly, plants which carry the male sterile plant are preferably maintained by selfing, selecting from the selfing progeny a plant which is homozygous for the male sterile trait, and increasing the number of plants which are homozygous for the male sterile trait by selfing in isolation over a number of generations. Selection for a plant which is homozygous for the male sterile trait may also be carried out by the procedures discussed above.

A plant which is substantially male sterile is preferably maintained by crossing the male sterile plant with a suitable male fertile plant, obtaining seed from plants resulting form the cross, growing plants from the seed and selecting the plants which are male sterile from among the plants grown from the seed. This process may be repeated over a number of generations until the desired number of male sterile plants is obtained.

A plant which carries the male sterile trait may also be maintained by the latter method.

To facilitate selection of male sterile plants in the "maintained" plants, the recombinant DNA molecule(s) used to produce the male sterile plant should preferably comprise a selection marker gene and preferably a section marker gene is linked to a DNA sequence(s) contained in the recombinant DNA molecule as hereinbefore described.

A suitable male fertile plant for the purpose of crossing with a male sterile plant to increase the number of male sterile may be, but is not limited to, a plant of the same inbred line from which the male sterile plant is derived. In some instances referred to below, maintenance of the male sterile line can be produced simply by selfing in isolation.

According to another scheme the number of male sterile plants may be increased by clonal propagation using tissue explants thereof, or other in vitro propagation techniques.

Where cost is warranted, and maintenance cannot be readily accomplished as discussed above, transformed plant cells may be grown in culture according to routine methodology to produce a cell line. A cell line may be regenerated according to routine methodology to increase and maintain the male sterile cell line. Routine methods for culturing cell lines and regenerating transformed plants from cell lines is described in standard plant tissue culture hand books. (*Plant Tissue and Cell Culture,* Green, C. E., Somers, D. A., Hackett W. P., and Biesboer, D. D. Eds, 1987, Alan R. Liss, Inc., New York, *Experiments in Plant Tissue Culture,* Dodds, J. H. and Roberts, L. W. Eds, 1985, Cambridge University Press, or *Cell Structure and Somatic Cell Genetics of Plants,* Vasil, I. K., Scowcroft, W. R., and Frey K. J., Eds., 1984, Academic Press, New York, *Handbook of Plant Cell Culture,* Vol 1–4, Evans, D. A., Sharp, W. R., Ammirato, P. V., and Yamada, Y. Eds.,1984–1986, Macmillan, New York, *Bio-technology in Agriculture and Forestry,* Vol 1 and 2, Bajaj, Y. P. S. Ed., 1986, Springer-Verlag, Berlin, or *Plant Propagation by Tissue Culture—Handbook and Directory of Commercial Laboratories,* George, E. F., and Sherrington, P. D., 1984, Eastern Press, Reading).

Production of hybrid seed may be accomplished by pollination of male sterile plants with pollen derived from selected male fertile plants. Pollination can be by any means, including but not limited to hand, wind or insect pollination, or mechanical contact between the male fertile and male sterile plant. For production of hybrid seeds on a commercial scale in most plant species pollination by wind or by insects are preferred. Selection of plants for pollen donation is determined by standard crossing of different plants with subsequent analysis of the progeny and selection of lines with the best combining ability and superior agronomic traits. Restoration of fertility in the hybrids may be accomplished by using the methodology detailed below.

For certain crops of interest, such as vegetables, it may only be the leaves, stems or roots of the plant that are sold commercially. Therefore, even though the recombinant DNA molecule(s) which renders the plant male sterile may be inherited and expressed in the hybrid plant it is not necessary to overcome or restore male fertility in the seed of the hybrid plant. However, for other crops, the commodity of commerce may be the seed or fruit produced by the hybrid plant. Thus for optimal commercial utility of the hybrid it may be desirable to produce hybrid seed that is fertile.

The invention contemplates a variety of recombinant DNA molecules that may be used to produce a male sterile plant. In a scheme where any such recombinant DNA molecule(s) consists of a single gene or linked genes, the gene(s) may segregate as a unit to produce a mixture of sterile hybrid seed and fertile hybrid seed. Similarly unlinked recombinant molecules may segregate to produce a mixture of fertile and sterile seed except, as discussed below, where the molecules are located on different chromosomes of the same chromosome pair. In outcrossing species, the plants which grow from the fertile seed present may allow full pollination of the male sterile hybrid plants. Therefore, it may be preferable to adopt a scheme to produce hybrid seed which is fully fertile. However in species which are relatively weakly out-crossing, male sterile hybrid plants will not be fully pollinated, thereby reducing the seed yield. Therefore, where the commodity of commerce is the seed produced by the hybrid plant, it may be desirable to produce hybrid seed which is fully fertile.

The invention contemplates methods for restoring fertility in hybrid plants produced in accordance with the methods of the invention. Specifically, the invention contemplates a method for restoring hybrid plants produced in accordance with the methods of the invention by incorporating into a male parent plant, a restorer recombinant DNA molecule containing a restorer gene which encodes a restorer gene product which compensates for a gene function that has been compromised by a gene product(s) encoded by a first recombinant DNA molecule(s) of the invention, or which negates the effect caused by a gene product(s) encoded by a first recombinant DNA molecule(s) of the invention, as discussed below. The male parent plant thus may act as a "restorer plant". The restorer plant may be made homozygous for the gene encoding the restorer trait to ensure that all progeny inherit a gene. The homozygous restorer plant may be "maintained" by selfing in isolation to produce a "restorer line". Selection for a plant that s homozygous for the restorer trait may be carried out, as described above, by conducting anther or isolated microspore culture of the genetically transformed plant carrying the restorer trait, or preferably by selfing the plant in isolation prior to selection.

The expression of a restorer gene may be regulated by any promoter that is active during the period of transcription of a first recombinant DNA molecule which encodes a gene product which substantially interferes with the function and/or development of a cell essential to pollen formation and/or function. It is preferred that the expression of the restorer gene be regulated by the same promoter used to regulate the expression of the first recombinant DNA molecule or any promoter that is highly active in tissues that are essential to pollen formation and/or function.

Methods for restoring fertility in hybrid plants which have integrated in the genome of their cells recombinant DNA molecules of the invention are discussed below.

The action of a, protein or polypeptide which is substantially cytotoxic to a cell of a plant which is essential to pollen formation and/or function, and which is encoded by a DNA sequence contained in a recombinant DNA molecule which is integrated in the genome of cells of a hybrid plant may be negated by regulating the expression of the DNA sequence encoding the protein or polypeptide. For example, an anti-sense gene to the gene encoding the protein or polypeptide may be incorporated into a male parent line.

In particular where the recombinant DNA molecule has a DNA sequence which encodes a protein or polypeptide which is substantially cytotoxic to a cell of a plant which is essential to pollen formation and/or function, the male sterile plant may be crossed with a suitable male fertile plant that has been previously transformed with a restorer recombinant DNA molecule. The restorer recombinant DNA molecule may contain a restorer DNA sequence which is in the anti-sense orientation to that of the DNA sequence encoding the cytotoxic protein or polypeptide and a promoter controlling the restorer DNA sequence which activates transcription of the restorer DNA sequence at about the time of transcription of the DNA sequence. The restorer gene product inhibits the expression of the DNA sequence encoding the protein or polypeptide in the hybrid plant. The promoter controlling -he expression of the restorer DNA sequence is preferably the same pollen specific promoter that controls the expression of the cytotoxic protein or polypeptides. Inducible and constitutive promoters may also be advantageously used to control the expression of the restorer DNA sequence.

A cytotoxic method of producing male sterile plants may involve the synthesis of proteins or polypeptides capable of substantially interfering with the function and/or development of a cell/tissue which is essential to pollen formation and/or function. Methods for restoring fertility in male sterile plants produced by cytotoxic methods involve the syntheses, in cells/tissues that are essential to pollen formation or function, of restorer gene products that specifically block, neutralize or destroy the proteins or polypeptides. If the recombinant DNA molecule integrated in the genome of a hybrid plant has a DNA sequence which encodes a cellular toxin, a restorer plant containing DNA sequences coding for a detoxifying molecule may be used to restore fertility. If the recombinant DNA molecule integrated in the genome of a hybrid plant has a DNA sequence which encodes a destructive enzyme, a restorer plant containing DNA sequences coding for a specific enzyme inhibitor may be used to restore fertility. If the recombinant DNA molecule integrated in the genome of a hybrid plant has a DNA sequence which encodes a cytoplasmic disrupting molecule, a restorer plant containing DNA sequences encoding a specific peptidase may be used to restore fertility. Specific examples of cytotoxic proteins or polypeptides and their restorer gene products are the proteinase enzyme trypsin and soybean or cowpea trypsin inhibitor; ribonuclease and a ribonuclease inhibitor; or a starch degrading enzyme such as alpha-amylase and an alpha-amylase inhibitor.

Fertility in a hybrid plant containing in the genome of its cells a recombinant DNA molecule having an anti-sense gene may be restored as follows. An anti-sense gene contained in a recombinant DNA molecule to be incorporated in the genome of a plant may be selected such that it contains sequences of a sense gene which are transcribed, but not translated, in an anti-sense orientation. The transcribed but untranslated sequence may include an untranslated 5' leader sequence, intervening sequences and an untranslated 3' sequence, or any substantial fragments of these sequences. It is to be understood that the sequences or fragments thereof may be naturally occurring or foreign sequences.

Thus, any hybrid plant produced from a cross with a plant containing such an anti-sense gene may be restored by crossing with a restorer plant that has been transformed with a modified form of the sense gene which does not contain the regions complementary to the anti-sense gene and therefore is not subject to the ante-sense regulation.

As described above, a plant carrying a male sterile trait may be produced by integrating various recombinant DNA molecules of the invention into the genome of a plant cell and regenerating the plant from the plant cell. The development and/or function of cells that are essential for pollen formation and/or function in the plant are interfered with only after the plant is exposed to a sterility actuating agent such as an inducer, a toxic agent or a cryptocytotoxic substance. Thus, restoration is inherent in growing plants produced from hybrid seed in the absence of the sterility actuating agent.

Where more than one recombinant DNA molecule of the invention is used to produce a male sterile plant, the recombinant DNA molecules may be inserted in the same chromosome pair in separate isogenic plant lines. The respective lines are preferably made homozygous for the respective recombinant DNA molecule(s)/gene prior to crossing the lines to produce a male sterile plant. Where a first and a second recombinant molecule are integrated into the same chromosome in the isogenic plant lines, a cross of these lines results in the first and second recombinant DNA molecules being located on separate chromosomes of the same chromosome pair in the male sterile plant. Consequently, when the male sterile plant is crossed with a suitable male fertile plant of a different line, both chromosomes of the chromosome pair segregate into separate F1 progeny with the result that the first and second recombinant DNA molecules are not expressed in the same plant. Thus, the F1 hybrid seed is fully fertile. If the two recombinant DNA molecules are integrated into different chromosomes in the male sterile plant, then a portion of the F1 hybrid seed will be male sterile since there is a 25% probability of co-segregation of the chromosomes containing both recombinant DNA molecules into the male sterile plant. This latter approach may be advantageous with respect to outcrossing species. When the F1 male fertile plants outcross, a portion of the F2 seed will inherit both chromosomes containing the first and second recombinant DNA molecules and consequently will be male sterile. Where the seed is -he commodity of commerce, it is advantageous for seed producing companies to use a scheme for hybrid seed production, where the saving of F1 hybrid seed is discouraged. The outcrossing in the F1 hybrid plants results in partial male sterility in the F2 generation, thereby reducing the seed yield of F2 plants, which is commercially desirable. An example of this method is as follows: a first male sterile plant line incorporating in its genome a recombinant DNA molecule having an IamH gene encoding IamH which converts non-toxic IAM to toxic levels of IAA, may be crossed with a second plant line having a genome incorporating a second recombinant DNA molecule having an IamS gene which converts tryptophan to IAM.

In a preferred method of the invention for producing hybrid seed a first male sterile plant line having a genome incorporating a recombinant DNA molecule having a first DNA sequence encoding a protein or polypeptide which renders a non-toxic substance substantially cytotoxic to a cell of a plant which is essential to pollen formation and/or function and a pollen specific promoter is crossed with a second plant line which contains a second recombinant DNA molecule having a second DNA sequence which encodes a second gene product which converts a substance which is endogenous to a plant cell to the non-toxic substance. Preferably, the first and second plant lines used in this method are isogenic and each line carries a homozygous loci for the first DNA sequence or the second DNA sequence. Most preferably the first and second DNA sequences are located on the same chromosome pair of the plant lines, such that in any cross of the two lines a single chromosome pair contains both the first and second DNA sequences. The first plant line is made male sterile by exposing the first plant line to the non-toxic substance. The protein or polypeptide encoded by the recombinant DNA molecule incorporated in the genome of the first plant line will render the non-toxic substance toxic in cells of the plant which are essential to pollen formation and/or function, thus producing a male sterile plant line. The male sterile, plant line also preferably has a selection marker gene linked to the first DNA sequence encoding the protein or polypeptide which renders a non-toxic substance cytotoxic to facilitate harvesting of the seeds having cells containing the first and second DNA sequences.

When the first male sterile plant line and the second plant line are crossed, the first male sterile plant line produces seeds having cells containing the DNA sequence encoding the non-toxic substance (e.g. IAM) and the DNA sequence encoding the protein or polypeptide (IamH) which renders the non-toxic substance cytotoxic (e.g. IamH converts IAM to toxic level of IAA). The seed having cells containing the first and second DNA sequences will produce male sterile plants which may be pollinated with a male fertile line to produce commercial hybrid seed. If the first and second DNA sequences are located on the same chromosome or in the same linkage group, the DNA sequences will segregate completed in the F1 hybrid seed and the hybrid seed will be substantially male fertile.

Advantage is taken in the above-mentioned preferred method of the fact that most plant species produce, per plant, many hundreds of seeds. In oilseed Brassica for example, one plant, under normal conditions can produce one thousand seeds. Using the method described above, one can expect a thousand-fold increase in seeds per unit area sprayed with the non-toxic substance. That is to say that, for example, when two isogenic lines are produced that carry the IamS and IamH genes, the first pre-production step involves the use of NAM to cause male sterility in the plant line that carries only the IamH gene. When cross pollinated with the pollen from the plant that contains the IamS gene, one can expect up to one thousand seeds per unit area, each seed capable of growing into a male sterile plant. When these seeds are planted and crossed with a male sterile plant, one can expect one thousand seeds per unit area. Therefore, if one were to plant one acre of the plant line carrying the IamH gene and the pollinator carrying the IamS gene, this acre would need to be sprayed with NAM. From this one acre however, enough seed would be obtained to grow 1000 acres of male sterile plants and pollinators, and from these 1000 acres, enough hybrid seed with restored fertility would be obtained to plant 1,000,000 acres of hybrid crop. The amount of management required to produce this hybrid seed is reduced over conventional methods because of the pre-production amplification step employed. If the IamH gene is linked to a herbicide resistance gene, one can plant the fields randomly to ensure high rates of cross pollination and use the herbicide to kill the pollinator plants after flowering. This method therefore allows for efficient hybrid seed production over methods where hybrid seed is harvested directly following the first cross pollination.

A particularly preferred embodiment of the above method is described in more detail below with reference to FIGS. 17 and 18. As illustrated in FIG. 17, the method employs two plant lines which are homozygous, respectively, for the IamH gene (plant line A2) and the IamS (plant line A1) genes and otherwise isogenic. These genes are located on the same chromosome pair of the plant. Accordingly, plants produced from a cross of these two isogenic lines will contain the IamS and the IamH gene respectively on different chromosomes of a single chromosome pair. This will ensure that the two genes will segregate when this plant is crossed with a male fertile plant. To produce the hybrid seed, a two step procedure is used. The first step involves a pre-production of an isogenic male sterile line, the second step in the hybrid seed production itself. To accomplish the first step the following approach is used: The two isogenic lines A1 and A2 are planted in rows as shown, and when flowering starts, the plots are sprayed with NAM (naphthalene acetamide). This chemical is a non-toxic version of the plant growth regulator NAA, and the action of the IamH gene converts NAM to NAA. Under the control of the pollen specific promoter, the IamH gene only, is expressed in pollen of the A2 line, and as such NAA is only made in pollen of the A2 line. Since NAA is a plant growth regulator, normal anther and microspore development is altered, leading to male sterility in the A2 plant line when treated with NAM. The plants which contain the IamS gene under the control of the pollen specific promoter (plant line A1) are not affected by the NAM, since they are unable to convert NAM to NAA, therefore these plants remain fully male fertile and can cross pollinate the A2 plants which have now become male sterile after treatment with NAM. On the A2 line, seed is produced that contains both the IamH and IamS genes under the control of pollen specific promoters (plant seed A2/A1). The seed produced on the A2 line (plant seed A2/A1) is harvested. This harvesting can be done by harvesting specific rows. Alternatively, the IamH gene (A2) may be linked to a gene for herbicide resistance so that the herbicide can be used for the roguing of the plant line A1. Herbicide application takes place after flowering and will kill the A1 plants so that only seed that has the genotype A1/A2 is produced. The seed harvested from such a field will produce substantially 100% male sterile plants. The cross produces plants that express both the IamS and the IamH genes only in the pollen. This leads to the conversion of tryptophan, an amino acid normally found in plant cells to IAM (indole acetamide) via the IamS activity and finally to IAA (indole acetic acid) via the IamH activity. The molecule IAA is a plant growth regulator not normally found in substantial quantities in the developing pollen grains or anther of the plant. Since the IAA and the precursor Iam are small molecules that can be transferred from cell to cell via diffusion or active transport, altered growth regulator levels are seen throughout the anther. This altered growth regulator level leads to abnormality in pollen and anther development, producing a male sterile plant. This plant can be pollinated with a male fertile line leading to commercial hybrid seed. For the production of hybrid seed, the male sterile isogenic line can be planted in rows along side of a suitable male fertile plant, and the hybrid seed produced on the male sterile plant can be harvested. If the IamH gene is linked to a herbicide resistance gene, harvesting of hybrid seed is facilitated by using the herbicide to eliminate pollinator plants after cross pollination. The entire field can then be combined. All seed produced will therefore be hybrid. If the two genes (IamS and IamH) are located on the same chromosome or in the same linkage group, these two genes will segregate completely in the F1 hybrid seed. Since the plants will contain either the IamS or the IamH gene, but not both, the seed produced by this hybrid cross will be substantially 100% male fertile. Therefore the plants grown from the seed of this cross will be fully fertile and set normal levels of seed. The F2 seed that results from the harvest of this field however will contain a variable degree of male sterility, since in theory 12.5% or 2 out of 16 of the plants grown from this F2 seed will contain both the IamS and the IamH genes, as illustrated in FIG. 7. Therefore, particularly in poorly outcrossing species, the F2 generation will not be attractive to plant because up to 12.5% of the plants will not sat seed. Similarly, in outcrossing species which are not fully pollinated, a corresponding reduction in yield will be seen.

It is contemplated that as a variation of the above particularly preferred method, a number of different ways of producing the toxic molecule specifically in pollen can be envisioned. In all approaches, at least one step in the production of the cytotoxic molecule has to take place specifically within the pollen cells or anthers. For instance, it is possible to use a constitutively expressed IamS gene in a plant and to subsequently cross that plant with a plant that contains the IamH gene under the control of a pollen specific promoter such that Iam is produced in all cells of the plant, but the growth regulator IAA is produced only in pollen cells due to the action of the pollen specific IamH gene. Conversely, it is possible to have IamH constitutively expressed in a plant, and cross this plant with a plant that contains a pollen specific promoter driving the IamS gene. In this situation, the growth regulator IAA is only produced in pollen cells. It should be cautioned that in this case, one cannot use NAM to induce transitory male sterility in the plant that contains the IamH gene, since that application of NAM would be lethal to the plant. In this case then hand pollination would be the preferred way of combining those genes. With regards to these methods the preferred embodiment of the present invention places both the IamH gene and the IamS gene under the control of pollen specific promoters and preferably using the same pollen specific promoter or a pollen specific promoter whose expression substantially overlaps that of the other to each independently drive the expression of these two genes. Additionally, by linking the IamH gene to a selectable agent such as a herbicide, hybrid seed production is greatly facilitated. Any number of genes could be used to carry out this invention providing that the simultaneous production of two or more enzymatic or synthetic activities specifically in pollen leads to the production of a substance which is toxic or inhibitory to normal pollen growth or specifically interferes with anther or pollen development. This implies that one or more of these activities could be constitutive in the plant, but that the final combination of all enzyme activities be limited to pollen. It is also envisioned that one of these activities could be inducible by natural or artificial means such that sterility could be induced in plants. Specifically one embodiment of this method uses a plant line that carries a IamS gene under the control of an inducible promoter and a IamH gene under the control of a pollen specific promoter. These genes are preferably linked, but could be unlinked. When grown under inductive conditions, the plant becomes male sterile and can be pollinated by a suitable male fertile plant. The suitable plant could also carry a IamS gene under the control of a pollen specific promoter such that the progeny of this cross will be male sterile. These plants could then be crossed with a male fertile plant, producing hybrid seed. This seed would, depending on the location and number of the inserted genes, carry varying degrees of male sterility. It is also contemplated that a suitable male fertile plant be one that carries one or more copies of an anti-sense gene that is capable of selectively inhibiting the expression of one or more of these genes such that 100% fertility is recovered in the plants grown from the hybrid seed.

DETAILED DESCRIPTION OF THE FIGURES

In FIG. 1, a schematic representation of the production of the anti-sense vector PAL 1302 is shown. A plasmid containing the GUS gene (Beta-glucuronidase, described in Jefferson, R. A., Plant Molecular Biology Reporter, 1987, 5:387–405) in the anti-sense orientation flanked by the CaMV 35S promoter and the nos ter termination signal was obtained from the vetor pBI 221.1 (available from Clonetech Labotatories, Palo Alto, Calif., USA). The GUS coding sequence found between the CaMV 35S promoter and the nos ter of the vetor pBI 221.1 was excised and digested with the restriction enzymes Sma I and Sst I. The Sst I site was made blunt ended using Klenow fragment of DNA polymerase I and the blunt ended vector and GUS coding sequence were religated. A plasmid (pPAL 303) containing the Gus coding sequence inverted with respect to the direction of transcription of the CaMV 35S promoter was identified.

The binary vector PAL 1302 containing the anti-sense GUS gene was constructed using the vector pVU 1011 (obtained from The Plant Breeding Institute, Cambridge, UK) . pVU 1011 contains the hygromycin phosphotransferase coding sequence flanked by the CaMV 35S promoter and the nos ter inserted into the polylinker of the Agrobacterium binary vector Bin 19 described by Bevan, M., Nucl. Acids. Res. 1984, 12:8711–8721. The vector pVU 1011 can confer both hygromycin and kanamycin resistance to transformed plant cells. The insetion of the CaMV 35S promoter anti-sense GUS nos ter fragment into pVU 1011 was accomplished in such a way as to inactivate the NPT II gene of this vector and was performed a follows. A small Sph I-Pst I restriction fragment containing the right border (RB), the NOS promoter and the beginning of the NPT II coding sequence of pVU 1011 was first subcloned into the Sph I and Pst I sites preceeding the CaMV 35S promoter of pPAL 303 to form pPAL 306. Digestion of pPAL 306 with Sph I and Eco RI released a fragment consisting of the RB, the NOS promoter, the beginning of the NPT II coding sequence and the CaMV 35S promoter—anti-sense GUS noster construct. This fragment was then ligated into the Sph I sites of pVU 1011 by adding to the ligation pGEM-4Z (Promega Biotech, Madison, Wis., USA) cut with Eco RI and Sph I to provide a small fragment of polylinker as a bridge between the Sph I site of pVU 1011 and the Eco RI site of the isert from pPAL 306 respectively. The orientation of the insert was verified and a binary vector (PAL 1302) possessing a reconstructed RB fragment and a NPT II gene inactivated by the CaMV 35S promoter—anti-sense GUS gene-noster insertion was identified. This vector can confer only hygromycin resistance to plants and carries the anti-sense GUS gene.

In FIGS. 2*a–d* the orientation of the genes contained within the four microspore specific clones from *Brassica napus* are from 5' to 3'. As shown, the 5' region corresponds to the promoter region and is identified with a small arrowhead. The 3' region delineates the end point of transcription of the gene. Clones L4, L10 and L19 were used for the isolation of microspore specific promoter fragments and for the isolation of microspore specific coding regions. The non-transcribed regions are identified as a single thin line, while the regions of the clones that are transcribed are demarcated by a boxed area. Within this boxed area the portion of the transcribed DNA that represents the exon regions is demarcated by being filled in black while the intron sequences are left unfilled. The approximate regions of DNA sequenced for clones L10, L16 and L19 are shown by underlining. Restriction sites identified are those that are relevant to the constructs detailed below. The right and left arms of the lambda cloning vectors are not shown.

In FIGS. 3a–d, the complete DNA sequence of the clone L4 is shown along with the DNA sequence of the portions of the clones L10, L16 and L19 that are identified in FIGS. 2a–d. In FIG. 3a, clone L4, nucleotide 1 in the complete sequence is at the left-most Eco R1 site while nucleotide 8579 is at the first nucleotide of the right-most Eco R1 site. The start of transcription of gene 1 in clone L4 is nucleotide 235. The 5' and 3' intron splice sites are identified in boldface type. The start ATG codon is shown as well as the stop termination codon. The deduced amino acid sequence of the proteins encoded for by these genes are also shown. The end of transcription for gene 1 is approximately nucleotide 1427. The second gene in clone L4 is most likely non-functional due to a insertion and a deletion that occurs in the region of the promoter and first exon. This gene was not utilized for constructs. The third gene in clone L4 has a transcriptional start at position number 6298 in the DNA sequence and transcription ends at approximately nucleotide 7490. The ATG start codon, intron splice sites and termination stop codon are all identified as above. Vectors were constructed from this clone by using promoter fragments from both genes 1 and 2, as well as promoter fragments from genes 1 and 2 that contained the first exon and intron sequences and a short portion of the second exon for each of the genes. The specific promoter fragment constructs are detailed below.

Figures 2A, 2B:
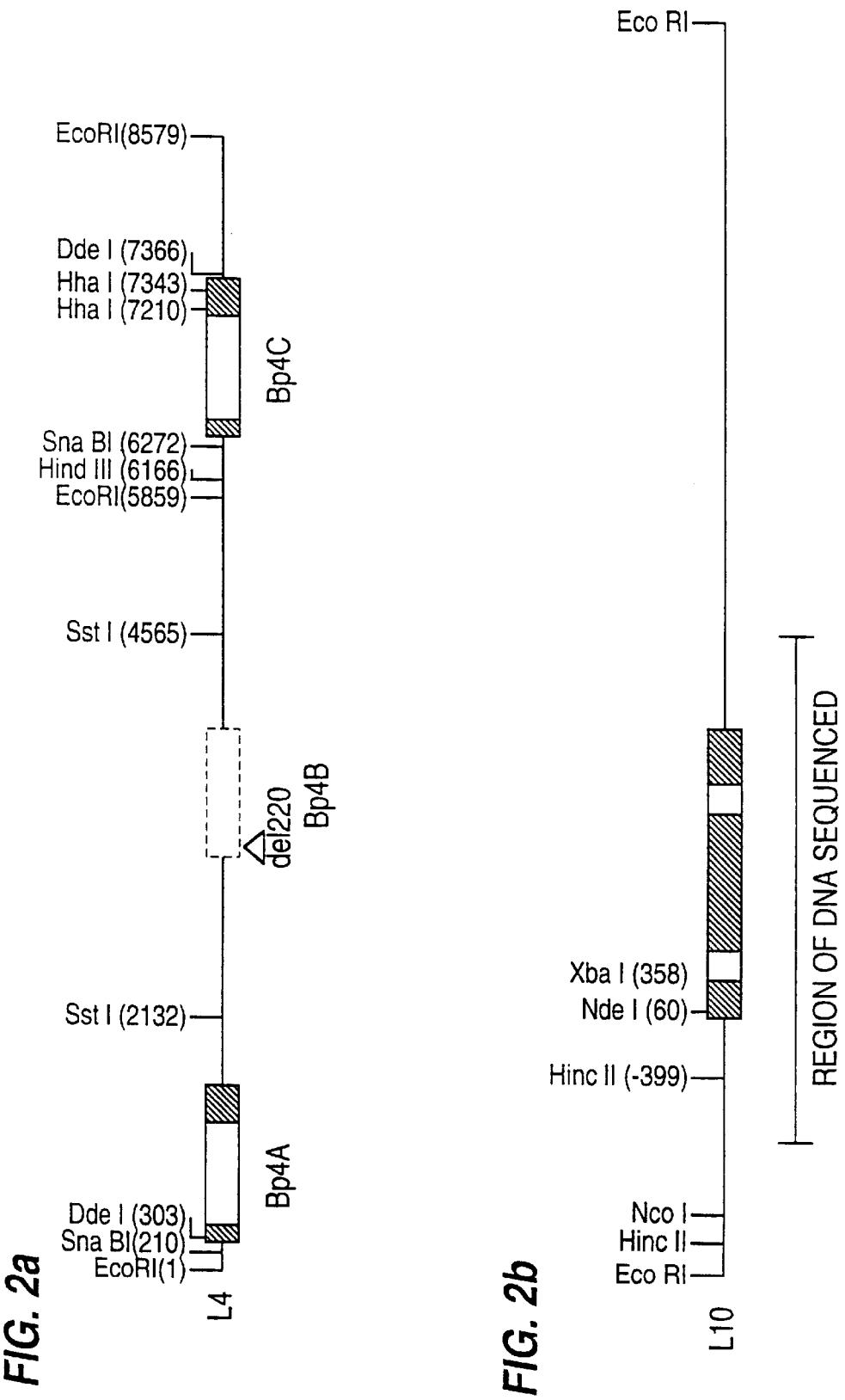
FIG. 2a is a schematic representation of a restriction map and coding region of clone number L 4, a microspore specific clone isolated from a *Brassica napus* genomic library. The clone contains three similar copies of a single gene. These genes are identified as Bp4A, 3p4B and Bp4C. The first (Bp4A) and third (Bp4C) genes are functional, the second gene has modifications chat most likely render it non-functional. The restriction map is made diagrammatically in that the non-transcribed regions are shown as a single line, while the transcribed regions are shown as a boxed area. The second gene (Bp4C) is identified on the basis of sequence homology and i-s shown as a boxed area with a dotted line. The notation "del 220" refers to an approximately 220 base pair deletion/rearrangement that has presumably inactivated the second gene (Bp4B) in this clone. Start of transcription is located at the leftmost side of each boxed area (except in the case of gene Bp4B) and exon and intron positions are noted by the exons being filled in with black and the intron positions being left unfilled. A small arrowhead is shown on the non-transcribed 5' region of each gene, this arrowhead serves to indicate the promoter region of each gene. Restriction sites are Identified such that the number of the first nucleotide of the restriction enzyme recognition site is shown. Not all restriction sites are shown, only those relative to the constricts detailed within are indicated. The genes are presented with the 5' region on the left side and the 3' region on the right side. The numeration of the DNA sequence is from left to right, 5' to 3' in all cases.
FIG. 2b is a schematic representation of a restriction map and coding region of clone number L 10, a microspore specific clone isolated from a *Brassica napus* genomic library. The clone contains a single gene. Start of transcription, exon, intron and promoter positions are noted as in FIG. 2a. Restriction sites are identified such that the number of the first nucleotide of the restriction enzyme recognition site is shown. The genes are presented with the 5' region on the left side and the 3' region on the right side. The numeration of the DNA sequence is from left to right, 5' to 3' in all cases.

In FIG. 3b, the nucleotide sequence of the region of clone L10 demarcated in FIG. 2b is shown. The start of transcription is at nucleotide 1. In this sequence the ATG start codon is at nucleotides 45–47, the first exon ends at nucleotide 315 the second exon starts at nucleotide 476 and extends to nucleotide 1586. The third exon starts at 1673 and extents approximately to nucleotide 1989, the precise end of transcription was not determined. The deduced amino acid sequence is also shown. For some promoter constructs the region of the clone 5' to the sequenced portion were used. The specific details of the constructs are listed below.

In FIG. 3c, the nucleotide sequence of clone L16 is shown. Clone L16 shows considerable homology to clone L10 specifically in the portions of the two clones that code for protein sequence. The intron sequences between the two clones differ considerably however. Clone L16 does not contain a 5' promoter region and as such was used only as a source of coding sequences for anti-sense RNA constructs. Nucleotide 1 demarcates an Eco RI site that occurs in a coding region of the DNA that is homologous to the first exon of clone L10. By homology, this coding region extends to nucleotide 124, where the first intron is located. This intron, which is located at the same relative position as the first intron of clone 10, is longer than the intron in clone L10 and extends to nucleotide 688. Nucleotide 689 is the start of the second exon and this exon, which shows strong homology to the second exon of clone L10, extends to nucleotide 1793. There is a second intron at this point and this intron extends to nucleotide 1909. The third exon starts at 1910 and extends to aproximately nucleotide 2210. The deduced amino acid sequence is also shown for specific regions of the clone that show considerable homology to clone L10. The precise nucleotide where transcription stops has not been determined.

Figures 2C, 2D:
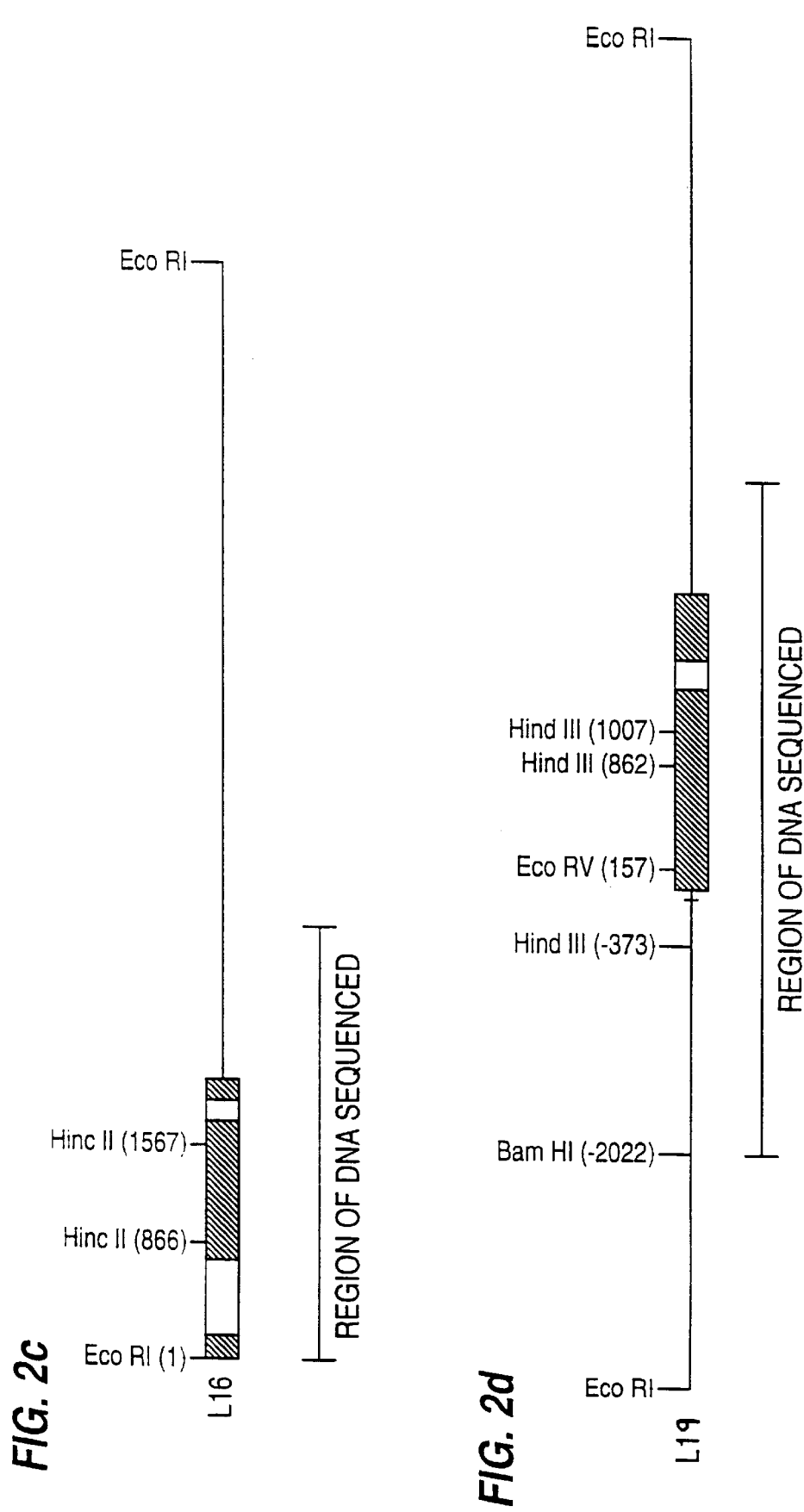
FIG. 2c is a schematic representation of the restriction map and coding region of clone number L 16, a microspore specific clone isolated from a *Brassica napus* genomic library. The clone contains a single gene that shows similarity to clone L 10. Intron and exon positions are noted as in FIG. 1. Restriction sites are identified such that the number of the first nucleotide of the restriction enzyme recognition site is shown. The genes are presented with the 5' region on the left side and the 3' region on the right side. The numeration of the DNA sequence is from left to right, 5' to 3' in all cases.
FIG. 2d is a schematic representation of the restriction map and coding region of clone number L 19, a microspore specific clone isolated from a *Brassica napus* genomic library. The clone contains a single gene. Start of transcription, exon, intron and promoter positions are noted as in FIG. 1. Restriction sites are identified such that the number of the first nucleotide of the restriction enzyme recognition site is shown. The genes are presented with the 5' region on the left side and the 3' region on the right side. The numeration of the DNA sequence is from left to right, 5' to 3' in all cases.

In FIG. 3d the nucleotide sequence of the region of clone L19 demarcated in FIG. 2d is shown. The start of transcription is located at position 1 in the sequence. The ATG start codon is at nucleotides 136–138 and the first intron starts at nucleotide 1201. This intron ends at nucleotide 1338 wherein the second exon starts. The end of transcription occurs at approximately nucleotide 2074. The deduced amino acid sequence is also shown.

In FIG. 4, the DNA sequences of three cDNA clones that are homologous to the genes contained in the clone L4 are shown. The DNA sequence of these three cDNA clones as well as the sequence of the correctly spliced transcribed regions of genes Bp4A and Bp4C in the genomic clone L4 are aligned, only the nucleotide differences within these clones are shown, nucleotides that are conserved between the sequences are only shown on the upper sequence. The asterisks shown in FIG. 4 mark the 5' end of the cDNA clones of cBp401, cBp405 and cBp408.

In FIG. 5, the partial nucleotide sequence of a cDNA clone that is homologous to the coding region of clone L10 is shown. This cDNA clone is approximately 1.3 Kb in length and has Eco R1 sites at she 5' and 3' ends of the cDNA sequence that were added via synthetic linkers in the cDNA cloning procedure.

In FIG. 6, the nucleotide sequence of the cDNA clone that corresponds to the coding region of clone L19 is shown. Identified in this sequence is the Eco RV site present at the 5' end of the transcribed region of L19. A portion of the poly A tail is shown. Not shown are the Eco RI sites that were added as linkers in the cDNA cloning procedure; these sites are present adjacent to the 5' and 3' ends of the cDNA clone.

In FIGS. 7 (a,b,c,d,e) the construction of 6 vectors containing promoter and promoter fragments from the clone L4 is described. The first step in the construction of these vectors was accomplished by first subcloning the Eco R1-Sst 1(nucl.1–2132) fragment containing the first gene of clone L4 (235 base pairs of promoter/exon/intron/second exon) in the commercially available vector pGEM-4Z(Promega Biotech, Madison, Wis., USA) using the Eco R1-Sst 1 sites of the polylinker of this vector. This plasmid was named pPAL 0402. The 2.7 Kb Eco RI fragment of clone L4 that contains the third gene (Bp4C) was then cloned into the Eco RI site of pGEM 4Z, leading to a plasmid called pPAL 0411. The plasmid pPAL 0402 was then digested with Eco R1 and the 2.7 Kb Eco R1 fragment from pPAL 0411(nucl. 5859–8579) that contains the gene number three (Bp4C) from clone L4 was added to it. Clones were recovered that contained this inserted 2.7 Kb Eco R1 fragment in both orientations relative to the promoter region of the first gene. A clone that contained this third gene fragment in a orientation such that the promoter from the third gene was opposite to the promoter in the first gene was chosen and called pPAL 0403. The plasmid pPAL 0403 contains the entire third gene from clone L4 oriented in such a fashion as to have the promoter region immediately adjacent to the 235 basepair promoter region of the first gene in pPAL 0403. This plasmid, pPAL 0403 was digested with Dde I, producing a fragment of approximately 1.9 Kb. The Dde I sites are located at nucleotides 303 and 7366. Because of the orientation of these fragments, digestion with Dde I produces a 1.9 Kb fragment. This 1.9 Kb fragment contains a copy of the third gene (Bp4C) oriented such that the direction of transcription of this third gene is from right to left, fused to the 235 base pair promoter fragment from the first gene of clone L4 (Bp4A) which is transcribed from left to right, ending in a Dde I site that is located 67 basepairs down stream of the major start site of transcription and precedes that ATG start of translation codon by 2 nucleotides. This 1.9 Kb Dde I fragment was made blunt with Klenow fragment and cloned into the Xba 1 site of the polylinker region of pGEM 4Z previously made blunt ended with Klenow fragment. The resultant plasmid pPAL 0408, was recovered and subsequently was digested with Sal 1 and Sst 1, which releases the cloned Dde 1 fragment bordered by on the left hand side, (nucl 7366) Sal 1 and on the right hand side (nucl 303 of this construct and contains a portion of the polylinker of pGEM 4Z containing the following unique sites: Bam HI, Sma I, Kpn I, and Sst I restriction enzyme sites. This Sal 1-Sst 1 fragment was cloned into the Sal 1-Sst 1 sites of PAL 1001. PAL 1001 is the binary vector Bin 19 (described by Bevan, M., Nucleic Acids Res., 1984, 12:8711–8721) to which has been added the nos ter polyadenylation signal as a 260 bp Sst 1-Eco R1 fragment isolated from the plasmid pRAJ 221 (available from Clonetech Laboratories, Palo Alto, Calif. USA) in the Sst 1-Eco R1 sites of the polylinker region of Bin 19. This nos ter is identified as a stippled box. The binary transformation vector that resulted from the insertion of the Sal I-Sst I fragment of pPAL 0408 into PAL 1001 was named PAL 1107. The details of the construction are shown in FIG. 7a. This vector has a copy of the third gene oriented such that the direction of transcription of this third gene is from right to left, fused to the 235 base pair promoter fragment from the first gene of clone L4 which is transcribed from left to right, followed by a polylinker with unique sites for the insertion of DNA which consist of: Bam HI, Sma I, Kpn I and Sst I followed by the nos ter signal. This vector has the feature in that additional 5' non-coding sequences were placed upstream to the 235 base pair core promoter on Bp4A, but these additional 5' sequences were in a opposite orientation. The provision of these sequences in this orientation does not affect the pollen specificity of the core 235 base pair promoter.

Figure 7A:
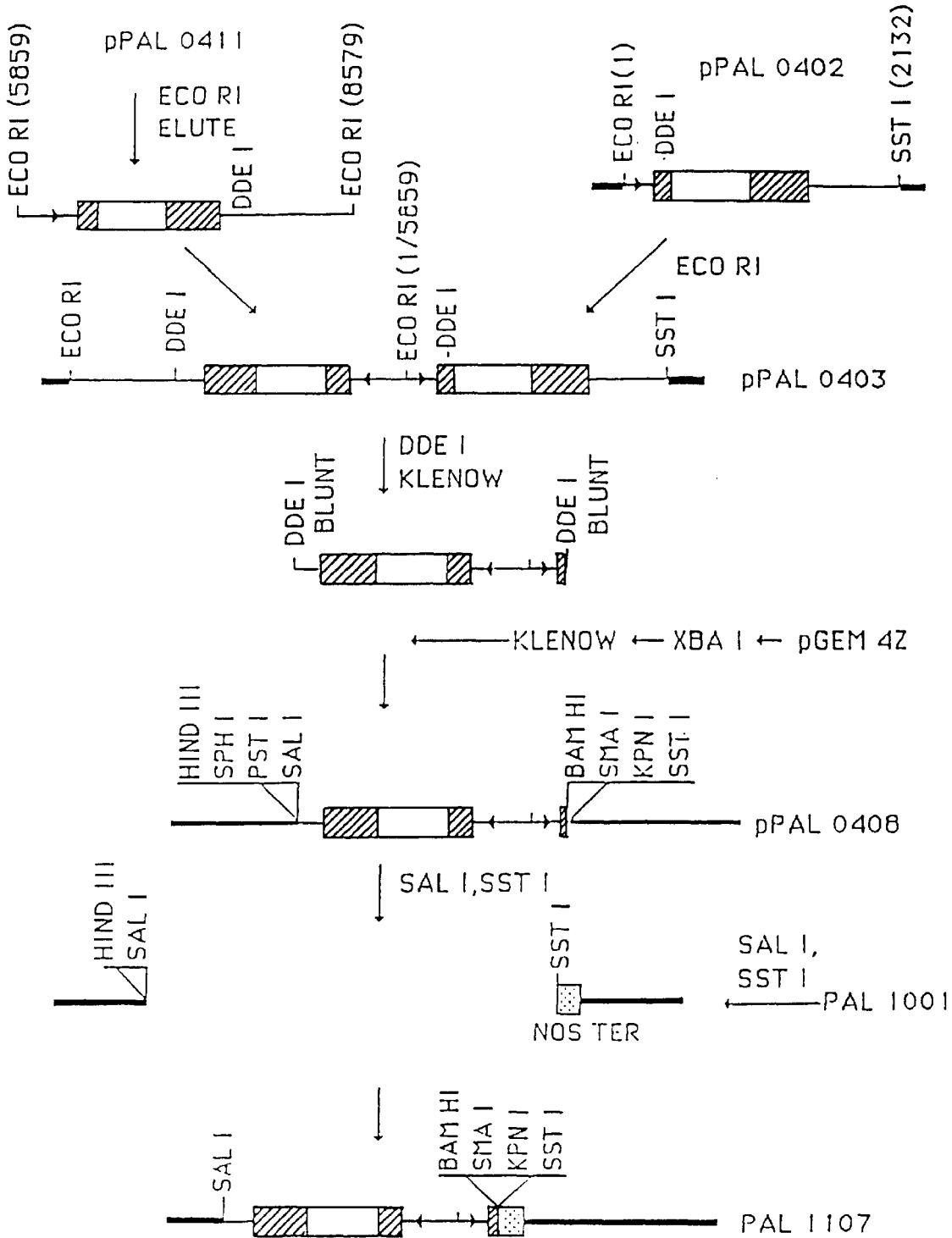
FIGS. 7A–7E.
Figure 7B:
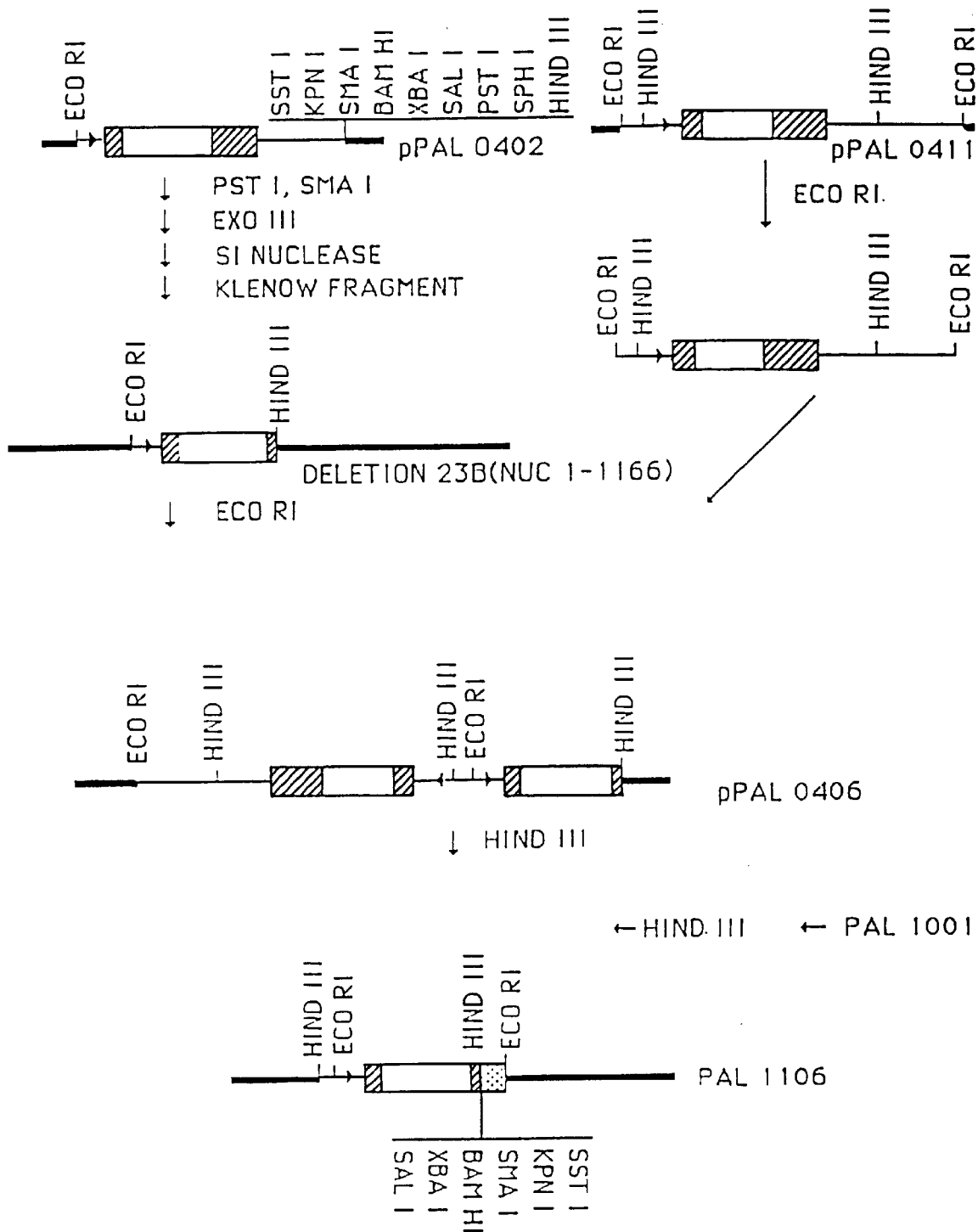

In addition to this vector, similarly structured vectors were made which contained essentially the same type of gene promoter arrangement but contained the intron of the first gene (Bp4A) of clone L4. Intron sequences in plant genes have been shown in some cases to play a role in gene expression. This intron containing vector was constructed by making a deletion series of the clone pPAL 0402. pPAL 0402 was first digested with Pst I and Sma I. Exonuclease III was used to unidirectionally digest the DNA as shown (FIG. 7b). After S1 nuclease treatment and repair with Klenow, the plasmid was relegated and clones that have had different portions of the coding regions of gene Bp4A digested out of them were recovered. Deletion subclones were sequenced. One was chosen for vector constructs. This is referred to as deletion 23B. This subclone represented a deletion that has most of the second exon of gene Bp4A removed but contains the intron splice site and first exon of gene Bp4A. This subclone contains a portion of the clone L4 that extends from nucleotide 1 to nucleotide 1166. To this subclone was added the 2.7 Kb Eco R1 fragment from pPAL 0411 that contains the third gene of L4 (Bp4C) in such an orientation that the direction of transcription of the third gene is from right to left (as in PAL 1107, pPAL 0408), fused to the 235 base pair promoter region from the first gene of clone L4 which is oriented to transcribe from left to right followed by the first exon of gene 1, the entire intron of gene 1 and 33 nucleotides of the second exon of gene Bp4A from clone L4. This plasmid containing deletion 23B and the 2.7 Kb Eco RI fragment containing the third gene fragment was named pPAL 0406. This plasmid was digested with Hind III, which yields a fragment containing a small portion of the promoter of the third gene as well as the entire promoter of the first gene, first exon, intron and a portion of the second exon. This Hind III fragment was inserted into the Hind III site of PAL 1001, resulting in the vector PAL 1106 (deletion 23B derived). This vector has in the following order, A portion of the promoter from the third gene in clone L4, the entire 235 base pair promoter of the first gene in clone L4, followed by the first exon, the intron and a portion of the second exon of gene 1 of clone L4, followed by a polylinker containing the following unique cloning sites: Sal I, Xba I, Bam HI, Sma I, Kpn I and Sst I and the nos ter polyadenylation signal. The construct is shown in FIG. 7b.

Additional constructs with the promoter regions of the genes contained in clone L4 were done in order to provide a number of suitable vectors that are useful for pollen specific expression of gene sequences. The three genes within clone L4 (Bp4A, Bp4B, Bp4C) show very near-exact DNA homology and this is most apparent between the first (Bp4A) and third (Bp4C) gene. The second gene (Bp4B) is a homologous copy that has undergone sequence changes that have appear to have lead to inactivation. The extensive similarity between the first, second and third genes in clone L4 is also maintained in the promoter region such that out of the first 235 nucleotides of the first and third gene promoter regions there are only 5 nucleotides that differ between them. Downstream of the TATA box in these two promoters the only difference between them is the presence of one additional nucleotide at the start of transcription. For example, comparison of Promoter 1, Bp4A, partially represented as: . . . TATGTTTtAAAA___ . . . with Promoter 3,Bp4C, partially represented as: . . . TATGTTTAAAA___ . . . shows that the transcribed region underlined and the single nucleotide difference in lower case. However, within the sequence of the first gene there is a nucleotide change that introduces a Dde I site (nucl 303) in the untranslated 5' leader sequence upstream of the ATG start codon that is not present in the untranscribed leader sequence of the third gene in clone L4. Chimeric promoter constructs were made which utilized this Dde I site in the first gene to combine with sequences from the third gene promoter. The region of the first promoter used for these constructs consisted of the sequences contained between the Sna BI site (nucl 21) near the TATA box to the Dde I site located immediately upstream of the ATG start codon in the first gene (nucleotide 303 is the first nucleotide in the recognition sequence for Dde I). The other region of this chimeric promoter (5' of the TATA box) was a fragment extending from the Eco R1 site of the third promoter (nucleotide 5858) to the Sna B1 site near the TATA box (nucleotide 6273). Therefore to facilitate construction of these pollen specific vectors, the following reconstructions were performed.

The Eco R1 to Dde 1 fragment that encompasses the promoter region of the first gene in clone L4 was isolated by first cutting pPAL 0402 with Dde 1, blunting with Klenow, and then cutting with Eco R1. The 235 base pair fragment corresponding to this region was cloned into the Eco R1-Sma 1 sites of pGEM 4Z. This plasmid (pPAL 0422), was then cut with Eco R1 and Sna B1. A DNA fragment that contained the Eco RI to Sna BI portion of the promoter for gene 3 in clone L4 was isolated by digesting pPAL 0411 with Eco R1 and Sna B1. This released an approximately 415 base pair Eco RI (nucl.5858) to Sna BI (nucl. 6273) fragment that represents most of the 5' region of the gene 3 promoter from clone L4 (the Sna B1 recognition site is 2 base pairs downstream of the TATA box). This Eco R1-Sna B1 fragment was used to replace the shorter Eco R1-Sna B1 fragment removed for the first promoter subclone (pPAL 0422), reconstructing a promoter fragment of approximately 550 base pairs. This plasmid is referred to as pPAL 0421. This chimeric promoter fragment contains 415 base pairs of the promoter of gene three in clone L 4, followed by approximately 99 Nucleotides of the first gene promoter/ untranslated leader sequence.

For construction of a pollen specific cassette vector, the following plasmids were first constructed. The first plasmid constructed contained the nos ter polyadenylation signal with a polylinker in front of the nos ter signal. This was accomplished by first isolating from pRAJ 221 the nos ter as a Sst 1-Eco R1 fragment and this fragment was cloned in pGEM 4Z using the Sst 1 and Eco R1 sites in the polylinker. This subcloned is referred to as pPAL 001. To pPAL 001, a fragment coding for neomycin phosphotransferase (NPT II) derived from the plasmid pRAJ 162 was added to it in the anti-sense orientation as follows: The plasmid pRAJ 162 contains the NPT II gene from the transposon TN 5 inserted as a Sal I fragment and bounded by a polylinker in the plasmid pUC-9 (which was obtained from the Plant Breeding Institute, Cambridge, UK). pRAJ 162 was digested with Hind III and Sma I. The DNA fragment containing the NPT II gene was isolated by elution from an agarose gel. pPAL 001 was digested with Hind III and Sma I and the NPT II gene fragment was inserted. The resultant plasmid was called pPAL 002 and had such orientation of restriction sites and the NPT II gene and nos ter as follows: HIND III, Pst I, Sal I, 3' end NPT II coding sequence 5' end, Sal I, Bam HI, Sma I, Kpn I, Sst I, nos ter, Eco RI. pPAL 002 was cut with Hind III and the size made blunt ended by the use of Klenow fragment. pPAL 0421 was digested with Hinc II and Pvu II, both of which leave blunt ends, and the promoter fragment was ligated into Hind III cut blunt ended pPAL 002. Plasmids were obtained that contained the promoter in both orientations relative to the nos ter signal. One plasmid was chosen with the proper orientation (5' promoter/anti-sense NPT II/nos ter) and was named pPAL 0419. pPAL 0419 has she following DNA fragments: A small (approx. 130 bp) of pGEM 4Z that contains the SP6 promoter, the 550 base pair chimeric promoter, the NPT II gene in the anti-sense orientation relative to the promoter, followed by the nos ter polyadenylation signal. This entire promoter/NPT II/nos ter construct is excisable by Eco RI. pPAL 0419 was digested with Eco RI, and the promoter NPT II nos ter structure was cloned into BIN 19 using the single Eco RI site in the polylinker of BIN 19. The resultant transformation vector was named PAL 1419. In addition to the anti-sense NPT II gene, the vector contains a constitutive NPT II gene under the control of the nos promoter. This vector therefore confers resistance to kanamycin in all cell types with the exception of pollen, cells where the gene expression from the constitutive promoter is inhibited by the anti-sense RNA produced from the promoter/NPT II/nos ter construct contained in PAL 1419.

Figure 7C:
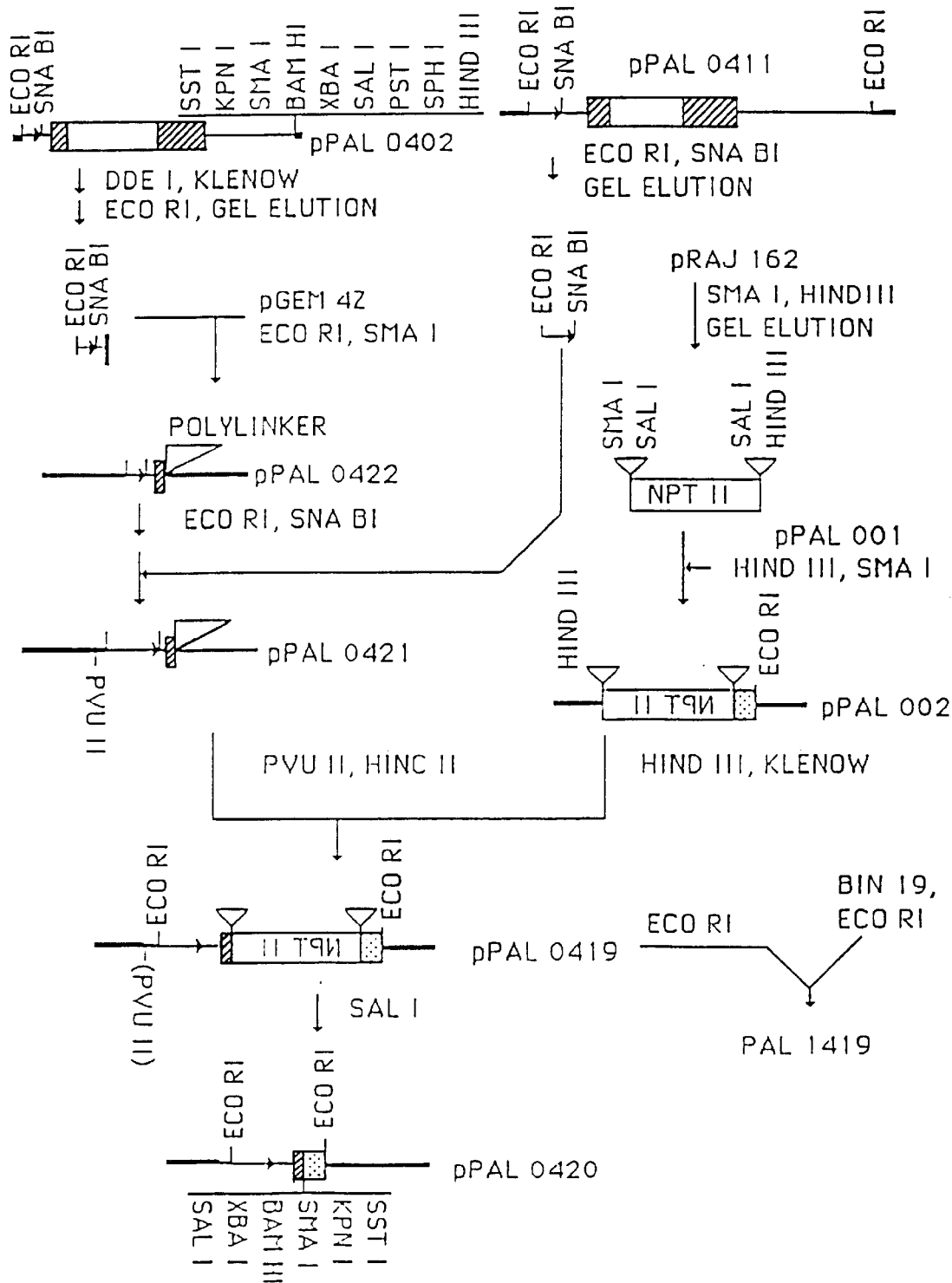

In order to provide promoter sequences that could be utilized with additional gene constructs, the plasmid pPAL 0419 was digested with Sal I. This digest removes the NPT II coding region and this Sal I digested pPAL 0149 was relegated giving rise to pPAL 0420. pPAL 0420 represents the pollen specific promoter followed by a polylinker for insertion of genes that has the following unique sites: Hinc II, Pst I, Sal I, Bam HI, Sma I, Kpn I, Sst I, followed by the nos ter polyadenylation signal. The entire promoter/ polylinker/nos ter construct can be conveniently excised as a single Eco RI fragment. The details of this construct is shown in FIG. 7c.

Figure 7D:
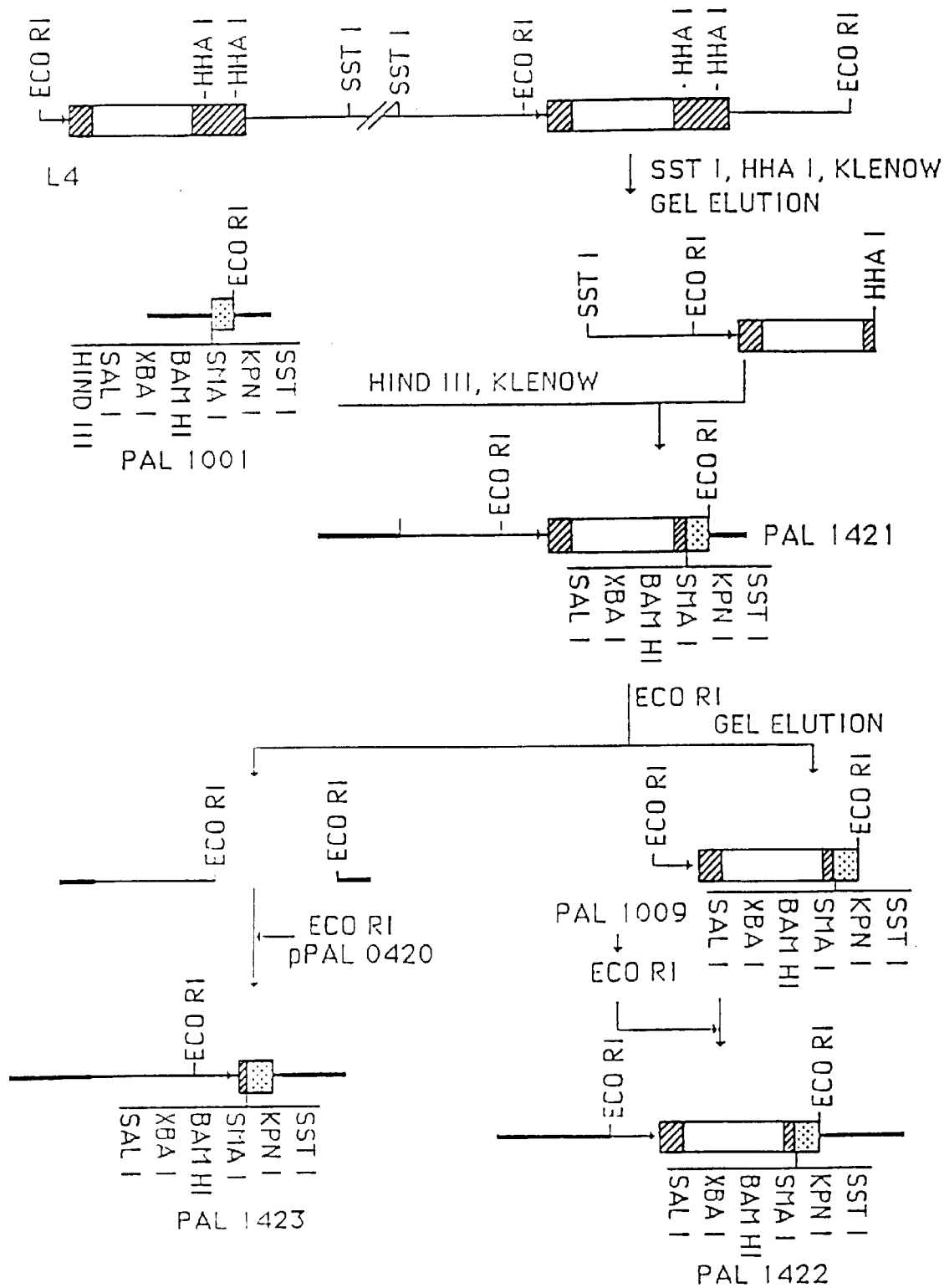

For additional pollen specific promoter constructs, the following approach was used. The intact L4 clone in the lambda cloning vector was digested to completion with the restriction enzymes Sst I and Hha I. The resultant fragments were separated by gel electrophoresis and a 2.65 Kb fragment that contains the promoter/first exon/intron/partial second exon region of gene three in clone L4 and corresponds to nucleotides 4565 to 7216 in the sequence of clone L4 was isolated. This fragment was made blunt ended with Klenow and cloned into the binary transformation vector PAL 1001 previously described. PAL 1001 was first cut with Hind III and made blunt ended with Klenow. Clones containing this fragment (promoter/first exon/intron/partial second exon) were recovered. A clone was chosen that contained this fragment in the proper orientation such that the direction of transcription was towards the nos ter in PAL 1001. This vector was named PAL 1421. This vector contains approximately 1.9 kb of upstream promoter region from the gene 3 in clone L4 followed by the first exon, the complete intron and 15 bases of the second exon of gene three followed by a polylinker containing the following unique sites: Sal I, Xba I, Bam HI, Sma I, Kpn I, SstI, and finally the nos ter polyadenylation signal. A variant of this vector was constructed by digesting PAL 1421 with Eco RI and isolating the fragment from this clone that contains the promoter polylinker nos ter sequences but contained less of the upstream region of the promoter. This fragment was re-cloned into PAL 1009. PAL 1009 is a BIN 19 derived vector from which most of the polylinker has been removed. This vector was constructed by digesting BIN 19 with Hind III and Sst I, making these sites blunt ended with Klenow and relegating such that a vector was recovered that contained a single unique Eco RI site for the insertion of fragments. PAL 1009 was digested with Eco RI and the Eco RI fragment from PAL 1421 that contains a shorter promoter/exon/intron/second exon/polylinker/nos ter structure was added to it. This gave rise to the vector PAL 1422, a vector that is essentially the same as PAL 1421 with the exception that there is less 5' promoter region. It should be noted that both PAL 1421 and PAL 1422 contain the intron from the third gene. For constructs which the presence of the intron may not be desired, intron sequences were removed from PAL 1421 by first digesting PAL 1421 with Eco RI and replacing the promoter/exon/intron/second exon/polylinker/ noster structure with the promoter/polylinker/nos ter structure from pPAL 0420 using Eco R1 such that a longer 5' promoter region is reconstructed in the binary transformation vector. The resultant vector was named PAL 1423. The outline of this construction is shown in FIG. 7d.

Figure 7E:
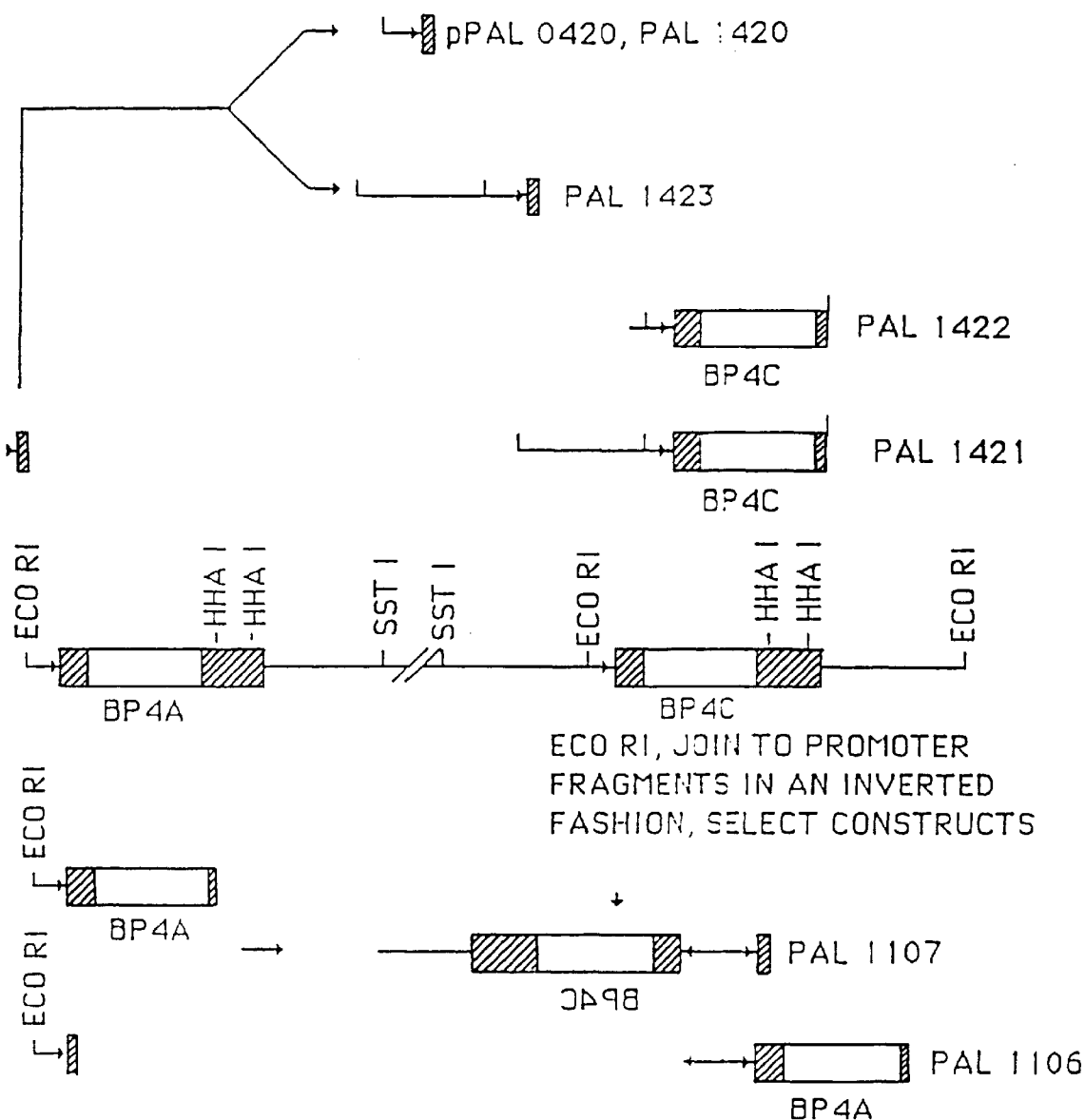

In FIG. 7e, a schematic diagram of the relationship of the above described vectors is presented. It should be noted that the vectors outlined in this Figure fall into three categories: 1, vectors which contain 5' upstream promoter regions that are substantially derived from the upstream region of the gene Bp4C (pPAL 0420, PAL 1420, PAL 1423), 2, promoter constructs that contain 5' upstream promoter regions and intron sequences from the gene Bp4C (PAL 1422, PAL 1421) and, 3, promoters which contain a chimeric 5' upstream region in which a portion of the 5' DNA sequence is inverted relative to the arrangement which appears in the genomic clone and uses the promoter fragment of Bp4A as a core promoter structure (PAL 1107 , PAL 1106). It should be noted that the functioning of each of these constructs can vary from plant species to plant species and it may be desirable to test a number of these promoter constructs when carrying out certain aspects of this invention.

Figure 8:
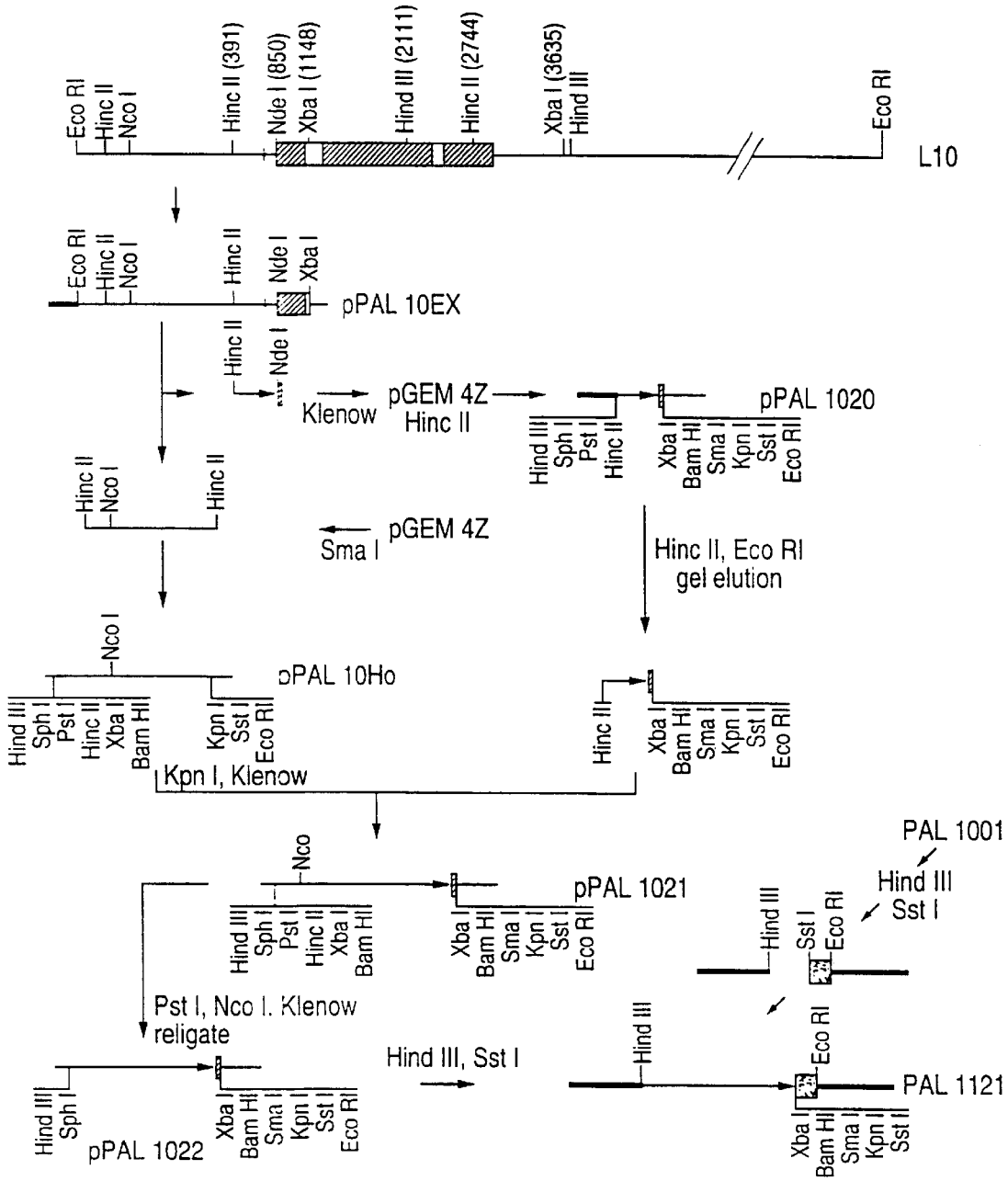
FIG. 8 is a schematic representation describing the production of vectors containing the promoter regions of clone L10, the details of which are discussed below.

The construction of pollen specific vectors that utilize the promoter regions of clones L10 and L19 was conducted as follows. The construction of the pollen specific vectors depicted in FIG. 8 utilizes promoter regions from clone L10. The start of transcription of clone L10 is located at nucleotide 1. The ATG start codon is located at nucleotides 45–47. The promoter region of this clone was excised by first subcloning the Eco RI-Xba I fragment of the clone that encompasses the entire promoter region and a portion of the first exon (the Xba I site is nucleotide 358 in the DNA sequence). This subclone (pPAL 10EX) was then digested with Hinc II and Nde I. The Nde I site is located immediately upstream of the ATG start codon at nucleotide 60 and the Hinc II site is located at nucleotide number −399. The digestion with these two enzymes releases a DNA fragment of 459 nucleotides which contains 62 nucleotides of untranslated transcribed leader sequence, and 397 nucleotides of 5' promoter region. The Nde I site in this fragment was made blunt ended by the use of Klenow, and this fragment was subcloned into the Hinc II site of the polylinker of pGEM 4Z. Clones were recovered in both orientations and the clone that contained the fragment in the orientation: Hind III, Sph I, Pst I. Hinc II, promoter-62 base pair leader fragment (Nde I blunt/Hinc II, does not cut with either Hinc II or Nde I) Xba I, Bam HI, Sma I, Kpn I, Sst I, Eco RI was chosen and named pPAL 1020. To add additional upstream regions, the Hinc II-HincII fragment that is approximately 1 Kb in length and is immediately upstream of the Hinc II site at position 391 in the DNA sequence was isolated from pPAL 10EX by digestion with Hinc II and gel elution of this fragment. This Hinc II fragment was cloned into the Sma I site of pGEM 4Z. Clones which contained the fragment in both orientations were recovered and a clone that contained the fragment in the following orientation was chosen: Hind III, Sph I, Pst I, Hinc II, Sal I, Xba I, Bam HI, the Hinc II fragment in the same orientation as in the genomic clone, that being right to left, 5'-3' (as a Hinc II/Sma I insertion which does not cut with either enzyme), Kpn I, Sst I, Eco RI. This subclone (pPAL10Hc) was digested with Knp I, made blunt end by the use of Klenow, then digested with Eco RI. To this cut subclone was added the promoter/untranslated leader sequence of pPAL 1020 by digesting pPAL 1020 with Hinc II and Eco RI, and adding this promoter fragment to the cut pPAL 10Hc. The resultant subclone contained a reconstructed promoter region of clone L10 differing from the intact region by only the filled in Kpn I site used for the joining of the two promoter fragments. This construct was named pPAL 1021. This vector contains in the following order: Hind III, Pst I, Sph I, Hinc II, Sal I, Xba I, Bam HI, the approximately 1 Kb Hinc II fragment joined to the Hinc II-Nde I promoter fragment followed by Xba I, Bam HI, Sma I, Kpn I, Sst I, and Eco RI. This subclone allows for the convenient removal of the promoter region of clone L10 such that the promoter can be easily used in cassette transformation vectors. The outline of this construction is shown in FIG. 8. The promoter region of pPAL 1021 was used for the construction of a pollen specific cassette transformation vector by carrying out the following constructs: The plasmid pPAL 1021 was digested with Nco I and Pst I. The plasmid was treated with Klenow and religated. This procedure effectively removed the portion of the polylinker that was 5' to the promoter in pPAL 1021. This plasmid was then digested with Hind III and Sst I, and cloned into the Hind III and Sst I sites of PAL 1001, giving rise to PAL 1121 . PAL 1121 has in the following order: the pollen specific promoter of clone L10 (approximately 1.1–1.2 Kb), followed by a polylinker with the following unique sites: Xba I, Bam HI, Sma I, Kpn I, Sst I, follower by the nos ter. The construction of this is outlined in FIG. 8.

Figure 9:
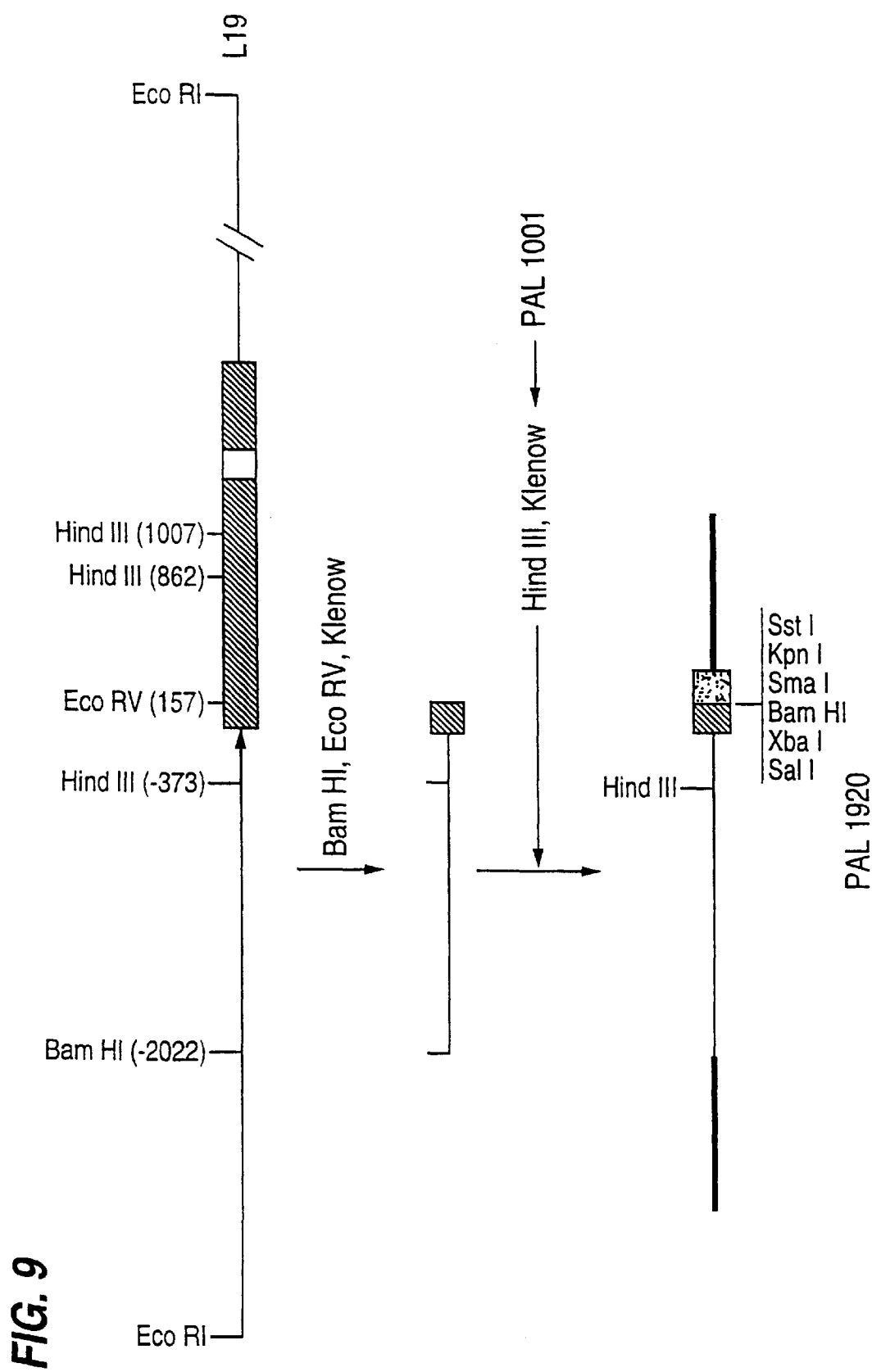
FIG. 9 is a schematic representation describing the production of vectors containing the promoter regions of clone L19, the details of which are discussed below.

The promoter region of the clone L19 was also used for construction of pollen specific vectors. The construction of these vectors is as shown in FIG. 9. Clone L19 has a single pollen specific gene contained with it. The start of transcription in this gene is located at position 1 in the DNA sequence. The ATG start codon is located at nucleotide position 136–138. The only intron is located at nucleotides 1202–1387, the stop translation codon is located at nucleotides 2024–2026. The end of transcription is located at approximately nucleotide 2074. The entire Eco RI fragment of this clone was subcloned into pGEM 4Z by using the Eco RI site located in the polylinker. The resultant clone was named pPAL 1901. The promoter region of this clone was excised as a single fragment by digesting pPAL 1901 with Bam HI and Eco RV, and a 2177 basepair fragment corresponding to the promoter region was isolated. This fragment covers from nucleotide −2200 (Bam HI) to nucleotide 156 (Eco RV). This promoter fragment contains over 2 Kb of 5' upstream region of the promoter in clone L19, 134 basepairs of 5' untranslated leader sequence and 20 basepairs of translated sequence. The Bam HI site in this fragment was made blunt ended by the use of Klenow and cloned into PAL 1001. This step was accomplished by cutting PAL 1001 with Hind III, making this site blunt ended by the use of Klenow and inserting the blunt ended Bam HI-Eco RV fragment in such an orientation that the promoter was oriented 5' to 3' with respect to the polylinker/nos ter polyadenylation signal. This vector was named PAL 1920 and contained within it in the following order: The promoter from clone L19 containing 134 base pairs of 5' untranslated leader sequence, 20 base pairs of translated sequence fused to a polyliker containing a former Hind III site inactivated by blunt ending, Sph I, Pst I, Sal I, Hinc II, Xba I, Bam HI, Sma I, Kpn I, Sst I (the unique cloning sites are underlined), the nos ter polyadenylation signal. This vector is convenient for the insertion of DNA sequences to be transcribed in pollen cells. The outline of this construct is shown in FIG. 9.

Figure 10:
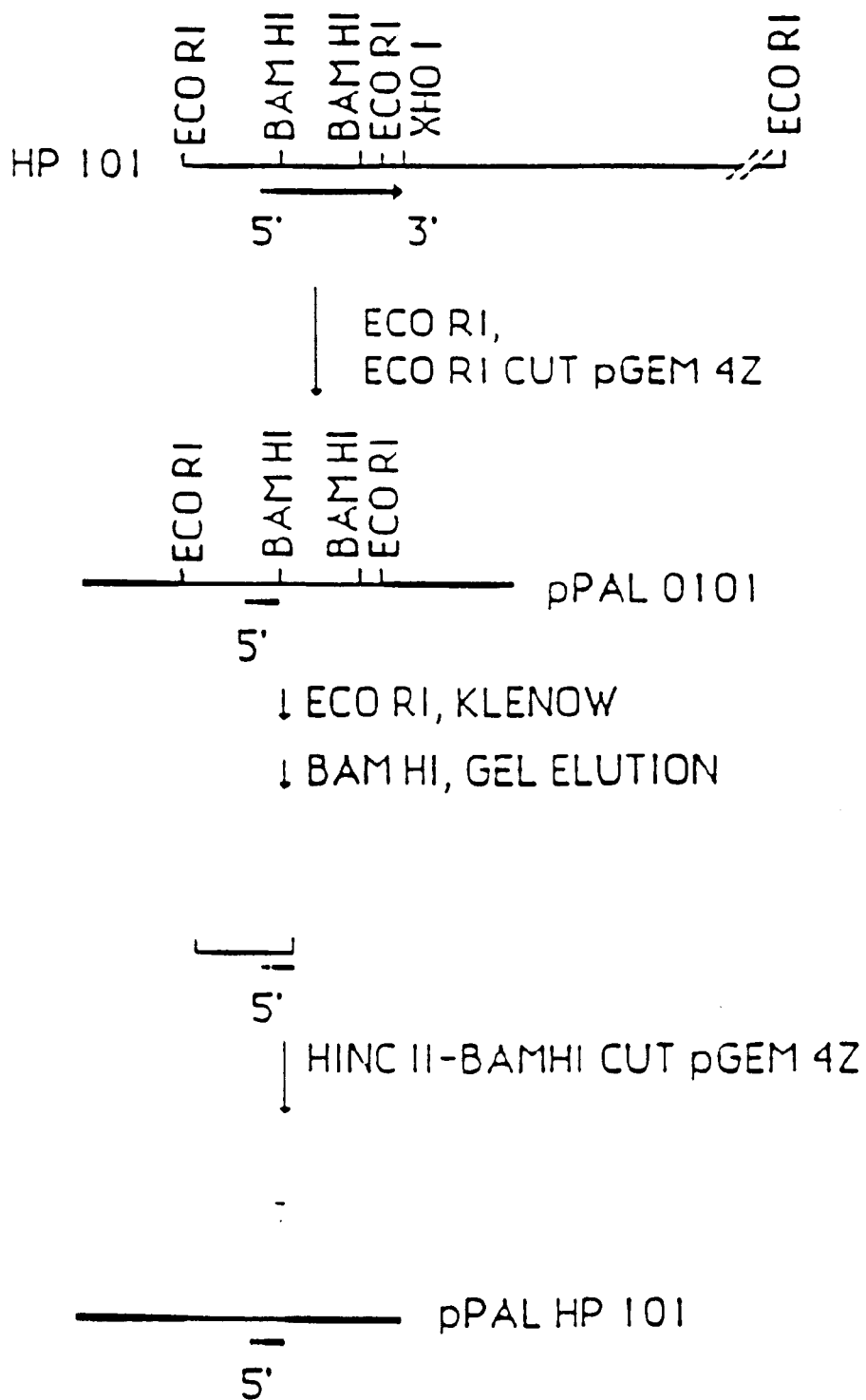
FIG. 10 is a schematic representation of a restriction map of a *Brassica napus* genomic clone that contains a gene (referred to as HP101) that is constitutively expressed at high levels in all cells including developing pollen cells. The portion of the clone that was used to provide promoter regions for the production of anti-sense RNA is shown, this construct gives rise to an anti-sense RNA that contains a region of transcribed RNA from this gene.

In FIG. 10, the restriction map of a *Brassica napus* genomic clone (HP 101) that contains a constitutively expressed gene is shown and the fragment of this clone that contains a 5' promoter region along with a portion of transcribed sequence is identified. This fragment was isolated by first cloning the small 2.5 kb Eco RI fragment in pGEM 4Z, and obtaining a subclone that had this fragment inserted in the indicated orientation relative to the polylinker of pGEM 4Z. This clone was called pPAL 0101 and was deposited Jan. 26, 1990 with the American Type Culture Collection (ATCC), 12301 Parklawn Drive, Rockville, Md., 20852, USA as pPAL0101/*E. coli* strain DH5 alpha under acession number ATCC 68210. This *E. coli* strain grows on standard *E. coli* media (LB) with 100 micrograms per ml of ampicillin. This subclone, pPAL 0101, was then digested with Eco RI, treated with Klenow fragment, then digested with Bam HI, which releases the promoter/transcribed region indicated. This fragment was cloned into Hinc II-Bam HI cut pGEM 4Z, resulting in the subclone pPAL HP101. The subclone can be used for the isolation of promoter sequences in vector constructs that utilize a constitutive promoter to synthesize pollen specific anti-sense RNA.

Figure 11:
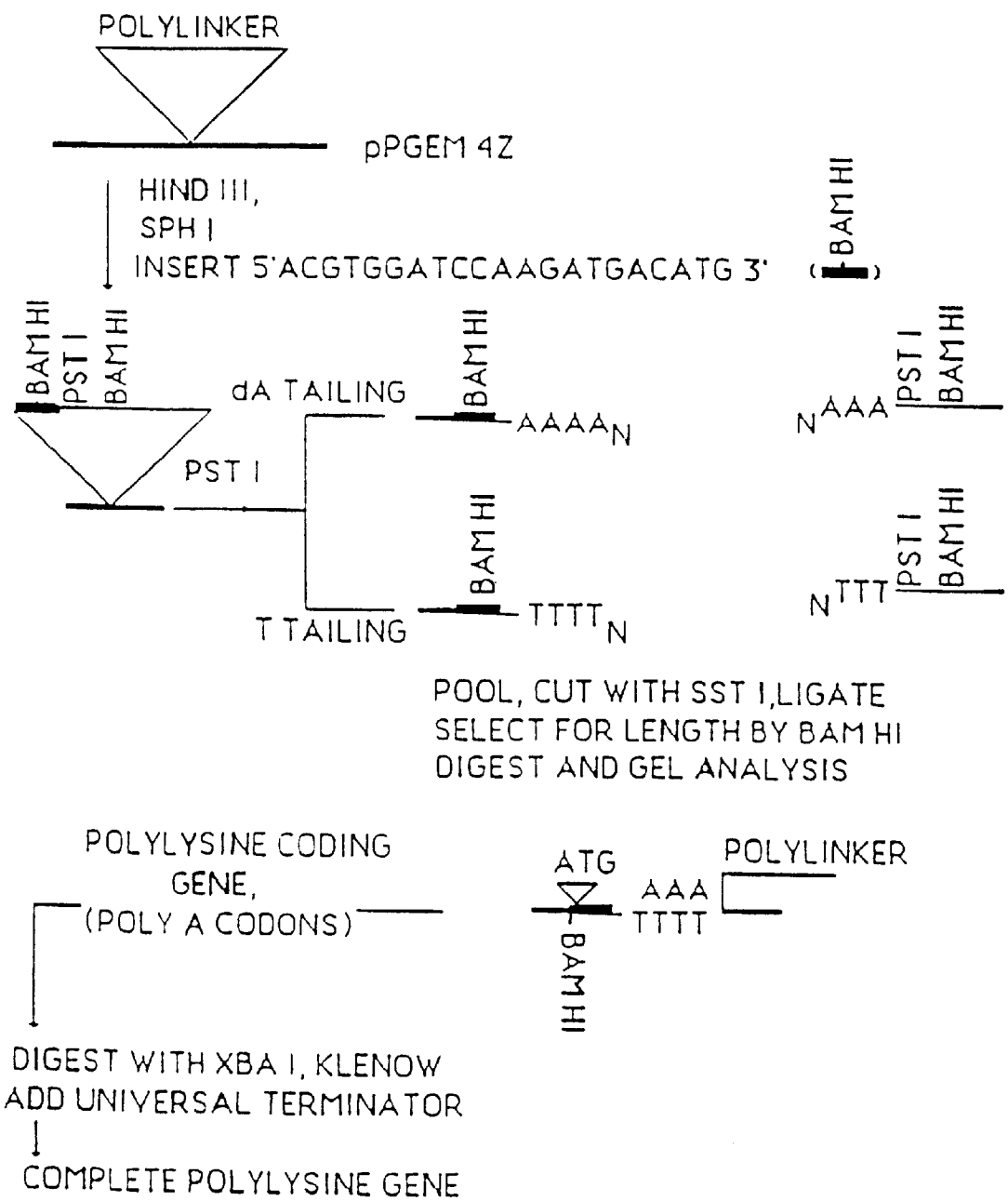
FIG. 11 is a schematic representation describing the production of a gene coding for a polylysine protein.

In FIG. 11 a schematic representation of producing a polylysine coding gene is shown. In this construct, the cloning vector pGEM 4Z was used as a recipient of a synthetic oligonucleotide containing a ATG start codon and to this was added a polynucleotide consisting of solely one nucleotide. This gene therefore, depending on the nucleotide used is a gene that has predominantly one codon, and codes for a protein that is composed of a polyamino acid. The construct was carried out in the following fashion: To provide a ATG start codon in a favourable initiation context, a synthetic oligonucleotide was constructed and inserted into pGEM 4Z between the Hind III and Sph I sites. This nucleotide had the sequence: 5'-ACGTGGATCCAAGATGACATG-3'. The resultant subclone therefore had the DNA sequence (restriction site for a introduced Bam HI site is underlined, the ATG start codon in bold) AACGT GGATCC AAG ATG ACA TGC GCA ACA TGG at the 5' region such that there was a ATG start codon in a favourable initiation context and a Bam HI site upstream of this site for excision of the coding sequence. This subclone was digested with Pst I, divided into two aliquots, one was tailed with T residues using terminal transferase and TTP, one was tailed with A residues using terminal transferase and dATP. The two tailed plasmids were mixed together, extracted with phenol-chloroform, ethanol precipitated and resuspended. The plasmid mixture was cut with Sst I, and relegated. Clones that were recovered were either clones that contained on the coding strand polyA or poly T. Clones were cut with Bam HI, the size of the insert determined by gel electrophoresis, and sequenced to determine if the clone coded for poly-lysine (polyA) or polyphenylalanine (poly T, poly U in the mRNA). A clone that coded for poly-lysine and was approximately 300 nucleotides was chosen and called pPAL pLys. This clone was cut with Xba I, blunt ended with Klenow and a universal translation terminator (available from Pharmacia PL Biochemicals, Montreal, Canada) was added to it, completing the construction of the gene. This construction is shown in FIG. 10.

Figure 12:
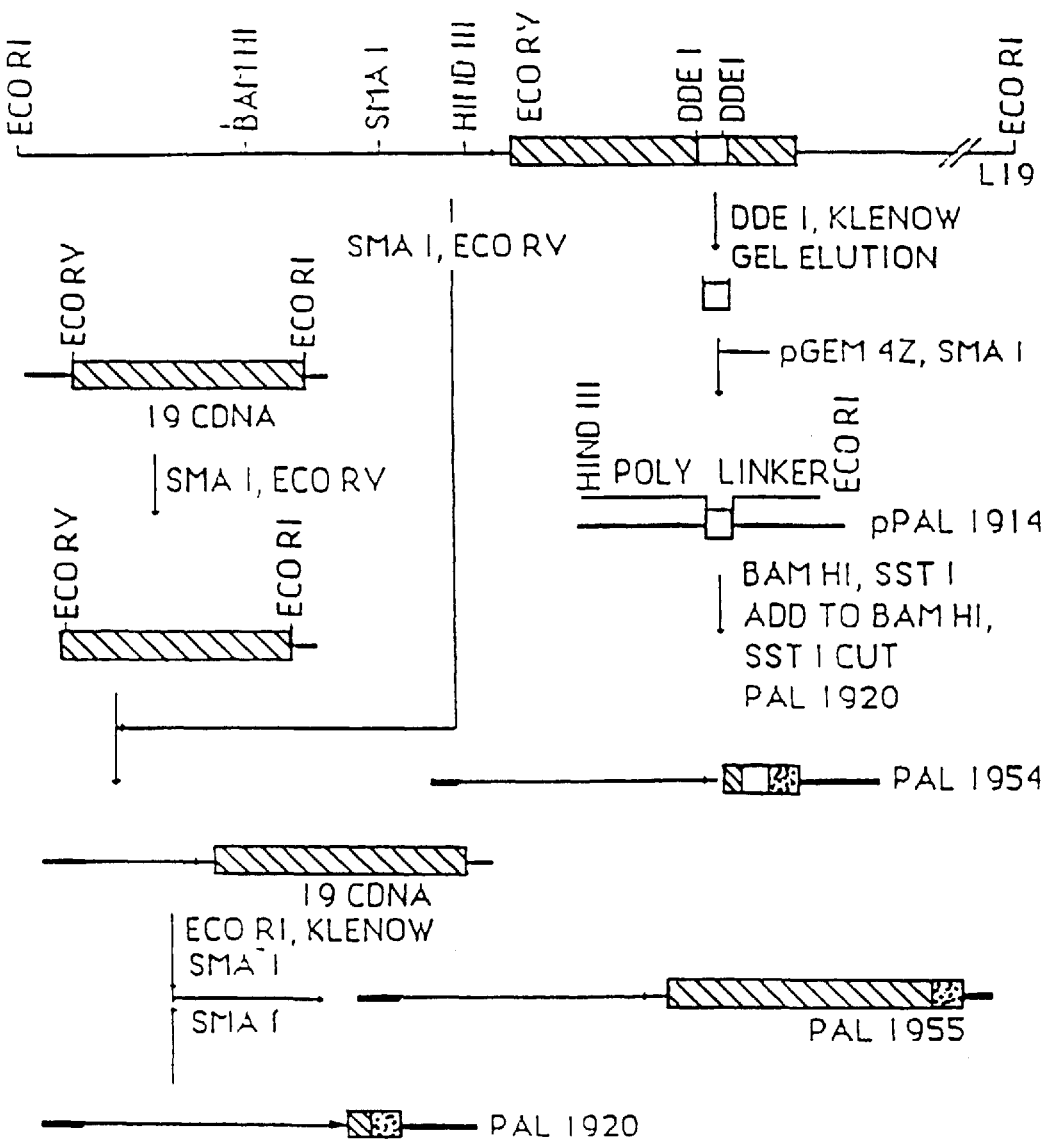
FIG. 12 is a schematic representation describing the production of an anti-sense gene specific to the intron region of clone L19 and a restorer that lacks the intron region targetted for anti-sense RNA inhibition.

In FIG. 12 a scheme for the production of an anti-sense gene specific to the intron region of clone L19 and the production of an intronless version of the number L19 gene is shown. For the first step in this, a restriction fragment from clone L19 was isolated that is substantially all intron. This fragment was isolated by using the restriction enzyme Dde I which cuts at a number of sites in the genomic clone, but the sites at nucleotides 1186 and 1348 give rise to a restriction fragment that is substantially intron sequences, having only approximately 16 nucleotides at the 5' side of the intron that are included in the final transcript, and 10 nucleotides at the 3' side of the intron that are included in the final transcript. This Dde I fragment was isolated by gel electrophoresis, made blunt ended and cloned into Sma I cut pGEM 4Z. Clones in both orientations were obtained, and the clone that contained the intron region in the orientation: Hind III, Sph I, Pst I, Sal I, Xba I, Bam HI (former Sma I) 3' end of the intron, intron sequences, 5' end of the intron, (former Sma I), Kpn I, Sst I, Eco RI was chosen. This clone was named pPAL 1914 and was digested with Bam HI and Sst I, and inserted into PAL 1920 previously cut with Bam HI and Sst I, creating the vector PAL 1954.

To create a specific restorer vector, the cDNA clone 19 cDNA (FIG. 6) was fused to the promoter region as follows: The cDNA clone was digested with Eco RV and Sma I as shown in FIG. 11. To this cut vector was added the Eco RV-Sma I fragment from clone L19. Clones were recovered that contained the reconstructed 5' region of the promoter and coding sequence, but carried coding sequences that lacked the intron, most of the coding regions being derived from the cDNA clone. This clone was digested with Eco RI, made blunt ended with Klenow, then digested with Sma I. A DNA fragment that represents the entire coding region and a portion of the promoter region was isolated and cloned into PAL 1920 cut with Sma I, leading to a reconstruction of the promoter region and coding region lacking an intron. This vector was called PAL 1955.

Figure 13:
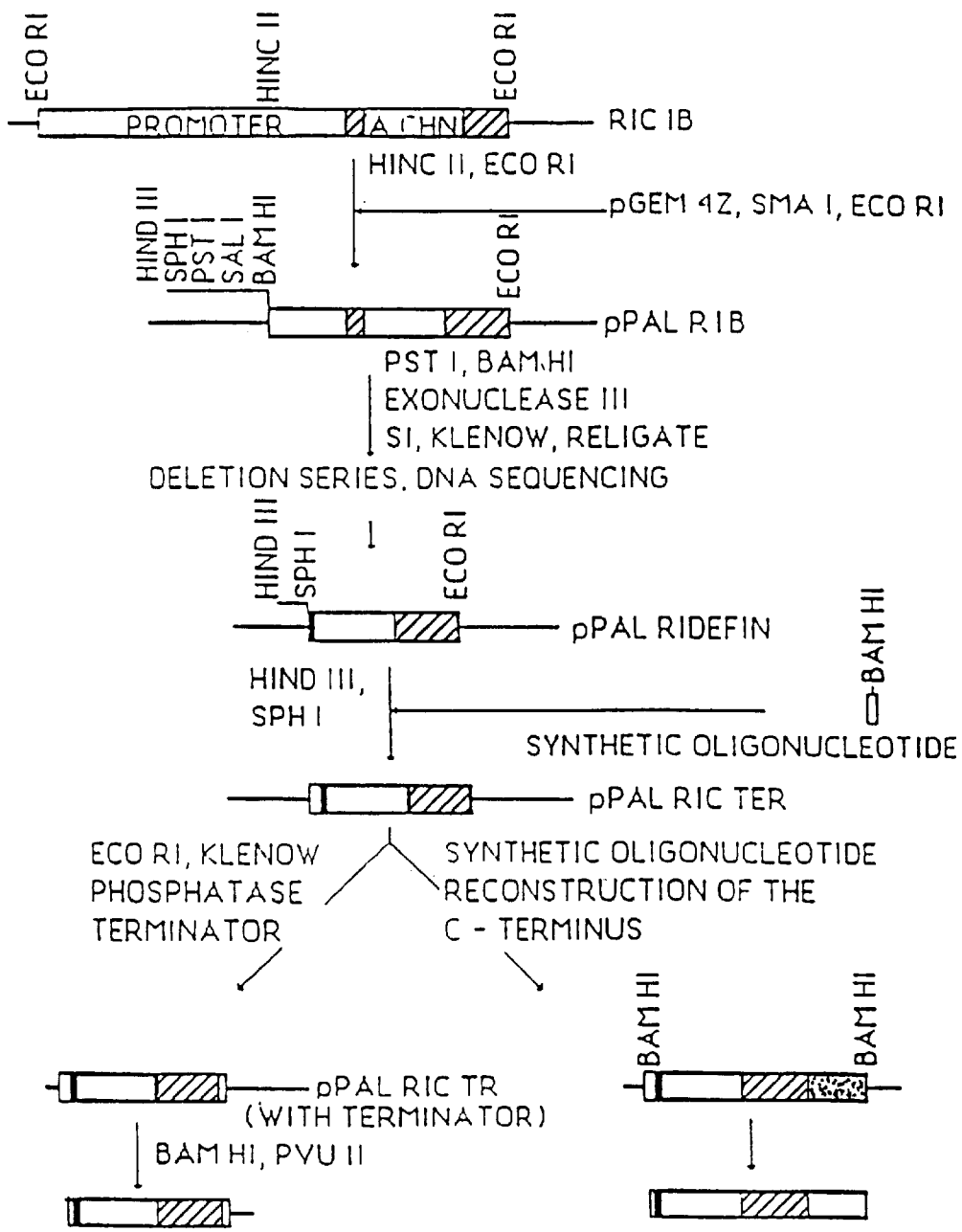
FIG. 13 is a schematic representation describing the production of clones containing versions of a ricin A chain coding region.

In FIG. 13, the production of clones containing the coding sequences of a protein functionally related to the ricin A chain protein isolated from Ricinus communis is detailed. This was accomplished by first isolating a genomic clone homologous to ricin from a genomic library of Ricinus zanzabarenis DNA constructed in the vector lambda gt10 using standard protocols. The library was screened with a DNA probe that corresponds to the N-terminal leader sequence of the ricin gene. The probe sequence was obtained from the published sequence of a Ricinus communis ricin gene (Halling, et al., Nucl. Acids Res 13:8019–8033, 1985). A genomic clone was isolated that contained the leader sequence and a portion of the A chain was isolated and called RIC 1B. This clone contained the promoter region, the 5' untranslated region, the N-terminal leader sequence and coding region that extended to amino acid 191(lle) in the published sequence (Halling, et al., Nucl. Acids Res 13:8019–8033, 1985). The difference between the Published sequence and RIC 1B was that the published nucleotide sequence at the region of lle 191 was: (lle 191 underlined) ACG AGA ATT CGG which codes for the amino acids: The Arg lle Ara while in RIC 1B the nucleotide sequence is ACG AGA ATT CGG, which codes for the same amino acids (The Arg lle Arg), the only difference being the last Arg is coded for by CGG in RIC 1B while in the published sequence it is coded for by AGG. This single nucleotide substitution has the effect of introducing a Eco RI site at lle 191. The clone RIC 1B therefore was missing the amino acids present after lle 191 since the clone was isolated as a single Eco RI fragment. This truncated version of ricin was used for construction of ricin A chain N-terminal deletions as follows: The clone RIC 1B was digested with Hinc II and Eco RI. The fragment was cloned into Eco RI-Sma I cut pGEM 4Z. The resulting clone, pPAL R1B was digested with Pst I and Bam HI. This cut clone was digested with Exo III nuclease, treated with S1 nuclease and Klenow fragment and then relegated. Subclones were obtained that had various portions of the 5' region deleted, and some of these deletions were sequenced. One deletion, named pPAL-Ridefin had the majority of the N-terminal leader DNA sequence removed and had Hind III and Sph I sites 5' to this region such that the DNA sequence was as follows: AAGCTT GCATGC GCA ACA TGG . . . wherein the first six nucleotides code for a Hind III site found in pGEM 4Z, the next six nucleotides codes for the Sph I site in pGEM 4Z and the following three triplets code for amino acids −20, −19, −18 . . . (Ala The Trp . . . ) in the published sequence (Halling, et al., Nucl. Acids Res 13:8019–8033, 1985). This subclone therefore had a deletion that removed the first 15 amino acids of the A chain leader sequences of ricin. To provide a ATG start codon in a favourable initiation context, a synthetic oligonucleotide was constructed and inserted into the subclone between the Hind III and Sph I sites. This nucleotide had the sequence: 5'-ACGTGGATCCAAGATGACATG-3'. The reconstructed clone (pPAL Rictr) therefore had the DNA sequence (restriction site for a introduced Bam HI site is underlined, the ATG start codon in bold) AACGT GGATCC AAG ATG ACA TGC GCA ACA TGG at the 5' region such that there was a ATG start codon in a favourable initiation context and a Bam HI site for excision of the coding sequence. The clone pPAL Rictr was digested with Eco RI, end filled with Klenow, and dephosphorylated with alkaline phosphatase. To the vector was added the universal translational terminator purchased from Pharmacia-PL biochemicals (Montreal, Canada) to provide a termination codon. The coding region from this clone was isolated by digestion with Bam HI and Pvu II, releasing the coding region and a small portion of pGEM 4Z, and this fragment can be cloned into the Bam HI and Sma I sites of transformation vectors. This DNA fragment codes for a version of a ricin A chain in which a C-terminal portion has been deleted. It should be noted that a number of C-terminal and N-terminal deletions of the ricin A chain have been tested in vitro for toxicity, and these reports have concluded that the N-terminal half of the ricin A chain is sufficient for cytotoxicity in vitro (for example see: Sudan et al., Nuc . Acids Res, 17:1717–1732, 1989). In order to obtain a complete coding region for the ricin A chain, synthetic version of the rest of the A chain was synthesized using the published sequence. This synthetic portion of the gene extended the DNA sequence to nucleotide 1182 in the published sequence and had a Eco RI sites at both ends that allowed for the joining of this fragment to the Eco RI site at the amino acids numbers 190–192. This reconstructed version of the gene also had a Bam HI site after the stop codon such that the DNA sequence of the gene at the 3' end was as follows: (nucl. 1181 is marked *) CCT CCA* TAA GGATCC GAATTC coding for amino acids: Pro Pro stop. followed by Bam H: and Eco RI, the Eco RI site being used for the insertion of the synthetic portion of the gene, the Bam HI being used for excision of the complete ricin A chain sequence since a synthetic Bam HI site is at the 5' end of the coding region also. The clone was called pPAL Riccom.

Figure 14:
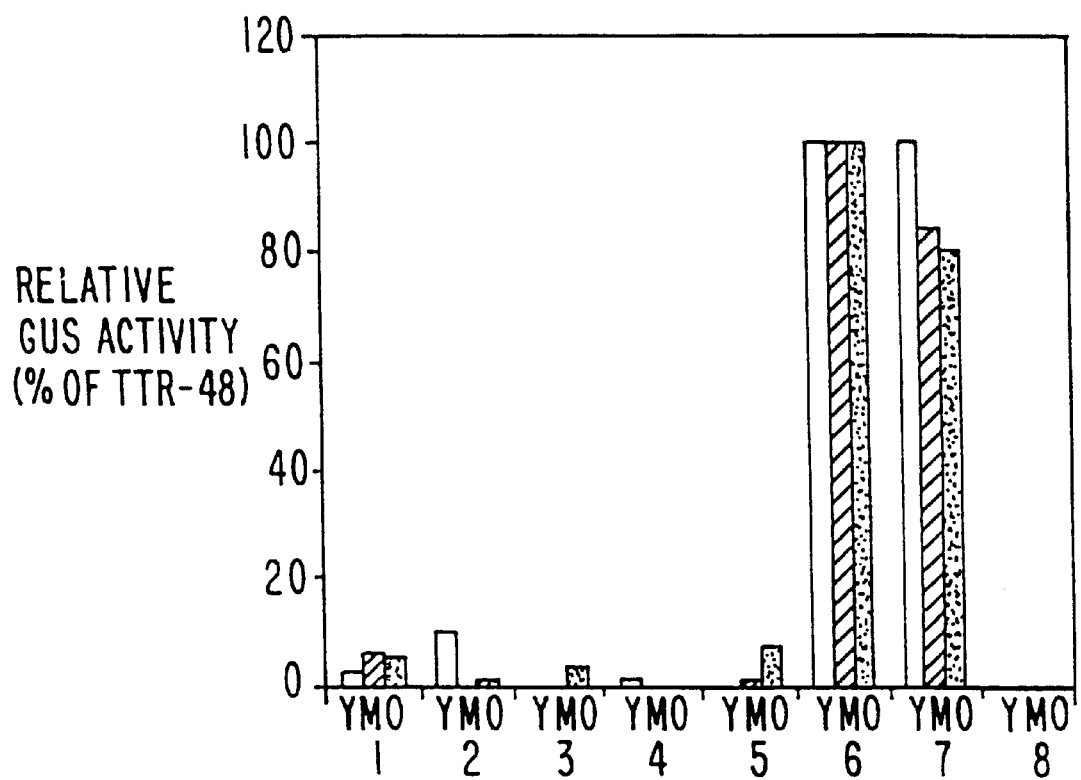
FIG. 14 is a histogram showing GUS activity in plants transformed with sense and anti-sense GUS genes.

In FIG. 14 the results of anti-sense RNA inhibition of Beta-glucuronidase gene activity is shown in a histogram of GUS gene activity found in transgenic plants that contained a sense GUS gene and were retransformed with a vector containing an anti-sense GUS gene. GUS activity levels were expressed as a percentage of the GUS activity found in the original GUS+ plant TTR-48. Tissue was obtained from young (Y), medium (M) and old (O) leaves and GUS activity was assayed spectrophotometrically. Lanes 1–5, samples from the retransformed plants TTR-1 to TTR-5 (TTR-48/PAL 1302); lane 6, samples from plant TTR-48; lane 7, samples from TTR-88(TTR-48/pVU 1011) and lane 8, samples from untransformed tobacco.

EXAMPLE 1

In this example, anti-sense RNA was used specifically for the inhibition of gene activity in plants. A tobacco plant expressing the Beta-glucuronidase gene under the control of the CaMV 35S promoter was produced by transformation of a non-transformed control tobacco cultivar, *N. tabaccum*, cv. Delgold. To accomplish this, tobacco leaves less than 8 inches in length were surface sterilized by exposure to ethanol for 5–6 seconds, then subsequent exposure to 1% sodium hypochlorite for a few minutes, usually 5–10 minutes, or until the cut edge of she petiole turned white, then rinsed several times in sterile distilled water. Leaf segments of approximately 0.5 to 1.0 square centimeters were cocultured for two days with *Agrobacterium tumefaciens* GV 3101 carrying the Ti plasmid pMP 90 to provide vir functions in trans (described by Koncz, C. and Schell J., 1986, Mol. Gen. Genet. 204:383–396) carrying the binary vector pBI 121.1 on shoot inducing media. This vector is a derivative of Bin 19 which contains the GUS gene driven by the CaMV 35S promoter and terminated by the nos ter and is available from Clonetech Laboratories, Palo Alto, Calif., USA. Transformed tobacco cells were selected on a shoot-inducing medium containing 0.8% agar, MS salts, B5 vitamins, 3% sucrose, 1 mg per L of benzyladenine, 0.1 mg per L of alpha naphthalene acetic acid, (NAA) 300 ug/ml kanamycin and 500 ug/ml carbenicillin (essentially as described by Horsch et al, 1985, Science, 227:1229–1231). Regenerated shoots were then transferred to a root-inducing medium consisting of B5 medium with 2% sucrose, 500 ug/ml carbenicillin and 0.5 mg/L each of NAA and indoleacetic acid IAA). Following selection on kanamycin, a tobacco transformant which displayed relatively high constitutive levels of GUS activity and contained a single unrearranged insertion of the 35S CaMV promoter-GUS-noster construct was selected. This plant (TTR-48, GUS+) was then re-transformed with a binary vector PAL 1302 which contains an anti-sense GUS gene, the construction of which is described in FIG. 1. In experiments involving the retransformation of the TTR-48 tobacco plant with PAL 1302, the shoot-inducing medium contained 20 ug/ml hygromycin and 300 ug/ml kanamycin to insure the selection of plants containing both the sense and anti-sense GUS constructs. Transformants were grown to maturity and self-pollinated in the greenhouse.

The leaves of tobacco plants resulting from the retransformation of TTR-48 (GUS+) with the anti-sense GUS vector PAL 1302 were assayed for GUS activity. The GUS activity in leaf extracts was assayed spectrophotometrically. Approximately 0.5 g of leaf tissue were ground with a Polytron in 2 ml of GUS extraction buffer (50 mM NaPO4 pH 7.0, 1 mM EDTA, 0.1% Triton X-100, 10 mM B-mercaptoethanol, 1 mM p-nitropheryl glucuronide, 100 ug/ml bovine serum albumin, 0.02% sodium azide) incubated at 30° C. for 6 h and the reaction stopped with the addition of 0.4 ml of 2.5M 2-amino-2-methyl-1, 3-propanediol. The amount of p-nitrophenol produced was calculated by measuring the absorbance at 415 nm. A stopped reaction containing an identical amount of leaf extract was used as a blank. Relative enzyme activities in the extracts were calculated and expressed as nanomoles of p-nitrophenol produced per mg of protein per minute. Ten plants were screened and they all displayed a large reduction in GUS activity levels relative to those observed in TTR-48. Five plants (TTR-1 to TTR-5) were chosen for a detailed analysis of the effects of anti-sense RNA inhibition of GUS gene activity. The retransformed tobacco plants TTR-1 to TTR-5 (FIG. 14, lanes 1–5) all showed a considerable to complete (lane 4) reduction in GUS activity regardless of the developmental stage of the leaves examined. Comparison of the highest level of GUS activity observed in the original GUS+ plant TTR-48 (FIG. 14, lane 6) with the highest level found in any of the plants retransformed with PAL 1302 (lanes 1–5) shows that the reduction in GUS activity was at least 90%. The levels of GUS activity found in the control plant TTR-88 (FIG. 14, lane 7) were similar to those of the original GUS+ plant (lane 6) indicating that the retransformation and regeneration process undergone by TTR-48 were not responsible for the decline in GUS activity observed in TTR-1 to TTR-5. Western blot analysis of total protein extracts obtained from young leaves were performed. For extraction of leaf proteins, approximately 100 mg of tissue were ground in a 1.5 ml Eppendorf tube containing 0.7 ml of GUS extraction buffer described above. An equal volume of SDS PAGE 2X sample loading buffer (1.3 M Tris-Cl pH 6.8, 2% B-mercaptoethanol, 50% glycerol, 5 mM EDTA, 0.1% bromophenol blue) was added and the samples incubated at room temperature for 15 min. The extract was centrifuged at 12,000 rpm for 2 min and the supernatant was frozen at −80° C. until use. Proteins were resolved in 10% SDS PAGE gels and immediately transferred electrophoretically onto a nitrocellulose filter. The GUS protein was then detected in the gels using the rabbit anti-B-glucuronidase antibody obtained from Clonetech Laboratories and an anti-rabbit lgG alkaline phosphatase conjugate kit (Promega Biotech, Madison Wis., USA) according to the manufacturers instructions. Equal amounts of protein were separated by sodium dodecyl sulfate polyacrylamide gel electrophoresis (SDS PAGE), transferred to nitrocellulose and cross-related with antibodies specific to the GUS protein. The amount of GUS protein detected on the Western blot correlated well with the GUS activity found in the leaves of all the tobacco plants examined whether these displayed high levels of activity such as TTR-48 or no discernible activity as in TTR-3 (FIG. 14, lane 3). The reduction in GUS activity in TTR-1 to TTR-5 can therefore be directly attributed to lower quantities of GUS enzyme within these plants. Southern blot analyses were performed to confirm that the sense GUS gene was still present and intact in TTR-1 to TTR-5 and to verify that the anti-sense GUS construct had correctly integrated in the DNA of these plants. It was found that the arrangement of the original sense GUS gene in TTR-48 was unaffected by the transformation with the anti-sense gene containing vector, and it was also further ascertained that amongst the plants selected for this, analysis, between 1–3 copies of the anti-sense gene were inserted into the genome of the plant which contained the sense gene. It was also determined that a single inserted anti-sense gene could lead to a near total reduction in sense gene activity. Northern blot analyses were conducted on total leaf RNA to determine if the reduction in the amounts of GUS enzyme observed in TTR-1 to TTR-5 correlated with their levels of GUS mRNA. Total RNA was prepared from tobacco leaves by grinding 0.5 g of tissue in 2 ml of extraction buffer (6 M guanidine-HCl, 0.1 M NaAc pH 6.0, 1.0% b-mercaptoethanol) for 10–30 sec using a Polytron. The mixture was then centrifuged at 5,000 rpm for 3 min, the supernatant layered on an equal volume of 5.7 M CsCl in 0.1 M NaCl, 10 mM Tris-Cl pH 7.5, 1 mM EDTA and centrifuged again at 35,000 rpm for 16 h at 15° C. The resulting RNA pellet was resuspended in 0.1 M NaAc pH 6.0, 0.1% SDS and extracted with an equal volume of phenol-chloroform (50:50, v/v). The aqueous phase was adjusted to 0.3 M NaAc and the RNA precipitated with 2 volumes of ethanol. Following centrifugation, the pellet was washed in 70% ethanol and resuspended in sterile distilled water. RNA samples were resolved in the presence of methylmercuric hydroxide in 1.3% agarose gels and transferred onto a nylon membrane. The membranes were probed with ($^{32}$P) UTP labelled sense or anti-sense GUS RNA transcripts. These transcripts were made from pGEM-GUS, a plasmid obtained by inserting the Bam HI-Sst I fragment of pBI 221.1 (which contains the entire GUS coding sequence) into the Bam HI-Sst I sites of pGEM-4Z. Probes were made by cutting pGEM-GUS with Eco RI and then using T7 RNA polymerase to provide a transcript which can hybridize to anti-sense GUS RNA or by digestion with Hind III and transcription with SP6 RNA polymerase giving an anti-sense transcript that can hybridize to sense GUS mRNA only. A radiolabelled sense-specific GUS RNA probe demonstrated that the levels of GUS mRNA found in TTR-1 to TTR-5 were considerably lower than those observed in TTR-48, the original GUS+ plant. As predicted, untransformed tobacco did not posses the GUS transcript. The levels of sense mRNA correlate well with the amount of GUS protein and activity observed in these plants. Northern blot analysis using an anti-sense-specific GUS RNA probe demonstrated the presence of anti-sense GUS transcript in the retransformed plants The reduced amounts of GUS protein and GUS activity observed in TTR-1 to TTR-5 can thus be attributed to the low levels of GUS mRNA found in these plants. Low levels of GUS mRNA were always associated with the presence of the anti-sense GUS RNA.

These results clearly indicate that a target sense gene can be successfully inhibited using anti-sense RNA.

EXAMPLE 1A

This example describes a method for isolating microspores in order to obtain genes that are essential to pollen formation and/or function. Microspores may be conveniently isolated by manual dissection of buds to remove anthers that are subsequently disrupted by gentle grinding in a mortar and pestle in 10% sucrose. The extract is then filtered through a 44 um nylon mesh and the microspores collected by centrifugation at 3000 x g for one minute. The pelleted microspores are re-suspended in 10% sucrose, filtered and pelleted as before. Other methods of isolating microspores can also be used.

Tissues other than microspores can be disrupted by a variety of methods and the disrupted tissue used for RNA isolation. It is convenient to disrupt the tissue by using a motor driven homogenizer with 10 mls of a solution of 6M guanidinium HCl, 0.1 M Na acetate, pH 6.0, 0.1 M beta-mercaptoethanol per gram of tissue. The homogenate is cleared by centrifugation at 5,000 x g and the supernatant is layered over a solution of 6M CsCl in Tris-EDTA buffer (TE buffer). Centrifugation at 100,000 x g for 12–20 hrs at 15° C. is used to pellet RNA which is subsequently re-suspended in water and re-precipitated in the presence of 0.3 M Na acetate and two volumes of ethanol. RNA is recovered by centrifugation and re-suspended in water. The RNA obtained by such method can be fractionated by oligo-dT cellulose chromatography to separate the polyadenylated mRNA from the bulk of the non-polyadenylated RNA. The microspore RNA is isolated by using a tight fitting motor driven glass homogenizer to disrupt the microspores. The homogenization of 300 ul of packed microspores is conducted in 1 ml 6M guanidinium-HCl, 0.1 M Na acetate, pH 6.0, 0.1 M beta-mercaptoethanol. The homogenate is centrifuged at 5000 x g and the cleared supernatant is layered over a solution of 6M CsCl in TE buffer. An overnight centrifugation at 100,00 x g is used to pellet the RNA which is subsequently re-suspended in water and re-precipitated in the presence of 0.3 M Na acetate and two volumes of ethanol. Other methods of RNA extraction can be used to obtain the RNA from the tissues described. Standard methodology using oligo-dT cellulose is used to obtain polyadenylated mRNA from these total RNA preparations.

EXAMPLE 2

This example relates to the use of constitutive promoters to regulate the expression of pollen specific anti-sense RNA. The CaMV 35S promoter from pBI 221 was isolated as a Hind III-Xba I fragment and cloned in PAL 1001 previously cut with Hind III and Xba I. This produced a vector that had the CaMV 35S promoter joined to the nos ter and in between the promoter and terminator were unique sites for: Xba I Bam HI, Sma I, Kpn I and Sst I. This vector was named PAL 1007. PAL 1007 was digested with Bam HI and to this digested vector was added a 2.4 Kb Bam HI fragment containing a coding region from clone L16 in the anti-sense orientation. This vector was called PAL 1305 and was used to transform *Brassica napus*. Transformation was carried out either using the method described in Moloney, M. M., et al. (Plans Cell Reports (1989) 8:238–242) or, transformation can be carried out with surface sterilized stem epidermal layers. For this procedure, seeds of *B. napus* L. ssp. oleifera cv. Westar were sown in 'Promix' mixed with 2 g/L of the slow-release fertilizer 'Nutricoate' in 8" pots. Plants were grown in the greenhouse under a 16 photoperiod (using natural and artificial lighting). For coculture and regeneration experiments stem-sections from the top three stem internodes of approximately 1.5 month old plants were used (i.e. those with elongated floral spikes and several open flowers). Intact stem-sections were surface sterilized for 30 seconds in 70% ethanol and 10 minutes in 1% sodium hypochlorite followed by three rinses in sterile distilled water. For transformation *Agrobacterium tumefaciens* GV 3101 carrying the Ti plasmid pMP 90 to provide vir functions in trans and the binary vector PAL 1110 was grown on YEP media (which consists of 10 gm per L of Yeast Extract, 10 gm per L of Bacto-pepetone and 5 gm per L of NaCl, pH 7.0 containing 100 ugs per mL kanamycin for selection of bacterial cells that contained the binary vectors). Cells were grown from one to two says at 28 C. The cells were collected by centrifugation and were resuspended at an approximate density of $10^6$–$10^7$ cells per mL in liquid EL which consists of MS micro- and macro- nutrients and B5 vitamins containing 40 mg/L of FeNa-EDTA (obtained from BDH chemicals) and 3% sucrose, 10 mg/L BenzylAdenine, and 0.5 mg/L alpha naphthalene acetic acid (NAA) and 18.8 mM $KNO^3$ plus 20.6 mM $NH_4NO^3$. Medium was solidified with 0.8% agar (Sigma) when the EL media was used for solid media plates.

The cell suspension was poured into the bottom of a sterile petri dish and sterilized stems were dissected directly in the bacterial suspensions. The segments were sectioned longitudinally into half segments and cut into approximately 5 mm sections. The dissected segments were placed on filter paper discs on solid EL media for a 3 day coculture under continuous fluorescent light (60 microeinsteins/m2/sec2) at 25 C. After a 2–3 day coculture, explants were transferred to solid EL media containing 500 ug/mL carbenicillin, and 100 ug/mL bekanamycin (Sigma). Shoots formed in 4–8 weeks, sections were transferred to fresh solid EL media with carbinicillin and bekanamycin every 3–4 weeks. Shoots that formed and did not bleach were excised and rooted on PDR media (B5-with 2% sucrose and 0.5 mg/L each of NAA and IAA). In some cases, green non-regenerating callus growing on selective medium was separated from explants and transferred to fresh medium to stimulate regeneration. Transformed plants were placed in a misting chamber, and after two to four weeks transferred to the greenhouse. Plants were grown under a 16 hour photoperiod and allowed to flower. Clonal propagation was used to increase plant lines as well as hand crossing and selection of seedlings from crossed plants on kanamycin containing media. This media consisted of 0.8% agar, one-tenth MS salts an 100 ugs per mL bekanamycin with no sucrose in the media. Surface sterilized seeds were used. The seeds were surface sterilized by rinsing in 70% ethanol for a few seconds, soaking in 1% sodium hypochlorite for 15 minutes, followed by rinsing three times in sterile distilled water. Seeds were place on the surface of the agar in sterile dishes and allowed to sprout. Plants which did not carry the kanamycin gene linked to the anti-sense gene bleached and died, while those that carried the antisense gene stayed green and were subsequently transferred to soil and allowed to flower.

EXAMPLE 3

In this example, another pollen specific coding region was used with the vector PAL 1007. In this case, a 1.3 Kb Hind III fragment from clone L19 was isolated, made blunt ended and cloned into the Sma I site of pGEM 4Z. This subclone was called pPAL 1914 and was then digested with Xba I and Sst I. This fragment was added to Xba I-Sst I cut PAL 1007, giving rise to a vector called PAL 1307. This vector contains the CaMV 35S promoter fused to a coding region from clone L19 in the anti-sense orientation. This vector was used to transform *Brassica napus* as detailed in example 34.

EXAMPLE 4

This example relates to the use of inducible promoters to regulate expression of pollen specific anti-sense RNA. In this example, the 1.2 Kb Hind III-Pst I fragment of the *D. melanogaster* 70 KD heat shock protein promoter was isolated from the subclone pPW 229 (Holmgren, R. et al., 1979, Cell 18:1359–1370) and cloned into Hind III-Pst I cut pGEM 4Z. The heat shock promoter was excised as a Hind III-Sma I fragment and cloned into Hind III-Sma I cut PAL 1001. This produced a vector (PAL 1009) that contains a heat shock promoter followed by a portion of the polylinker and nos ter. The Sma I site was used to clone the 1.3 Kb Hind III fragment from clone L19 following making this fragment blunt ended. The clone containing this fragment in the anti-sense orientation relative to the heat shock promoter was called PAL 1403. This vector was used to transform *Brassica napus* as in example 34. Additionally, since a single Eco RI site exists at the end of the nos ter in this construct, a selection marker gene was added to this construct, the enzyme Beta-glucuronidase driven by the CaMV 35S promoter using this unique Eco RI site for the insertion of this gene. This vector, which is the same as PAL 1403 except that it now contains a convenient gene for scoring transformation was named PAL 1408 and was used for transformation of *Brassica napus* as described in example 34.

EXAMPLE 5

This example relates to the use of a pollen specific promoter to specifically express pollen specific anti-sense RNA in pollen cells. For this, the vector PAL 1107 was used for the production of anti-sense RNA from the cDNA clone 4F described in FIG. 4. To construct this anti-sense vector, the Eco RI fragment from the cDNA clone 4F was isolated, made blunt ended with Klenow and cloned into the Sma I site of PAL 1107. A vector that contained the cDNA clone in the anti-sense orientation (as determined by restriction enzyme analysis) was chosen. This vector was named PAL 11074F and used to transform *Brassica napus* as described in example 34.

EXAMPLE 6

For this example, the vector PAL 1107 was used for the production of anti-sense RNA from the 2.4 Kb Bam HI fragment of clone L16 described in example 2. To construct this anti-sense vector, the 2.4 Kb Bam HI fragment from clone L16 was isolated and cloned into the Bam HI site of PAL 1107. A vector that contained this fragment in the anti-sense orientation (as determine by restriction enzyme analysis) was chosen. This vector was named PAL 1107-16CRAS and used to transform *Brassica napus* as described in example 34.

EXAMPLE 7

For this example, the vector PAL 1107 was used for the production of anti-sense RNA from the 1.3 Kb Hind III fragment of clone L19 described in example 3. To construct this anti-sense vector, the 1.3 Kb Hind III fragment from clone L19 was isolated and made blunt ended and cloned into the Sma I site of PAL 1107. A vector that contained this fragment in the anti-sense orientation (as determine by restriction enzyme analysis) was chosen. This vector was named PAL 1107-19CRAS and used to transform *Brassica napus* as described in example 34.

EXAMPLE 8

For this, the vector PAL 1107 was used for the production of anti-sense RNA from the cDNA clone related to clone L10 described in FIG. 5. To construct this anti-sense vector, the Eco RI fragment from the cDNA clone was isolated, made blunt ended with Klenow and cloned into the Sma I site of PAL 1107. A vector that contained the cDNA clone in the ante-sense orientation (as determined by restriction enzyme analysis) was chosen. This vector was named PAL 110710G and used to transform *Brassica napus* as described in example 34.

EXAMPLE 9

For this, the vector PAL 1107 was used for the production of anti-sense RNA from the cDNA clone related to clone L19 described in FIG. 6. To construct this anti-sense vector, the Eco RI fragment from the cDNA clone was isolated, made blunt ended with Klenow and cloned into the Sma I site of PAL 1107. A vector that contained the cDNA clone in the anti-sense orientation (as determine by restriction enzyme analysis) was chosen. This vector was named PAL 110719 and used to transform *Brassica napus* as described in example 34.

EXAMPLE 10

In this example, the pollen specific promoter in the vector PAL 1421 was used for the production of anti-sense RNA using the cDNA clone homologous to the gene contained with L10. This was accomplished by excising the cDNA clone from the cloning vector with Eco RI and making this fragment blunt ended with Klenow. This blunt ended cDNA fragment was cloned into the Sma I site of PAL 1421. Clones were recovered that contained the cDNA insert in both orientations, and one was chosen that contained the insert in the anti-sense orientation relative to the promoter of PAL 1421, resulting in the formation of a binary transformation vector PAL 1492. PAL 1492 was used to transform *Brassica napus* as described in example 34.

EXAMPLE 11

In this example, the pollen specific promoter in the vector PAL 1121 was used for the production of anti-sense RNA using the cDNA clone homologous to the gene contained within L10. This was accomplished by excising the cDNA clone from the cloning vector with Eco RI and making this fragment blunt ended with Klenow. This blunt ended cDNA fragment was cloned into the Sma I site of PAL 1121. Clones were recovered that contained the cDNA insert in both orientations, and one was chosen that contained the insert in the anti-sense orientation relative to the promoter of PAL 1121, resulting in the formation of a binary transformation vector PAL 1110. PAL 1110 was used to transform *Brassica napus* as described in example 34.

EXAMPLE 12

In this example, the pollen specific promoter from clone 19 was used for the expression of pollen specific anti-sense RNA. The transformation vector PAL 1920 was digested with Sma I. To the Sma I site was added the DNA fragment corresponding to the cDNA clone homologous to clone L10 by digesting the vector containing this clone with Eco RI and making the fragment blunt ended. This blunt ended cDNA fragment was cloned into the Sma I site of PAL 1920. Clones were recovered that contained the cDNA insert in both orientations, and one was chosen that contained the insert in the anti-sense orientation relative to the promoter of pPAL 1920, resulting in the formation of a binary transformation vector PAL 1921. PAL 1921 was used to transform *Brassica napus* as described in example 34.

EXAMPLE 13

In this example, anti-sense RNA is made specifically to the intron region of clone L19 and a specific restorer gene is made which lacks the intron from clone L19. The construction of these two vectors is outlined in FIG. 12. PAL 1954 was used to transform *Brassica napus* as in example 34 to make a male sterile line. To create a specific restorer plant line, the vector PAL 1955 was used to transform *Brassica napus* as in example 34.

EXAMPLE 14

In this example, the highly active promoter fragment of clone HP 101 we used to synthesize anti-sense RNA to the intron region of clone 19. For this example, the subclone containing the intron region of clone 19 that is detailed in FIG. 12, pPAL 1914 was digested with Hind III and Bam HI. The promoter fragment from clone pPAL HP101 was added to this construct as a Hind III-Bam HI fragment giving rise to clones containing the promoter fragment in the anti-sense orientation relative to the intron. This clone contained the promoter in an orientation such that transcription of the promoter would cause the production of an RNA a portion of which would contain anti-sense RNA homologous to the intron region of clone L19. This clone was called pPAL 19HP. The clone pPAL 19HP was digested with Hind III and Sst I, and cloned into the vector PAL 1001 using the Hind III and Sst I sites of PAL 1001, creating PAL HP19. PAL HP19 was used to transform *Brassica napus* as in example 34. It should be noted that the vector PAL 1955 (see example 13 and FIG. 12) can be used for fertility restoration in plants that carry PAL HP19.

EXAMPLE 15

The pollen specific promoter contained in the subclone pPAL 0420 was used for the construction of an anti-sense RNA gene under the control of a pollen specific promoter as follows: A DNA fragment coding for a polyubiquitin of Arabadopsis was isolated from a plasmid which contains a polyubiquitin gene that has 5 copies of the ubiquitin monomeric protein was obtained from the University of Wisconsin, Madison, Wis., USA and is described in Burke et al., Molecular and General Genetics, in press. A Bam HI-Bgl II fragment was isolated that contains 3 of the 5 copies of the polyubiquitin gene and this fragment was inserted into pPAL 0420 by using the single Bam HI site of the polylinker of PAL 0420. This gave rise to a plasmid containing the pollen specific promoter from clone L4 followed by an DNA fragment containing ubiquitin coding sequences in the antisense orientation followed by the nos ter polyadenylation signal. This promoter/anti-sense gene construct was excised from pPAL 0420 by digestion with Eco RI. The Eco RI fragment that contains the promoter anti-sense gene was inserted into the Eco RI site of the polylinker of BIN 19, resulting in the formation of a binary transformation vector was named PAL 1479. PAL 1479 was used to transform *Brassica napus* as described in example 34.

EXAMPLE 16

The vector PAL 1479 was used so transform tobacco as described in example 34.

EXAMPLE 17

The pollen specific promoter contained in the subclone pPAL 0420 was used for the construction of a pollen specific anti-sense RNA gene as follows: A DNA fragment coding for pine actin was obtained from J. Kenny-Byrne, Petawawa Canada. Two clones were obtained, Pac 1-A and Pac 2, the clone Pac 1-A being described in: Canadian Journal of Forestry Research (1988) 18:1592–1602, and the second clone Pac 2 (the sequence being closely homologous to that in Pac 1-A and the nucleotide sequence of which having been submitted for publication). A Sph I fragment was isolated from Pac 2 that contains the complete coding sequence of pine actin. This fragment also contains a small amount of 5' and 3' non-coding region. This Sph I fragment was cloned into the unique Sph I site of pGEM 4Z. From this subclone, a Xba I fragment was isolated that contains only coding region and this Xba I fragment was cloned into the unique Eco RI site of pGEM 4Z. A clone was chosen that had the orientation such that the 5' end of the gene was next to the Bam HI site in the polylinker and 3' end of the gene was next to the Sal I site in the polylinker. This plasmid was called pPAL PAC. The actin coding region was isolated form pPAL PAC by digestion with Bam HI and Sal I. This Bam HI-Sal I fragment was cloned into pPAL 0420 using the Bam HI and Sal I sites contained within the polylinker of pPAL 0420. This gave rise to a plasmid containing the pollen specific promoter from clone L4 followed by an DNA fragment containing the actin coding sequence in the anti-sense orientation followed by the nos ter polyadenylation signal. This promoter/anti-sense gene construct was excised from pPAL 0420 by digestion with Eco RI. The Eco RI fragment that contains the promoter antisense gene was inserted into the Eco RI site of the polylinker of BIN 19, resulting in the formation of a binary transformation vector PAL 1498. PAL 1498 was used to transform *Brassica napus* as described in example 34.

EXAMPLE 18

The vector PAL 1498 was used to transform tobacco plants as outlined in example 34.

EXAMPLE 19

In this example, tobacco that has been previously transformed to hygromycin resistance was transformed with an anti-sense gene that specifically blocks the hygromycin resistance in the pollen cells by virtue of the fact that the anti-sense gene is under the control of a pollen specific promoter in the vector PAL 1106. Transformed tobacco that were resistant to hygromycin were obtained using the vector PAL 1302 which is described in example 1. Selection of tobacco plant cells resistant to hygromycin was via coculture with PAL 1302 and selection of 50 ug per ml hygromycin. Southern blot analysis demonstrated the presence of 5–6 copies of the sense hygromycin phosphotransferase gene in one plant. This plant, referred to as TTR-122, was retransformed with a vector called PAL 1107A. Pal 1107A is the vector PAL 1106 to which has been added the 0.8 Kb Bam HI hygromycin phosphotransferase fragment isolated from PAL 1302 and inserted into PAL 1106 in the anti-sense orientation relative to the pollen specific promoter in PAL 1106. The resulting vector was called PAL 1107A. Plants obtained from this transformation were resistant to both hygromycin and kanamycin in the leaf tissue and were shown by southern blot analysis to contain the anti-sense gene. These plants were allowed to grow in the greenhouse and self fertilize. Clonal propagation of these plants were used as a preliminary increase of single plants, and these clonally propagated plants were used for the production of male sterile plant line. For example, a plant which contained a single copy of the anti-sense gene and was derived from the transformation of TTR-122 was planted in a sand soil mixture and allowed to grow in the greenhouse. This plant is referred to as TTR-203. Measurement of the hygromycin phosphotransferase activity in this plant demonstrated high activity in leaves, petals, stigma and pistal and anther walls, but very low levels in pollen. TTR-122 showed high levels of hygromycin phosphotransferase activity in leaves, petals, stigma and pistal and anther walls and in pollen. This demonstrated that the anti-sense gene was effective in blocking the expression of the sense gene only in the pollen. Northern blot analysis confirmed the presence of the anti-sense transcript specifically in the pollen of TTR-203 and also demonstrated low levels of the sense gene mRNA. When flower buds first appeared, TTR-203 was watered three times weekly with a solution of hygromycin (250 ugs per mL), thoroughly saturating the sand soil mixture. This watering was continued for approximately four weeks, or the period of time in which the major flowering was occurring. Flowers produced during this time on plants containing the anti-sense gene were male sterile. Anther and pollen formation was inhibited, and mature pollen failed to develop. Female fertility was unaffected by this treatment as hand pollination could be used for the pollination of the female portion of the male sterile flowers. Pollen that was from a hygromycin resistant plant was used for the hybrid seed production. Watering of the plants with hygromycin was stopped, and normal watering was resumed. Flowers that formed on plants after the hygromycin watering was stopped were male fertile and set selfed seed.

EXAMPLE 20

The pollen specific vector PAL 1107 was used for the production of male sterile plants The plant TTR-122 described above, was retransformed with a vector called PAL 1107HYGAS. Transformation was conducted as described in example 34. Pal 1107HYGAS is the vector PAL 1107 to which has been added the 0.8 Kb Bam HI hygromycin phosphotransferase fragment isolated from PAL 1302 and inserted into PAL 1107 in the anti-sense orientation relative to the pollen specific promoter in PAL 1107. Plants obtained from this transformation were resistant to both hygromycin and kanamycin in the leaf tissue and were shown by southern blot analysis to contain the anti-sense gene. These plants were allowed to grow in the greenhouse and self fertilize. Clonal propagation of these plants were used as a preliminary increase of single plants, and these clonally propagated plants were used for the production of male sterile plant lines as in example 19.

EXAMPLE 21

For the production of male sterile plants, the vector PAL 1419 was used to transform Tobacco as outlined in example 34. The vector PAL 1419 contains the pollen specific promoter from clone L4 controlling the expression of the NPT II gene oriented in the anti-sense orientation relative to the pollen specific promoter. This vector also contains a constitutive version of the NPT II gene in the sense orientation driven by the nos promoter. This vector therefore can confer resistance to kanamycin in all plant cells except pollen cells wherein the expression of the sense gene is inhibited by the expression of the anti-sense gene which is specifically expressed in the pollen. Tobacco plants were obtained following transformation of the vector PAL 1419. These plants were rooted and allowed to set flower. Plants were watered with kanamycin while flowering.

EXAMPLE 22

The vector PAL 1419 was used to transform *Brassica napus* as outlined in example 34.

EXAMPLE 23

The vector PAL 1419 was used for the transformation of petunia leaf discs.

EXAMPLE 24

In this example, the complete ricin A chain (pPAL Riccom) described in FIG. 13 was inserted into the vector PAL 1420 as a Bam HI fragment. Vectors were recovered that contained the ricin gene in both the sense and anti-sense orientation. A vector that contained the ricin A chain in the sense orientation was recovered and called PAL 1420RIC. A vector that contained the gene in the anti-sense orientation was called PAL 1420RICAS. PAL 1420RIC and PAL 1420RICAS were used for transformation of *Brassica napus* as described in example 34 giving rise to plants that carried either the sense or anti-sense copy of the ricin A chain gene under the control of the pollen specific promoter in PAL 1420.

EXAMPLE 25

In this example, the truncated version of the ricin A chain (pPAL Rictr) described in FIG. 13 was inserted into the vector PAL 1420 as a Bam HI fragment. Vectors were recovered that contained the truncated ricin gene in both the sense and anti-sense orientation. A vector that contained the ricin A chain in the sense orientation was recovered and called PAL 1420tRIC. A vector that contained the gene in the anti-sense orientation was called PAL 1420tRICAS. PAL 1420tRIC and PAL 1420tRICAS were used for transformation of *Brassica napus* as in example 34 giving rise to plants that carried either the sense or anti-sense copy of the truncated ricin A chain gene under the control of the pollen specific promoter in PAL 1420.

EXAMPLE 26

PAL 1420RIC and PAL 1420RICAS were used for transformation of tobacco plants as in example 34, giving rise to plants that carried either the sense or anti-sense copy of the ricin A chain gene under the control of the pollen specific promoter in PAL 1420.

EXAMPLE 27

The vectors PAL 1420tRIC and PAL 1420tRICAS were used for transformation of tobacco plants as in example 34 giving rise to plants that carried either the sense or anti-sense copy of the truncated ricin A chain gene under the control of the pollen specific promoter in PAL 1420.

EXAMPLE 28

For this example, the vector PAL 1423 was used to express the polylysine gene contained in the subclone pPAL pLys. The coding region from pPAL pLys was isolated by Bam HI digestion and cloned in the sense orientation into Bam HI cut PAL 1423, giving rise to PAL 1487. PAL 1487 was used to transform tobacco as in example 34.

EXAMPLE 29

For this example, the vector PAL 1920 was used to express the polylysine gene contained in the subclone pPAL pLys. The coding region from pPAL pLys was isolated by Bam HI digestion and cloned in the sense orientation into Bam HI cut PAL 1920, giving rise to PAL 1987. PAL 1987 was used to transform tobacco as in example 34.

EXAMPLE 30

In this example, a pollen specific promoter was used to synthesize a protein molecule that is destructive to cellular function and development, namely the protease trypsin. The cDNA sequence coding for trypsin has been described by Stevenson et al., Nucl Acids Res, 1986, 14:8307–8330. The cDNA clone pMPt9 was obtained and used for the production of a modified trypsin molecule in which the N-terminal amino acid residues were removed to give a protein that consisted of solely the active protease form of trypsin and differed from the mature form in that there was a methionine residue at the N-terminal position of the mature protein, replacing the Isoleucine found at this position in the active mature protein. This was accomplished by digesting the plasmid pMPt9 with Fok I and Pst I, and recovering a fragment that encompasses nucleotides 81 to 835, the nucleotides after 835 being the G:C tail used for cloning of the cDNA, and treating this fragment with Klenow, and cloning into blunt ended Sma I cut M13mp19RF, and isolating a single stranded phage clone that was used for site specific metagenesis to change the isoleucine codon at nucleotides 84–86 in the published sequence from ATT to ATG, introducing a initiation codon where the isoleucine codon was. The mutated gene recovered was excised with Sal I and Sst I, and inserted into PAL 1421 and named PAL 1456. The vector PAL 1456 was used to transform tobacco as in example 34. It should be noted that a restorer gene can be made if a trypsin inhibitor is inserted in an analogous fashion using a clone L4 derived promoter and transformed into a male parent line. The expression of the trypsin inhibitor in the hybrid will specifically block the activity of the trypsin enzyme. A number of cDNA and genomic DNA sequences can be found for soybean and other trypsin inhibitors, for example see: Jofuku, K. D. and Goldberg, R. B., The Plant Cell 1989, 1:1079–1093.

EXAMPLE 31

In this example, we use a pollen specific promoter to synthesize the enzyme IamH specifically in pollen cells. The enzyme has activity that can cause the production of NAA from NAM, the substance NAA functioning as a plant hormone that is substantially toxic to developing pollen grains, while the precursor NAM being relatively non-toxic. For this example, the IamH gene was inserted into the vector PAL 1423. The IamH gene was isolated from pPCV311 as described in FIG. 19 and cloned as a Bam HI-Sst I fragment in the Bam HI-Sst I sites of PAL 1423, creating PAL 1424. This vector has the IamH gene (T-DNA gene 2) under the control of a pollen specific promoter from clone L4. PAL 1424 was used to transform Tobacco as outlined in example 34.

EXAMPLE 32

The vector PAL 1424 was used to transform *Brassica napus* as outlined in example 34.

EXAMPLE 33

In this example, the vector PAL 1107 was used for the production of tissue-specific GUS (beta-glucuronidase) enzyme. The gene for this enzyme is available from Clonetech Laboratories, Palo Alto, Calif., USA. The gene was inserted into PAL 1107 as a Bam HI-SstI fragment and was used to transform tobacco as in example 34. Plants produced had detectable GUS activity only in developing pollen cells, and not any other tissue tested. It should be noted that application of non-toxic analog of glucuronic acid to which has been conjugated a toxic molecule such as glyphosate could be applied to these plants and cleavage of the toxic moiety from the glucuronic acid would occur only in pollen cells. This provides an example of an enzyme that could be used for the production, in a tissue-specific fashion, of a toxic substance from a non-toxic analog.

EXAMPLE 34

This example describes methods used to transform tabacco and *Brassica napus*.

For tobacco transformation, the tobacco cultivar, *N. tabaccum*, cv. Delgold was used. To accomplish this transformation, tobacco leaves less than 8 inches in length were surface sterilized by exposure to ethanol for 5–6 seconds, then subsequent exposure to 1% sodium hypochlorite for a few minutes, usually 5–10 minutes, or until the cut edge of the petiole turned white, then were rinsed several times in sterile distilled water. Leaf segments of approximately 0.5 to 1.0 square centimeters were excised from the sterile leaves, and were cocultured on shoot inducing media for two days with *Agrobacterium tumefaciens* GV 3101 carrying the Ti plasmid pMP 90 to provide vir functions in trans (described by Koncz, C. and Schell, J., 1986, Mol. Gen. Genet. 204:383–396) carrying the binary vector of interest. The vector is usually a derivative of Bin 19 which contains the NPT II gene driven by the nopaline synthase promoter and terminated by the nos ter for selection of plant cells with kanamycin. Bin 19 is available from Clonetech Laboratories, Palo Alto, Calif., U.S.A. Transformed tobacco cells are selected on a shoot-inducing medium containing 0.8% agar, MS salts, B5 vitamins, 3% sucrose, 1 mg per L of benzyladenine, 0.1 mg per L of alpha naphthalene acetic acid, (NAA) 300 $\mu$g/ml kanamycin and 500 $\mu$g/ml carbenicillin (essentially as described by Horsch et al. 1985, Science, 227:1229–1231). Regenerated shoots are then transferred to a root-inducing medium consisting of B5 medium with 2% sucrose, 500 $\mu$g/ml carbenicillin and 0.5 mg/L each of NAA and indoleacetic acid (IAA). Rooted transformants are transferred to a misting chamber containing high humidity, after which the humidity is gradually lowered and plants are subsequently transferred to the greenhouse.

For transformation of *Brassica napus*, the binary vector containing Agrobacterium strain GV 3101 carrying pMP 90 to provide vir functions in trans is used. Transformation was carried out either using the method described in Moloney, M. M., et al. (Plant Cell Reports (1989) 8:238–242) or, transformation can be carried out with surface sterilized stem epidermal layers. For this procedure, seeds of *B. napus* L. ssp. oleifera cv. Westar were sown in 'Promix' mixed with 2 g/l of the slow-release fertilizer 'Nutricoate' in 8" pots. Plants were grown in the greenhouse under a 16 photoperiod (using natural and artificial lighting). For coculture and regeneration experiments stem-sections from the top three stem internodes of approximately 1.5 month old plants were used (i.e. those with elongated floral spikes and several open flowers). Intact stem-sections were surface sterilized for 30 seconds in 70% ethanol and 10 minutes in 1% sodium hypochlorite followed by three rinses in sterile distilled water. For transformation Agrobacterium tumefaciens GV 3101 carrying the Ti plasmid pMP 90 to provide vir functions in trans and the binary vector of choice was grown on YEP media (which consists of 10 gm per L of Yeast Extract, 10 gm per L of Bacto-pepetone and 5 gm per L of NaCl, pH 7.0 containing 100 ugs per mL kanamycin for selection of bacterial cells that contained the binary vectors). Cells were grown from one to two days at 28 C. The cells were collected by centrifugation and were resuspended at an approximate density of $10^6$–$10^7$ cells per mL in liquid EL which consists of MS micro- and macro-nutrients and B5 vitamins containing 40 mg/L of FeNa-EDTA (obtained from BDH chemicals) and 3% sucrose, 10 mg/L BenzylAdenine, and 0.5 mg/L alpha naphthalene acetic acid (NAA) and 18.8 mM $KNO^3$ plus 20.6 mM $NH_4NO^3$. Medium was solidified with 0.8% agar (Sigma) when the EL media was used for solid media plates.

The cell suspension was poured into the bottom of a sterile petri dish and sterilized stems were dissected directly in the bacterial suspensions. The segments were sectioned longitudinally into half segments and cut into approximately 5 mm sections. The dissected segments were placed on filter paper disc on solid EL media for a 3 day coculture under continuous fluorescent light (60 microeinsteins/m2/sec2) at 25 C. After a 2–3 day coculture, explants were transferred to solid EL media containing 500 ug/mL carbenicillin, and 100 ug/mL bekanamycin (Sigma). Shoots formed in 4–8 weeks, sections were transferred to fresh solid EL media with carbinicillin and bekanamycin every 3–4 weeks. Shoots that formed and did not bleach were excised and rooted on PDR media (B5- with 2% sucrose and 0.5 mg/L each of NAA and IAA). In some cases, green non-regenerating callus growing on selective medium was separated from explants and transferred to fresh medium to stimulate regeneration. Transformed plants were placed in misting chamber, and after two–four weeks transferred to the greenhouse. Plants were grown under a 16 hour photoperiod and allowed to flower.

Clonal propagation was used to increase plant lines as well as hand crossing and selection of seedlings from crossed plants on kanamycin containing media. This media consisted of 0.8% agar, one-tenth MS salts and 100 ugs per mL bekanamycin (available from Sigma Chemicals, St. Louis, Mo., U.S.A.) with no sucrose in the media. Surface sterilized seeds were used. The seeds were surface sterilized by rinsing in 70% ethanol for a few seconds, soaking in 1% sodium hypochlorate for 15 minutes, followed by rinsing three times in sterile distilled water. Seeds were placed on the surface of the agar in sterile dishes and allowed to sprout. Plants which did not carry the kanamycin gene linked to the antisense gene bleached and died, while those that carried the antisense gene stayed green and were subsequently transferred to soil and allowed to flower.

EXAMPLE 35

Figure 15A:
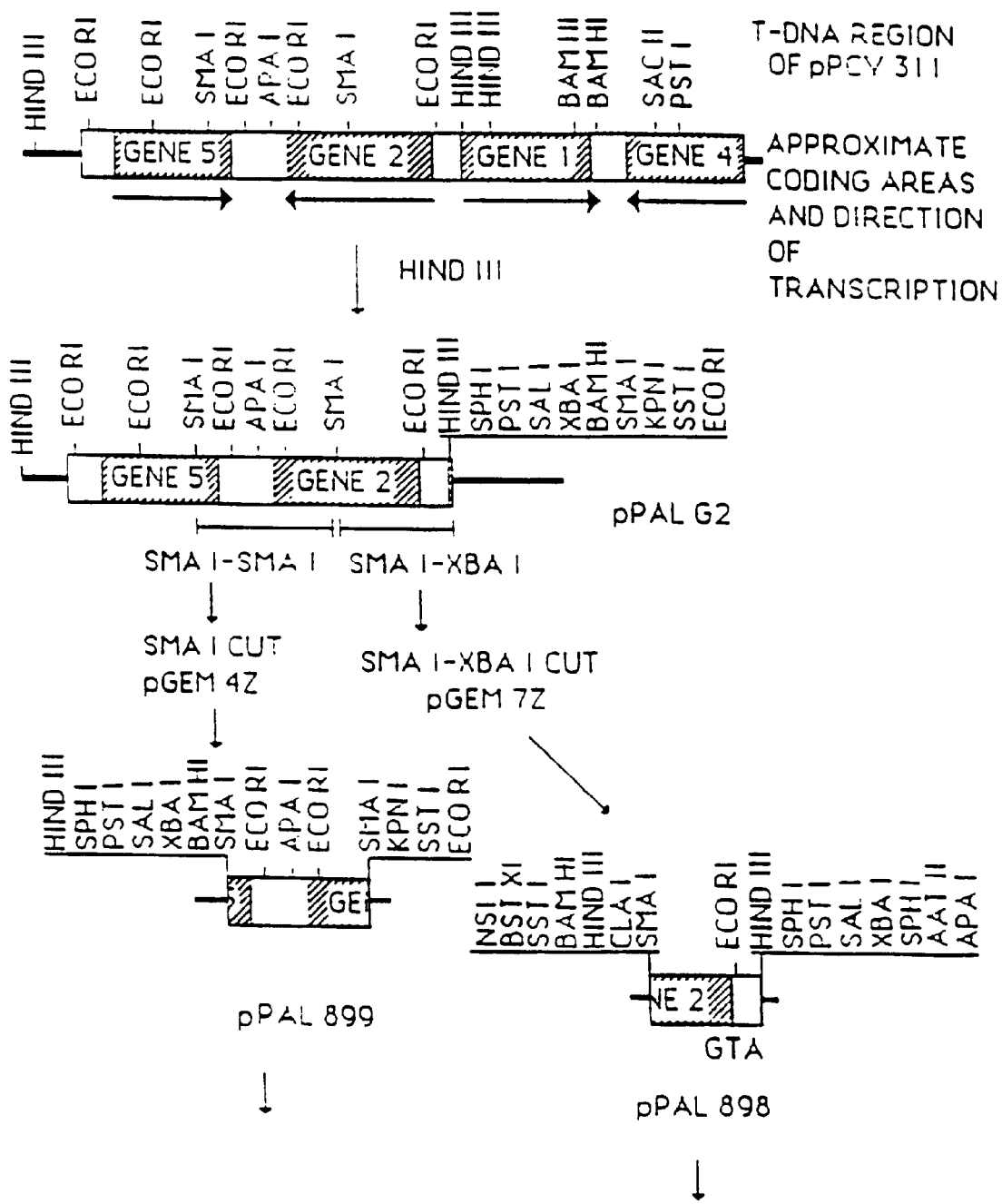
FIGS. 15A–15B illustrate the procedure used for the isolation of the T-DNA gene 2 (the IamH: indole acetamide hydrolase gene) of the *Agrobacterium tumefaciens* Ti plasmid derivative pPCV 311 (described by Koncz, C. and Schell, J., Molecular and General Genetics, 1986, 204:383–396) and the construction of a promoterless version of this gene.
Figure 15B:
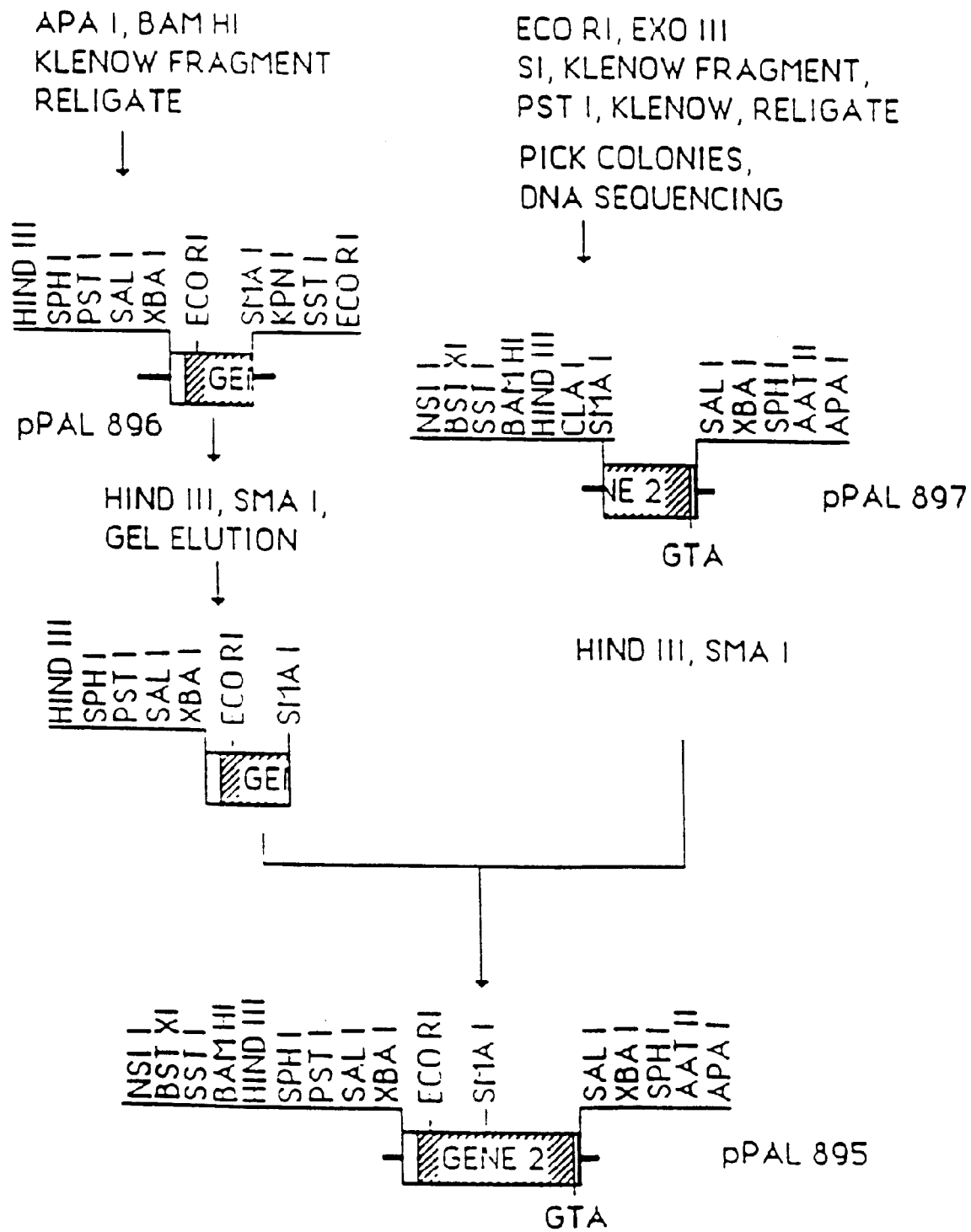

This example describes the isolation of two genes involved in tumor formation in plant tissues following infection with Agrobacterium, the IamS and the IamH genes from the Ti plasmid of the *Agrobacterium tumefaciens* strain C58. The isolation of the IamH gene is particularly described. The source of DNA coding for these genes was the plasmid pPCV 311. The plasmid pPCV311 is described in: Koncz, C. and Schell, J., Molecular and General Genetics, (1986), 204:383–396, and contains the oncogenic region of the T-DNA plasmid contained in the C58 strain of Agrobacterium. The plasmid pPCV 311, contains a region of T-DNA that when transferred to plant cells causes tumor formation. This oncogenic region of the T-DNA is entirely contained in the plasmid pPCV-311. This region of DNA contains four genes, that when expressed in plant cells are sufficient for tumor formation. The approximate ceding regions of these four genes and the direction of transcription of these four genes are indicated in FIG. 15. The other portions of the vector pPCV 311 are not shown in that they are not relative to the following constructions. Additionally, the oncogenic region of the Agrobacterium strain C58 is located on the T-DNA plasmid within that bacterium, commonly referred to as the wild-type nopaline plasmid. A nearly identical oncogenic region is also found in wild type octopine strains which could also be used as a source of genes. The complete nucleotide sequence of an octopine strain oncogenic region is described by Barker et al., Plant Molecular Biology 2:335–350 (1983). The partial sequence obtained from various constructs of genes derived from pPCV 311 was compared to the published nucleotide sequence.

Two genes were isolated from pPCV 311, the lamH and the lamS genes, commonly referred to as genes 2 and 1 respectively. The lamH gene was isolated by first subcloning the indicated Hind III fragment, a fragment that contains all of the coding region of gene 2 and additional 5' sequences that were subsequently removed for the construction of a promoterless version of the gene. The restriction sites mapped in this subclone are shown in FIG. 15 and the subclone is referred to as pPAL G2. For the isolation of coding sequences only, pPAL G2 was first split into two smaller clones and the gene later reconstructed. The Xba I-Sma I and Sma I-Sma I fragments shown in FIG. 15 were isolated by gel elution and subsequently cloned into the following vectors: The Sma I-Sma I fragment was cloned into pGEM 4Z, giving rise to pPAL 899. The Xba I-Sma I fragment was subcloned into pGEM 7Z, giving rise to pPAL 898. The 5' non-coding sequences of the lamH gene that are present in this subclone were removed in the following fashion: pPAL 898 was digested with Eco RI, the Eco RI site is in the promoter region of the clone, and in this subclone is the only Eco RI site. This digested DNA was then treated with Exonuclease III, and following digestion treated with S1 nuclease and the Klenow fragment of DNA polymerase I. The treated DNA was then cut with Pst I and treated with Klenow fragment in order to make the Pst I site blunt. The linear, digested, blunt ended plasmid was then relegated and used to transform *E. coli* DH5-alpha according to standard protocols. Subclones were chosen, sequenced and one subclone was chosen that was deleted to 8 nucleotides in front of the ATG start of translation codon. The ATG start codon was determined by comparison of the nucleotide sequence obtained from the deleted subclones to the nucleotide sequence for the octopine strain described by Barker, et al. Plant Molecular Biology 2:335–350 (1983). The nucleotide sequences of both the 5' non-coding and the coding region were nearly identical. This subclone was named pPAL 897, the ATG codon is shown in FIG. 15, the direction of transcription in this case would be from right to left in FIG. 15. The plasmid contained the 5' half of the coding region from the lamH gene, with the promoter sequences deleted.

The construction of the 3' half of the lamH gene, contained in the plasmid pPAL 898 was carried out as follows. A 3' region of the gene that contains the polyadenylation signal naturally found in the gene was isolated by digestion pPAL 898 with the enzymes Bam HI and Apa I. The digested DNA was treated with Klenow fragment to make it blunt ended and was relegated. This gave rise to the subclone pPAL 896, which is a plasmid that contains the 3' half of the lamH gene. To reconstruct the intact lamH gene, pPAL 896 was digested with Hind III and Sma I, and the 3' half gene fragment was isolated by gel elution. pPAL 897 was digested with Sma I and Hind III and the isolated 3' fragment from pPAL 896 was cloned into these sites, reconstructing a promoterless version of the gene that contains the indicated array of restriction sites flanking the gene. This plasmid was named pPAL 895 and is shown in FIG. 15.

EXAMPLE 36

Figure 16:
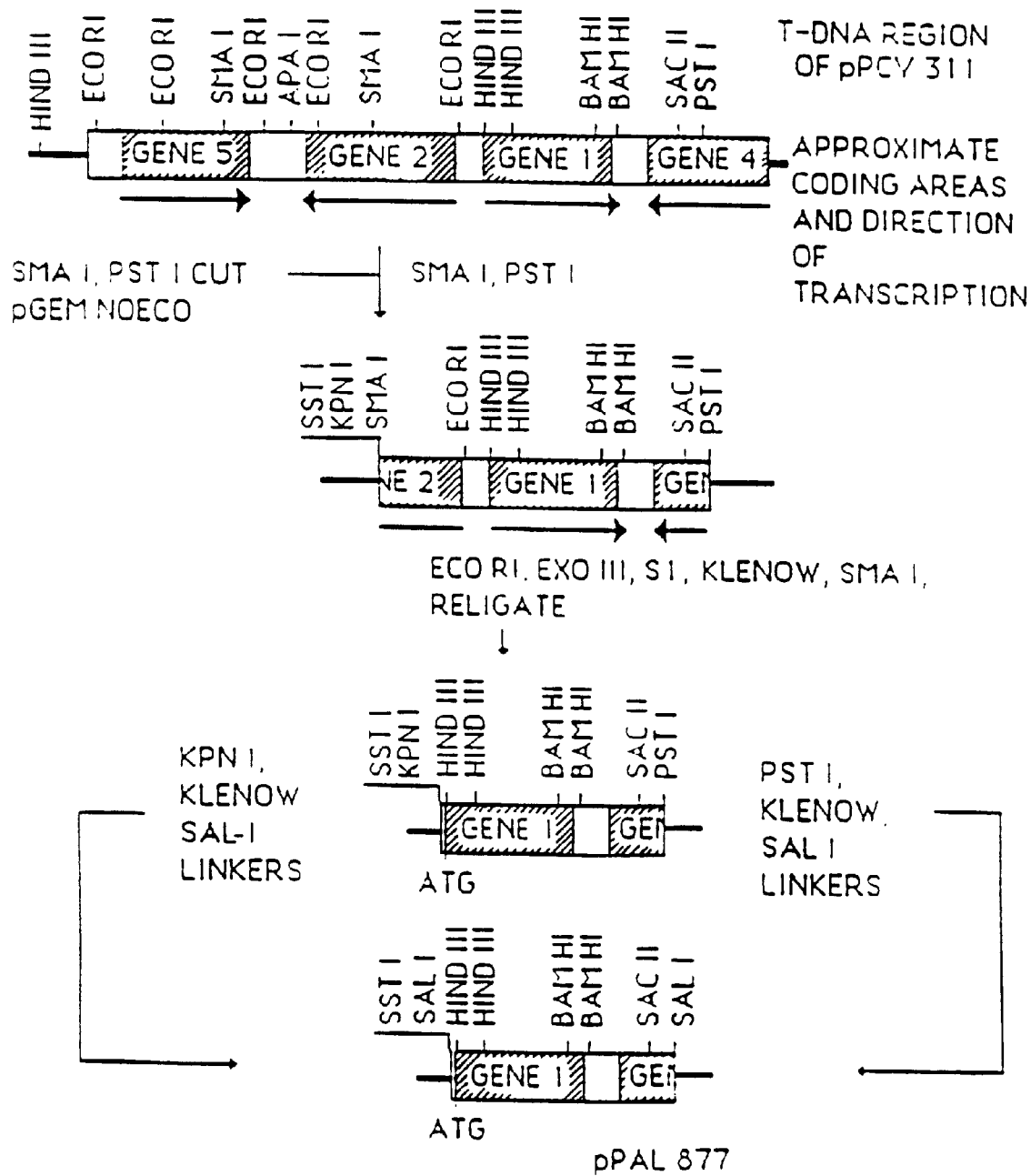
FIG. 16 illustrates the procedure used for the isolation of the T-DNA gene 1 (the IamS: indole acetamide synthase gene) of the *Agrobacterium tumefaciens* Ti plasmid derivative pPCV 311 and the construction of a promoterless version of this gene.

This example describes the isolation and construction of a promoterless version of the gene 1, IamS: indole acetamide synthase gene of the Ti plasmid of the Agrobacterium tumefaciens strain C58 which procedure is summarized in FIG. 16. The gene was isolated from the plasmid pPCV311. The Sma I-Pst I fragment that contains 5' and 3' regions of the lamS gene as well as the coding region was isolated by gel elution and subcloned into a derivative of pGEM 4Z called pGEM-noEco. pGEM-noEco is a plasmid from which the Eco RI site of pGEM 4Z has been removed by cutting with Eco RI and making blunt ended and relegating such that only the Eco RI site was removed. The fragment was inserted in the orientation shown relative to the polylinker. This subclone was called pPAL 889. pPAL 889 was digested with Eco RI, and briefly treated with Exonuclease III, followed by S1 nuclease. The DNA was digested with Sma I and treated with Klenow fragment to make it blunt ended. The DNA was relegated and clones recovered. Some of these clones were chosen, sequenced, and one clone was found which had 5' sequences deleted such that only approximate 15 bases upstream of the ATG start of translation codon remained. This plasmid was named pPAL 888. The Kpn I site at the 5' end of the gene as well as the Pst I site at the 3' end of the gene were both converted to Sal I sites by cutting with Kpn I, end filling with Klenow and adding synthetic Sal I linkers, and repeating the linker addition at the Pst I site such that the entire gene can be excised as a single Sal I fragment. This plasmid was named pPAL 887. This plasmid contains the promoterless version of the lamS gene and contains the array of restriction sites shown that flank the gene as shown in FIG. 16.

EXAMPLE 37

This example relates to the detailed characterization of the coding regions of clone number L4 a microspore specific clone isolated from a *Brassica napus* genomic library and the construction of vectors containing these genes. FIG. 2*a* is a schematic representation of the restriction map and coding regions of clone number L4. The clone contains three different members of the same gene family. These genes are identified as Bp4A, Bp4B and Bp4C. The first (Bp4A) and third (Bp4C) genes are functional, the second gene has modifications that most likely render it non-functional. The restriction map is made diagramatically in that the non-transcribed regions are shown as a single line, while the transcribed regions are shown as a boxed area. The second gene (Bp4B) is identified on the basis of sequence homology and is therefore boxed with a dotted line. The notation "del 220" refers to an approximately 220 base pair deletion/rearrangement affecting the second gene (Bp4B) in this clone. Start of transcription is located at the leftmost side of each boxed area (except in the case of gene Bp4B) and exon and intron positions are noted by the exons being filled in with black and the intron positions being left unfilled. A small arrowhead is shown on the non-transcribed 5' region of each gene, this arrowhead serves to indicate the promoter region of each gene. Restriction sites are identified such that the number of the first nucleotide of the restriction enzyme recognition site is shown. Not all restriction sites are shown, only those relative to the constructs detailed within are indicated. The genes are presented with the 5' region being on the left side and the 3' region being on the right. The numbering of the DNA sequence in all cases starts from left to right, 5' to 3'.

In FIG. 3a, the DNA sequence of the clone L4 is shown, the orientation of the sequence and the genes contained within the microspore specific clone from Brassica napus are from 5' to 3'. In FIG. 3a, clone L4, nucleotide 1 in the complete sequence is at the left-most Eco R1 site while nucleotide 8579 is at the first nucleotide of the right-most Eco R1 site. The start of transcription of gene 1 in clone L4 is nucleotide 235. The 5' and 3' intron splice sites are identified in boldface type. The start ATG codon is shown as well as the stop termination codon. The deduced amino acid sequence of the proteins encoded for by these genes are also shown. The end of transcription for gene 1 is approximately nucleotide 1427. As indicated above the second gene in clone L4 is most likely non-functional due to an insertion and a deletion that occurs in the region of the promoter and first exon. This gene was not utilized for constructs. The third gene in clone L4 has a transcriptional start at position number 6298 in the DNA sequence and transcription ends at approximately nucleotide 7490. The ATG start codon, intron splice sites and termination stop codon are all identified as above. Vectors were constructed from this clone by using promoter fragments from both genes 1 and 2. The specific promoter fragment constructs are detailed below.

The construction of 2 vectors containing promoter and promoter fragments from the clone L4 was carried out as follows and as shown in FIG. 7 (A,B,C,D) The first vector was constructed by first subcloning the Eco R1-Sst 1 (nucl. 1–2132) fragment containing the first gene of clone L4 (235 base pairs of promoter/exon/intron/second exon) in the commercially available vector pGEM-4Z (Promega Biotech, Madison, Wis., U.S.A.) using the Eco R1-Sst 1 sites of the polylinker of this vector. This plasmid was named pPAL 0402. The 2.7 Kb Eco RI fragment of clone L4 that contains the third gene (Bp4C) was then cloned into the Eco RI site of pGEM 4Z, leading to a plasmid called pPAL 0411. The plasmid pPAL 0402 was then digested with Eco R1 and the 2.7 Kb Eco R1 fragment from pPAL 0411 (nucl. 5859–8579) that contains the gene number three (Bp4C) from clone L4 was added to it. Clones were recovered that contained this inserted 2.7 Kb Eco R1 fragment in both orientations relative to the promoter region of the first gene. A clone that contained this third gene fragment in an orientation such that the promoter from the third gene was opposite to the promoter in the first gene was chosen and called pPAL 0403. pPAL 0403 contains the entire third gene from clone L4 oriented in such a fashion as to have the promoter region immediately adjacent to the 235 base pair promoter region of the first gene in pPAL 0403. This plasmid, pPAL 0403 was digested with Dde 1. Dde 1 digestion produced a fragment of approximately 1.9 Kb. The Dde I sites are located at nucleotides 303 and 7366. Because of the orientation of these fragments, digestion with Dde I produces a 1.9 Kb fragment. This 1.9 Kb fragment contains a copy of the third gene (Bp4C) oriented such that the direction of transcription of this third gene is from right to left, fused to the 235 base pair promoter fragment from the first gene of clone L4 Bp4A) which is transcribed from left to right, ending in a Dde I site that is located 67 basepairs down stream of the major start site of transcription and proceeds the ATG start of translation codon by 2 nucleotides. This 1.9 Kb Dde I fragment made blunt with Klenow fragment and cloned into the Xba I site of the polylinker region of pGEM 4Z previously made blunt ended with Klenow fragment. The resultant plasmid pPAL0408, was recovered and subsequently was digested with Sal I and Sst I, which releases the cloned Dde I fragment bordered by on the left hand side, (nucl 7366) Sal I and on the right hand side (nucl 303) of this construct and contains a portion of the polylinker of pGEM 4Z containing the following unique sites: Bam HI, Sma I, Kpn I, and Sst I restriction enzyme sites. This Sal I-Sst I fragment was cloned into the Sal I-Sst I sotes of PAL 1001. PAL 1001 is the binary vector Bin 19 (described by Bevan, M., Nucleic Acids Res., 1984, 12:8711–8721) to which has been added the nor ter polyadenylation signal as a 260 bp Sst I-Eco RI fragment isolated from the plasmid pRAJ 221 (available from Clonetech Laboratories, Palo Alto, Calif., U.S.A.) in the Sst I-Eco RI sites of the polylinker region of Bin 19. The nos ter is identified as a stippled box. The binary transformation vector that resulted from the insertion of the Sal I-Sst I fragment of pPAL 0408 into PAL 1001 was named PAL 1107. The details of the construction are shown in FIG. 7A. This vector has a copy of the third gene oriented such that the direction of transcription of this third gene is from right to left, fused to the 235 base pair promoter fragment from the first gene of clone L4 which is transcribed from left to right, followed by a polylinker with unique sites for the insertion of DNA which consist of: Bam HI, Sma I, Kpn I and Sst I followed by the nos ter. This vector has the feature in that additional 5' non-coding sequences were placed upstream to the 235 base pair core promoter on Bp4A, but these additional 5' sequences were in an opposite orientation. The provision of these sequences in this orientation does not affect the pollen specificity of the core 235 base pair promoter. With this vector, one can also ascertain for position effects of the transformation process in that since the vector contains an intact copy of the Bp4C gene, probing for the levels of expression of the Bp4C gene can give an indication as to what levels of expression from the other pollen specific promoter in PAL 1107 can be expected.

EXAMPLE 38

This example describes the construction of additional vectors having the promoter regions of the genes contained in clone L4 whcih may be useful for pollen specific expression of gene sequences. The three genes within clone L4 (Bp4A, Bp4B, Bp4C) show very near-exact DNA homology and this is most apparent between the first (Bp4A) and third (Bp4C) gene. The second gene (Bp4B) is a homologous copy that has undergone sequence changes that have appear to have lead to inactivation of it. The extensive similarity between the first, second and third genes in clone L4 is also maintained in the promoter region such that out of the first 235 nucleotides of the first and third gene promoter regions there are only 5 nucleotides that differ between them. Downstream of the TATA box in these two promoters the only difference between them is the presence of one additional nucleotide at the start of transcription (e.g. Promoter 1,Bp4A: . . . TATGTTTtAAAA . . . versus promoter 3,3p4c: . . . TATGTTTAAA (transcribed region underlined, single nucleotide difference shown in lower case). However, within the sequence of the first gene there is a nucleotide change that introduces a Dde I site (nucl 303) in the untranslated 5' leader sequence upstream of the ATG start codon that is not present in the untranscribed leader sequence of the third gene in clone L4. For this reason, chimeric promoter constructs were made which utilized this Dde I site in the first gene joined to sequences from the third gene promoter. The region of the first promoter used for these constructs consisted of the sequences contained between the Sna BI site (nucl 210) near the TATA box to the Dde I site located immediately upstream of the ATG start codon in the first gene (nucleotide 303 is the first nucleotide in the recognition sequence for Dde I). The other region of this chimeric promoter (5' of the TATA box) was a fragment extending from the Eco RI site of the third promoter (nucleotide 5858) to the Sna BI site near the TATA box (nucleotide 6273). Therefore to facilitate construction of these pollen specific vectors, the following reconstructions were performed.

The Eco RI to Dde I fragment that encompasses the promoter region of the first gene in clone L4 was isolated by first cutting pPAL 0402 with Dde I, blunting with Klenow, and then cutting with Eco RI. The 235 base pair fragment corresponding to this region was cloned into the Eco RI-Sma I sites of pGEM 4Z. This plasmid (pPAL 0422), was then cut with Eco RI and Sna BI. A DNA fragment that contained the Eco RI to Sna BI portion of the promoter for gene 3 in clone L4 was isolated by digesting pPAL 0411 with Eco RI and Sna BI. This released an approximately 415 base pair Eco RI (nucl 5858) to Sna BI (nucl 6273) fragment that represents most of the 5' region of the gene 3' promoter from clone L4 (the Sna BI recognition site is 2 base pairs downstream of the TATA box). This Eco RI-Sna BI fragment was used to replace the shorter Eco RI-Sna BI fragment removed from the first promoter subclone (pPAL 0422), reconstructing a promoter fragment of approximately 550 base pairs. This plasmid is referred to as pPAL 0421. This chimeric promoter fragment contains 415 base pairs of the promoter of gene three in clone L4, followed by approximately 99 nucleotides of the first gene promoter/untranslated leader sequence.

For construction of a pollen specific cassette vector, the following plasmids were first constructed. The first plasmid constructed contained the nos ter polyadenylation signal with a polylinker in front of the nos ter. This was accomplished by first isolating from pRAJ 221 the nos ter as a Sst I-Eco RI fragment and this fragment was cloned in pGEM 4Z using the Sst I and Eco RI sites in the polylinker. This subclone is referred to as pPAL 001. To pPAL 001, a fragment coding for neomycin phosphotransferase (NPT II) derived from the plasmid pRAJ 162 was added to it in the antisense orientation as follows: The plasmid pRAJ 162 contains the NPT II gene from the transposon TN 5 inserted as a Sal I fragment and bounded by a polylinker in the plasmid pUC-9 and was obtained from the Plant Breeding Institute, Cambridge, U.K. pRAJ 162 was digested with Hind III and Sma I. The DNA fragment containing the NPT II gene was isolated by elution from an agarose gel. pPAL 001 was digested with Hind III and Sma I and the NPT II gene fragment was ligated into it. The resultant plasmid was called pPAL 002 and had such orientation of restriction sites and the NPT II gene and nos ter as follows: Hind III, Pst I, Sal I, 3' end NPT II coding sequence 5' end, Sal I, Bam HI, Sma I, Kpn I, Sst I, nos ter, Eco RI. pPAL 002 was cut with Hind III and the site made blunt ended by the use of Klenow fragment. pPAL 0421 was digested with Hinc II and Pvu II, both of which leave blunt ends, and the promoter fragment was ligated into Hind III cut blunt ended pPAL 002. Plasmids were obtained that contained the promoter in both orientations relative to the nos ter. One plasmid was chosen with the proper orientation (5' promoter/antisense NPT II/nos ter) and was named pPAL 0419. pPAL 0419 has the following DNA fragments: A small (approx. 130 bp) of pGEM 4Z that contains the SP6 promoter, the 550 base pair chimearic promoter, the NPT II gene in the antisense orientation relative to the promoter, followed by the nos ter polyadenylation signal. This entire promoter/NPT II/nos ter construct is excisable by Eco RI. In order to provide promoter sequences that could be utlized with additional gene constructs, the plasmid pPAL 0419 was digested with Sal I. This digest removes the NPT II coding region and this Sal I digested pPAL 0419 was relegated giving rise to pPAL 0402. pPAL 0420 represents the pollen specific promoter followed by a polylinker for insertion of genes that has the following unique sites: Hinc II, Pst I, Sal I, Bam HI, Sma I, Kpn I, Sst I, followed by the nos ter polyadenylation signal. The entire promoter/polylinker/nos ter construct can be conveniently excised as a single Eco RI fragment. The details of this construct is shown in FIG. 7B. This plasmid was used for the construction of an additional pollen specific promoter in a binary transformation vector. The intact L4 clone in the lambda cloning vector was digested to completion with the restriction enzymes Sst I and Hha I. The resultant fragments were separated by gel electrophoresis and a 2.65 Kb fragment that contains the promoter/first exon/intron/partial second exon region of gene three in clone L4 and corresponds to nucleotides 4565 to 7216 in the sequence of clone L4 was isolated. This fragment was made blunt ended with Klenow and cloned into the binary transformation vector PAL 1001 previously described with reference to FIG. 7a. PAL 1001 was first cut with Hind III and made blunt ended with Klenow. Clones containing this fragment (promoter/first exon/intron/partial second exon) were recovered. A clone was chosen that contained this fragment in the proper orientation such that the direction of transcription was towards the nos ter in PAL 1001. This vector was named PAL 1421. This vector contains approximately 1.9 kb of upstream promoter region from the gene 3 in clone L4 followed by the first exon, the complete intron and 15 bases of the second exon of gene three followed by a polylinker containing the following unique sites: Sal I, Xba I, Bam HI, Sma I, Kpn I, Sst I, and finally the nos term polyadenylation signal. A varient of this vector was constructed by digesting PAL 1421 with Eco RI and replacing the promoter/exon/intron/ second exon/polylinker/nos ter structure with the promoter/polylinker/nos ter structure from pPAL 0420 using Eco RI such that a longer 5' promoter region is reconstructed in the binary transformation vector. The resultant vector was named PAL 1423. The outline of this construction is shown in FIG. 7D.

EXAMPLE 39

In this example, a pollen specific promoter is used to synthesize the enzyme IamH specifically in pollen cells. The enzyme has activity that can cause the production of NAA from NAM, the substance NAA functioning as a plant hormone that is substantially toxic to developing pollen grains, while the precursor NAM being relatively non-toxic. For this example, the IamH gene was inserted into the vector PAL 1423. The IamH gene was isolated from pPCV311 as described in FIG. 15 and cloned as a Sal I fragment in the Sal I site of PAL 1423, creating PAL 1426. This vector has the IamH gene (T-DNA gene 2) under the control of a pollen specific promoter from clone L4 in the sense orientation. PAL 1426 was used to transform Tobacco as outlined in Example 34.

EXAMPLE 40

The vector PAL 1426 was used to transform *Brassica napus* as described in Example 34.

EXAMPLE 41

In this example, the vector PAL 1107 was used for the production of tissue-specific GUS beta-glucuronidase) enzyme. The gene for this enzyme is available from Clonetech Laboratories, Palo Alto. Calif., U.S.A. The gene was inserted to PAL 1107 as a Bam HI-Sst I fragment and was used to transform tobacco as described in Example 34. Plants produced had detectable GUS activity only in developing pollen cells, and not any other tissue tested.

The application of a non-toxic analog of glucuronic acid to which has been conjugated a toxic molecule could be applied to these plants and cleavage of the toxic moiety from the glucuronic acid would occur only in pollen cells. This provides an example of an enzyme that could be used for the production, in a tissue-specific fashion, of a toxic substance from a non-toxic analog. One such analog that could be used is Gluc-Camp, a glucuronic acid analog that is conjugated to chloramphenicol. When acted upon by glucoronidase, chloramphenicol is produced, inhibiting cellular growth and development.

EXAMPLE 42

In this example, two isogenic plant lines (A1, A2) were produced that carried either the IamS or the IamH genes. Tobacco plants were transformed with PAL 1426 containing the IamH gene as in Example 39, producing the A2 line. The IamS gene described in FIG. 16 was inserted as a Sal I fragment into the vector PAL 1423 in the sense orientation, giving rise to PAL 1425. PAL 1425 was used to transform tobacco as described and tobacco plants were produced that carried PAL 1425. These lines represented the A1 lines. Tobacco plants that contained both PAL 1426 and PAL 1425 were selfed and homozygous A1 and A2 lines were selected.

EXAMPLE 43

In this example, PAL 1426 (see Example 39) and PAL 1425 were used to transform *Brassica napus*. Plants lines homozygous for the A1 and A2 genes were selected as in Example 42.

We claim:

1. An isolated recombinant DNA molecule comprising:

(a) a DNA sequence which encodes a gene product which, when produced in a cell of a plant, is capable of converting a non-toxic substance to a cytotoxic substance, and the cytotoxic substance is capable of interfering with the function or development of said cell; and (b) a promoter capable of causing the transcription of said DNA sequence preferentially in cells critical to pollen formation or function.

2. A method of producing hybrid plant seed comprising crossing a genetically transformed male-sterile plant with a male-fertile male parent plant, wherein said genetically transformed male-sterile plant comprises a first recombinant DNA molecule according to claim 1, and wherein said male-fertile male parent plant comprises a second recombinant DNA sequence which compensates for the effects caused by expression of said first recombinant DNA molecule.

3. A method for producing a male sterile plant comprising the steps of:

(a) obtaining a transformed plant cell that has been genetically transformed with a DNA molecule according to claim 1;

(b) regenerating from said transformed plant cell a genetically transformed plant; and growing the plant under conditions where male sterility is achieved.

4. Hybrid seed of a pollen-producing plant having a nuclear genome incorporating one or more recombinant DNA molecules as claimed in claim 1, and at least one restorer DNA molecule which negates the effects caused by expression of said one or more recombinant DNA molecules.

5. A method of producing hybrid plant seed comprising crossing a genetically transformed male-sterile plant with a male-fertile male parent plant, wherein said genetically transformed male-sterile plant comprises a first recombinant DNA molecule according to claim 1.

* * * * *